(12) United States Patent
Sauer et al.

(10) Patent No.: US 11,918,204 B2
(45) Date of Patent: Mar. 5, 2024

(54) SUTURING DEVICE FOR MINIMALLY INVASIVE SURGERY AND NEEDLES AND METHODS THEREOF

(71) Applicant: LSI Solutions, Inc., Victor, NY (US)

(72) Inventors: Jude S. Sauer, Pittsford, NY (US); Matthew R. Wrona, Fairport, NY (US)

(73) Assignee: LSI Solutions, Inc., Victor, NY (US)

( * ) Notice: Subject to any disclaimer, the term of this patent is extended or adjusted under 35 U.S.C. 154(b) by 13 days.

(21) Appl. No.: 17/727,235

(22) Filed: Apr. 22, 2022

(65) Prior Publication Data

US 2022/0240926 A1 Aug. 4, 2022

Related U.S. Application Data

(63) Continuation of application No. 16/259,666, filed on Jan. 28, 2019, now Pat. No. 11,337,688, which is a
(Continued)

(51) Int. Cl.
*A61B 17/062* (2006.01)
*A61B 17/04* (2006.01)
(Continued)

(52) U.S. Cl.
CPC ...... *A61B 17/0469* (2013.01); *A61B 17/0482* (2013.01); *A61B 17/06004* (2013.01);
(Continued)

(58) Field of Classification Search
CPC .............. A61B 17/069; A61B 17/0482; A61B 17/0485; A61B 17/0491; A61B 17/06004;
(Continued)

(56) References Cited

U.S. PATENT DOCUMENTS 1,822,330 A 9/1931 Ainslie
2,646,045 A 7/1953 Priestly
(Continued)

FOREIGN PATENT DOCUMENTS

EP 0634141 1/1995
EP 1945107 7/2008
(Continued)

OTHER PUBLICATIONS

International Search Report for PCT Patent Application No. PCT/US2014/68742, filed Dec. 5, 2014, dated Apr. 30, 2015.
(Continued)

*Primary Examiner* — Kathleen S Holwerda
(74) *Attorney, Agent, or Firm* — Michael E. Coyne

(57) ABSTRACT

A suturing device for minimally invasive surgery is disclosed. The suturing device has a head defining one or more ferrule holders and a tissue bite area. The device also has a first needle comprising a flywheel portion and one or more curved arms extending from the flywheel portion, each of the one or more curved arms comprising a ferrule engaging tip, wherein the first needle is pivotably coupled to the head. The suturing device further has a first actuator coupled to the first needle and configured to rotate it from a retracted position, where the ferrule engaging tip of each of the one or more curved arms starts away from the one or more ferrule holders, through the tissue bite area, and to an engaged position where the ferrule engaging tip of each of the one or more curved arms is operationally aligned with the one or more ferrule holders.

19 Claims, 81 Drawing Sheets

Related U.S. Application Data continuation-in-part of application No. 14/727,235, filed on Jun. 1, 2015, now Pat. No. 11,033,260.

(60) Provisional application No. 62/622,923, filed on Jan. 28, 2018.

(51) Int. Cl.
*A61B 17/06* (2006.01)
*A61F 2/24* (2006.01)
*A61B 17/00* (2006.01)

(52) U.S. Cl.
CPC .... *A61B 17/06066* (2013.01); *A61B 17/0625* (2013.01); *A61F 2/2448* (2013.01); *A61F 2/2457* (2013.01); *A61F 2/2466* (2013.01); *A61B 2017/00243* (2013.01); *A61B 2017/00367* (2013.01); *A61B 2017/00783* (2013.01); *A61B 2017/0472* (2013.01); *A61B 2017/06042* (2013.01); *A61B 2017/0608* (2013.01)

(58) Field of Classification Search
CPC ........ A61B 17/06066; A61B 17/06114; A61B 17/06128; A61B 17/06166; A61B 17/0625; A61B 17/29; A61B 2017/00004; A61B 2017/00296; A61B 2017/00367; A61B 2017/00477; A61B 2017/00862; A61B 2017/047; A61B 2017/0496; A61B 2017/06009; A61B 2017/06042; A61B 2017/06076; A61B 2017/0608; A61F 2/2457; A61F 2/2466
See application file for complete search history.

(56) References Cited

U.S. PATENT DOCUMENTS

| | | | |
|---|---|---|---|
| 4,557,265 A | 12/1985 | Andersson | |
| 5,431,666 A | 7/1995 | Sauer | |
| 5,527,321 A | 6/1996 | Hinchliffe | |
| 5,562,686 A | 10/1996 | Sauer | |
| 5,662,663 A | 9/1997 | Shallman | |
| 5,713,910 A | 2/1998 | Gordon | |
| 5,741,279 A | 4/1998 | Gordon | |
| 5,766,183 A | 6/1998 | Sauer | |
| 5,860,990 A | 1/1999 | Nobles | |
| 5,911,727 A | 6/1999 | Taylor | |
| 6,059,719 A | 5/2000 | Yamamoto | |
| 6,368,334 B1 | 4/2002 | Sauer | |
| 6,533,796 B1 | 3/2003 | Sauer | |
| 6,997,931 B2 | 2/2006 | Sauer | |
| 7,144,401 B2 | 12/2006 | Yamamoto | |
| 7,211,093 B2 | 5/2007 | Sauer | |
| 7,407,505 B2 | 8/2008 | Sauer | |
| 7,731,727 B2 | 6/2010 | Sauer | |
| 7,862,572 B2 | 1/2011 | Meade | |
| 7,993,354 B1 | 8/2011 | Brecher | |
| 8,021,376 B2 | 9/2011 | Takemoto | |
| 8,066,737 B2 | 11/2011 | Meade | |
| 8,211,143 B2 | 7/2012 | Stefanchik | |
| 8,236,013 B2* | 8/2012 | Chu | A61B 17/0625 606/139 |
| 8,313,496 B2 | 11/2012 | Sauer | |
| 8,398,657 B2 | 3/2013 | Sauer | |
| 8,652,149 B2 | 2/2014 | Sauer | |
| 8,852,212 B2 | 10/2014 | McClurg | |
| 9,017,346 B2 | 4/2015 | Kia | |
| 9,439,646 B2 | 9/2016 | Chin | |
| 9,603,592 B2 | 3/2017 | Chin | |
| 9,844,367 B2 | 12/2017 | Kobylewski | |
| 2002/0107530 A1 | 8/2002 | Sauer | |
| 2002/0116010 A1 | 8/2002 | Chung | |
| 2002/0116011 A1 | 8/2002 | Chung | |
| 2002/0198542 A1 | 12/2002 | Yamamoto | |
| 2003/0233104 A1 | 12/2003 | Gellman | |
| 2004/0068272 A1 | 4/2004 | Sauer | |
| 2004/0236356 A1 | 11/2004 | Rioux | |
| 2005/0154402 A1 | 7/2005 | Sauer | |
| 2005/0165419 A1 | 7/2005 | Sauer | |
| 2006/0282088 A1 | 12/2006 | Ryan | |
| 2007/0162052 A1 | 7/2007 | Hashimoto | |
| 2007/0255296 A1 | 11/2007 | Sauer | |
| 2009/0222027 A1 | 9/2009 | Sauer | |
| 2010/0042116 A1 | 2/2010 | Chui | |
| 2011/0046644 A1 | 2/2011 | McClerg | |
| 2011/0118758 A1 | 5/2011 | Sauer | |
| 2011/0190793 A1 | 8/2011 | Nobles | |
| 2011/0270279 A1 | 11/2011 | Badhwar | |
| 2012/0016383 A1 | 1/2012 | Sauer | |
| 2012/0165838 A1 | 6/2012 | Kobylewski | |
| 2013/0041388 A1 | 2/2013 | Lane | |
| 2013/0245646 A1 | 9/2013 | Lane | |
| 2014/0214038 A1 | 7/2014 | Mordehai | |
| 2014/0236193 A1* | 8/2014 | Chin | A61F 2/0063 606/228 |
| 2014/0276989 A1 | 9/2014 | Lane | |
| 2015/0057683 A1 | 2/2015 | Meade | |
| 2015/0088167 A1* | 3/2015 | Chin | A61B 17/0469 606/145 |
| 2015/0127024 A1 | 5/2015 | Berry | |
| 2015/0201926 A1 | 7/2015 | Sauer | |
| 2016/0345959 A1 | 12/2016 | Sauer | |
| 2016/0345961 A1 | 12/2016 | Sauer | |
| 2017/0007234 A1 | 1/2017 | Chin | |

FOREIGN PATENT DOCUMENTS

| | | |
|---|---|---|
| EP | 2289426 | 3/2011 |
| EP | 1839592 B1 | 12/2011 |
| JP | S59-149133 | 8/1984 |
| JP | H11-299799 | 11/2011 |
| WO | 1995011630 | 5/1995 |
| WO | 2007/030753 | 3/2007 |
| WO | 2014052599 | 4/2014 |
| WO | 2014164868 | 10/2014 |
| WO | 2015085145 | 6/2015 |

OTHER PUBLICATIONS

International Search Report and Written Opinion for PCT Patent Application No. PCT/US2016/35189 filed Jun. 1, 2016, dated Sep. 8, 2016.

International Search Report and Written Opinion for PCT Patent Application No. PCT/US2016/35197 filed Jun. 1, 2016, dated Sep. 21, 2016.

U.S. Office Action, dated May 25, 2018 for U.S. Appl. No. 14/127,418, filed Jun. 1, 2015.

U.S. Office Action, dated Jan. 29, 2018 for U.S. Appl. No. 14/727,480, filed Jun. 1, 2015.

U.S. Office Action, dated Jan. 21, 2020 for U.S. Appl. No. 15/839,175, filed Dec. 12, 2017.

JP Office Action dated Dec. 18, 2018 for JP2017-560740 filed Jun. 1, 2016.

JP Office Action dated Dec. 18, 2018 for JP2017-560748 filed Jun. 1, 2016.

Supplementary European Search Report dated May 15, 2018 for EP 16804292 filed Jun. 1, 2016.

Extended European Search Report dated Jul. 15, 2021 for EP Application No. 19747493 filed Jan. 28, 2019.

Extended European Search Report dated Mar. 28, 2018 for EP Application No. 16804296 filed Dec. 13, 2017.

Sew-Right SR-5 Device and SR-5 Quick Load, Inservice Guide, LSI Solutions, Inc., May 2011, 19 pages.

Product Literature, RD Running Device, Surgery's Best Suturing Technology, LSI Solutions, Inc., May 2011, 2 pages.

Product Literature, RD Technology Guide, LSI Solutions, Inc., May 2011, 6 pages.

(56) References Cited

OTHER PUBLICATIONS

Product Literature, Sew-Right SR-5, The Single Squeeze Suturing Device, LSI Solutions, Inc., May 2011, 6 pages.
Leigh, H., For Presentation at the STS 2011 Annual Meeting, Fig. 1 Fresh Porcine Heart Bursting Pressure Study Comparing Transapical Access Wound Automated Closures to Hand Sutured Controls, Jun. 21, 2010, 1 page.
P. A. Knight, et al., Automated Remote Transapical Wound Closure System: Fresh Porcine Heart Bursting Pressure Study and Cadaver Endoscopic Demostration, Abstract Central, Jun. 16, 2010, 3 pages.
JP Office Action dated Oct. 11, 2022 for JP2020-539045 filed Jul. 15, 2020.

* cited by examiner

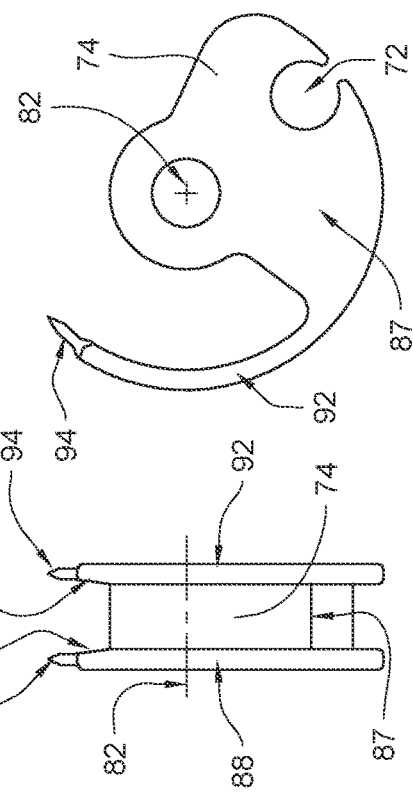
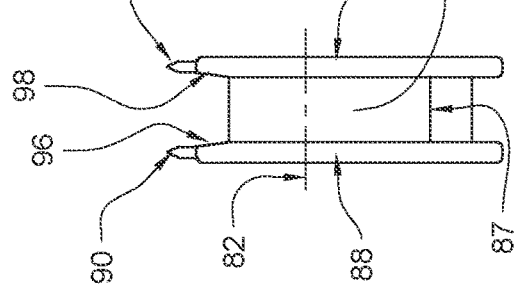
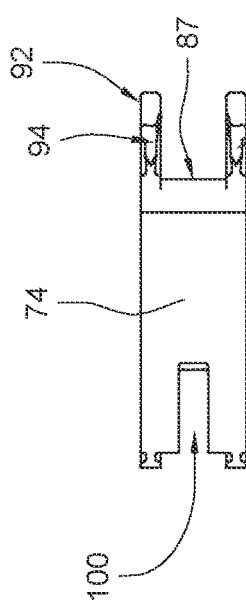
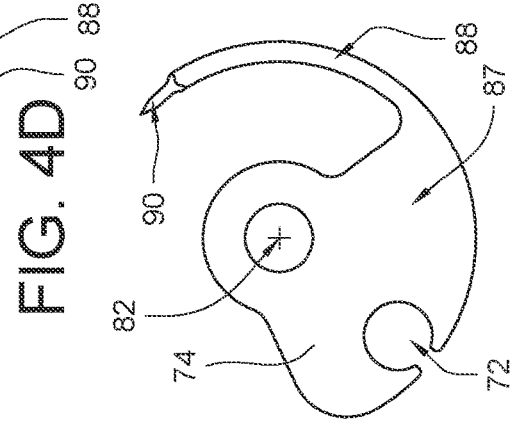
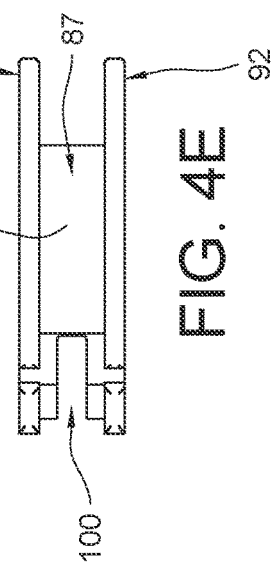
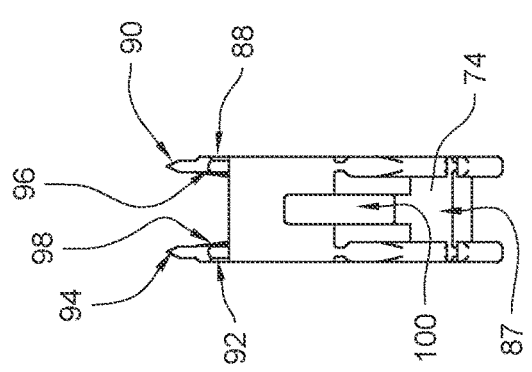

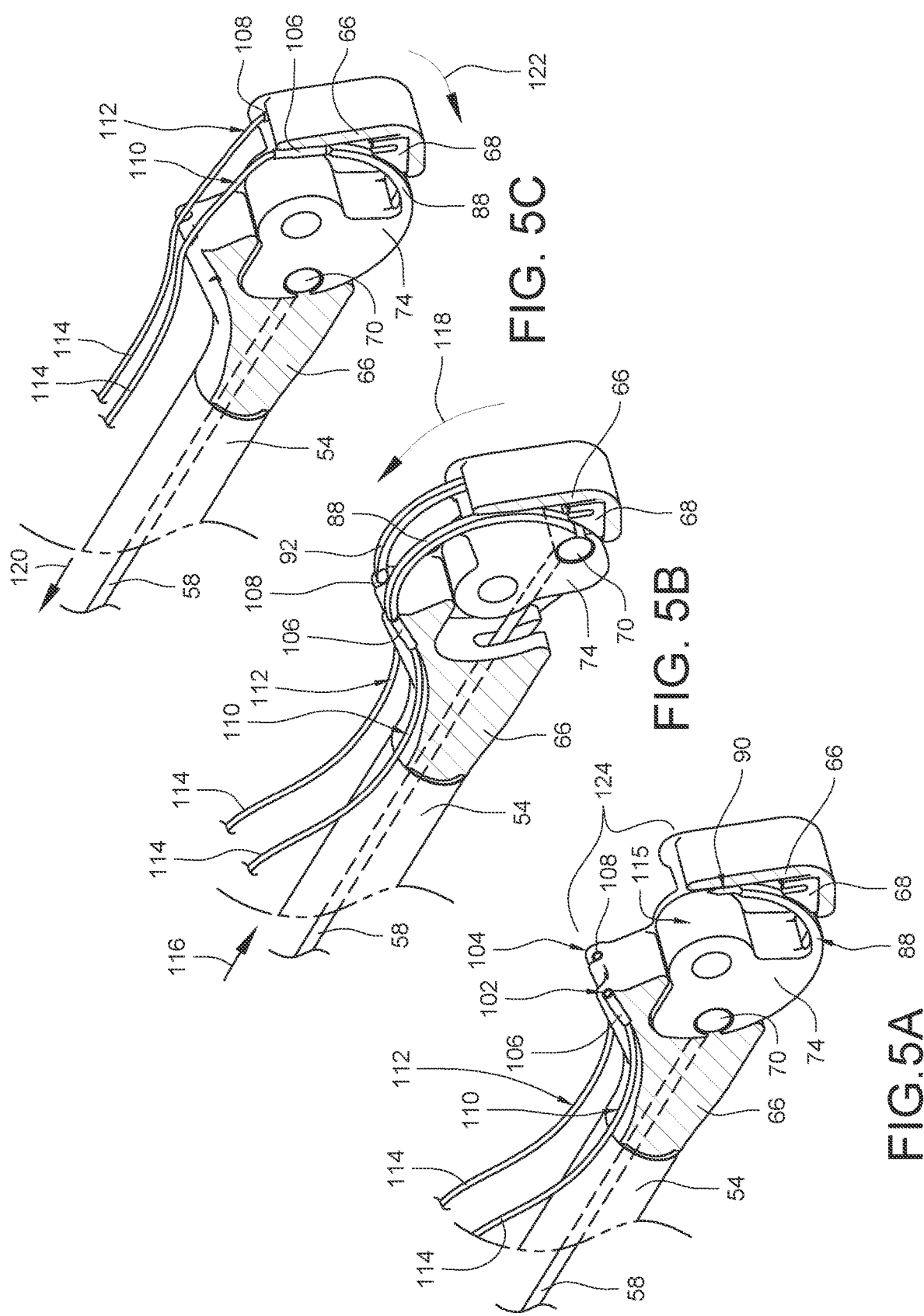

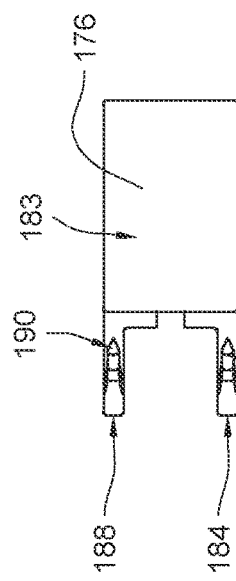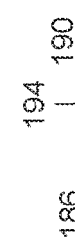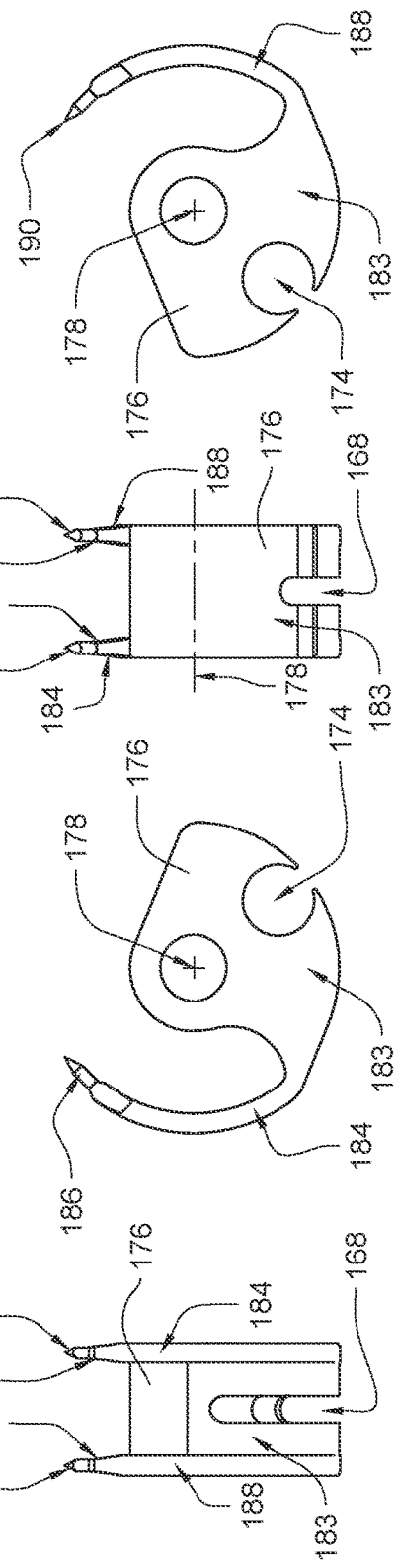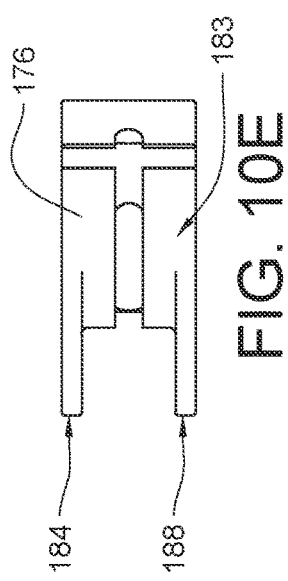
FIG. 10A  FIG. 10B  FIG. 10C  FIG. 10D  FIG. 10E  FIG. 10F

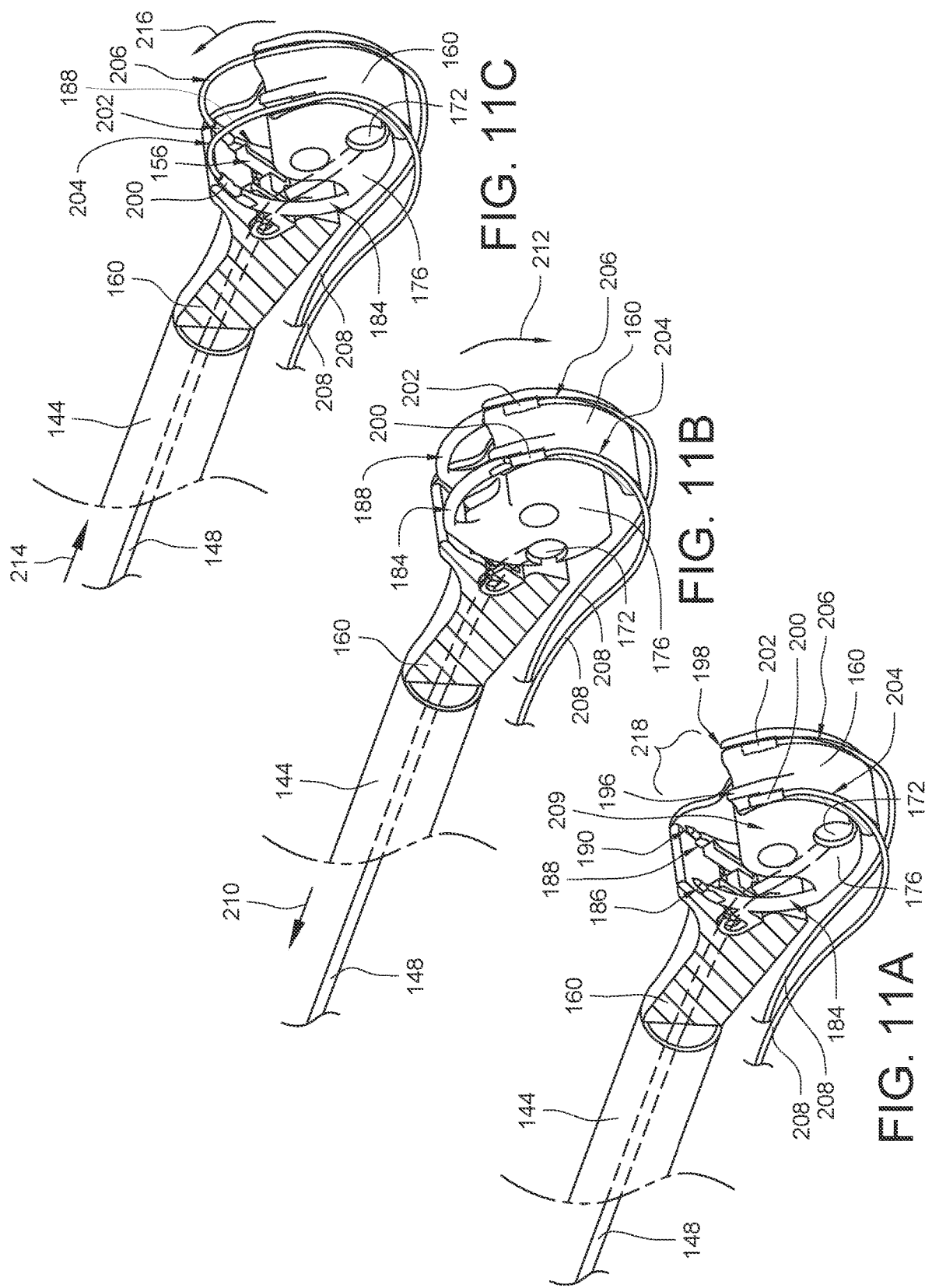

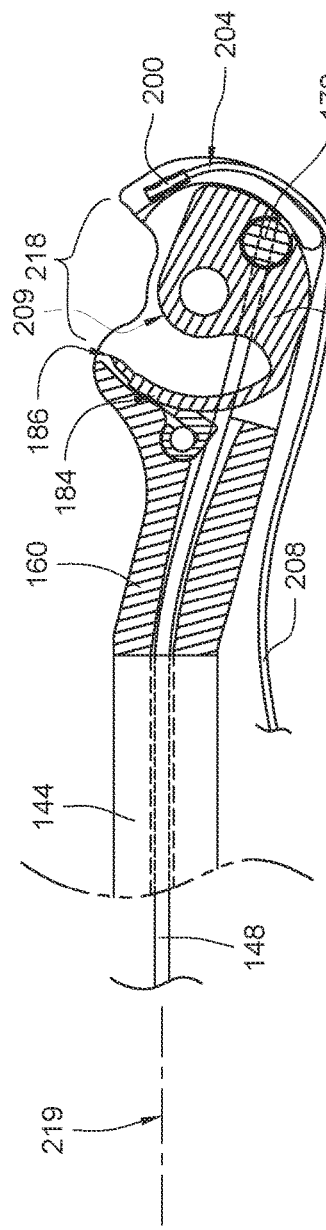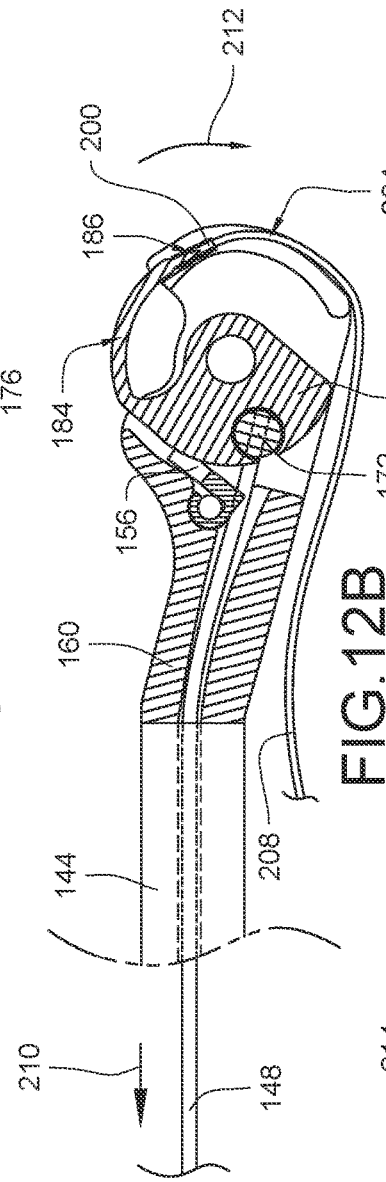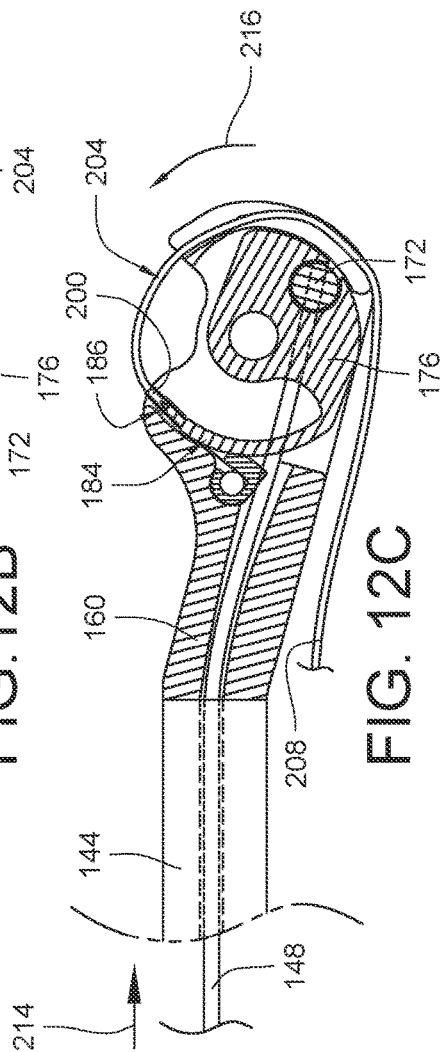

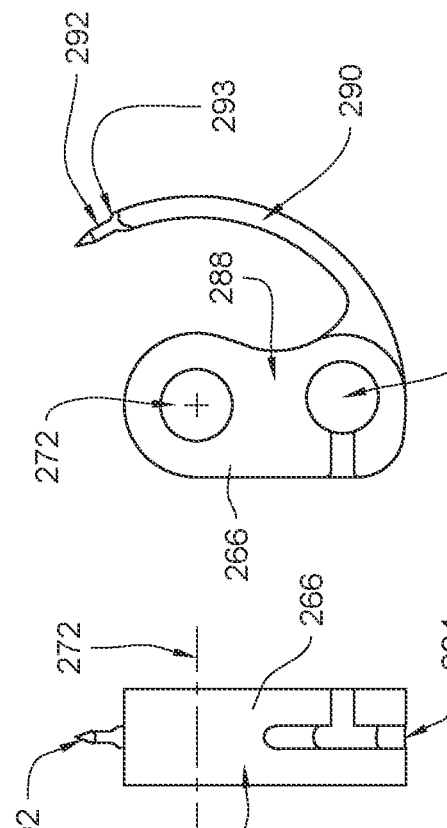
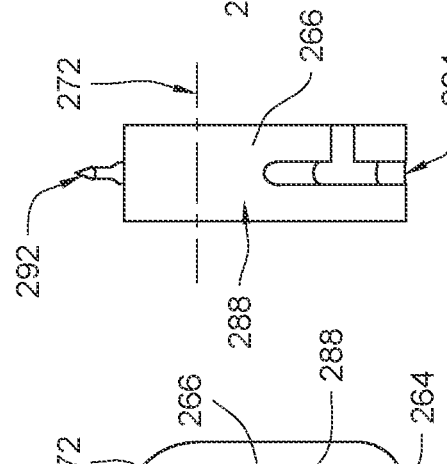
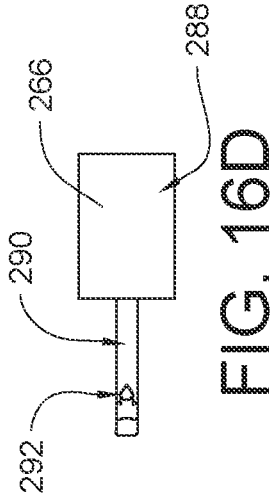
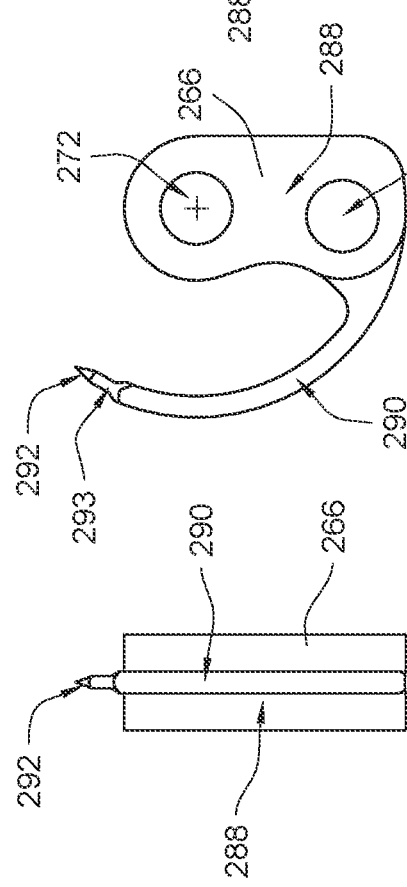
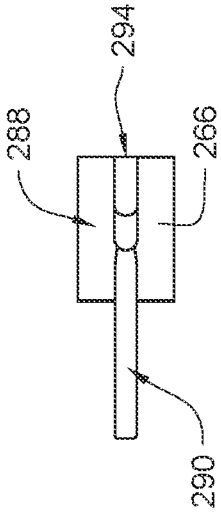

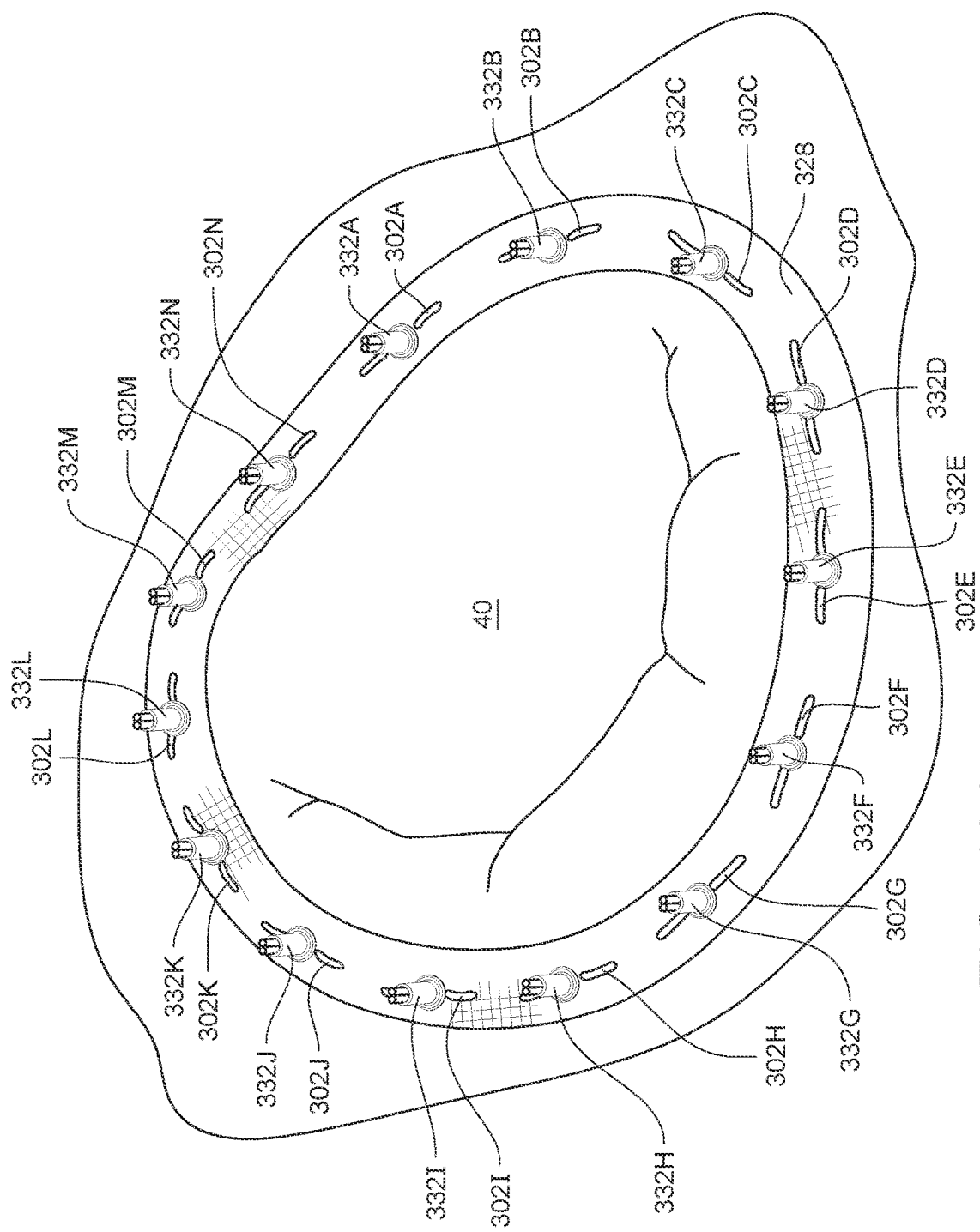

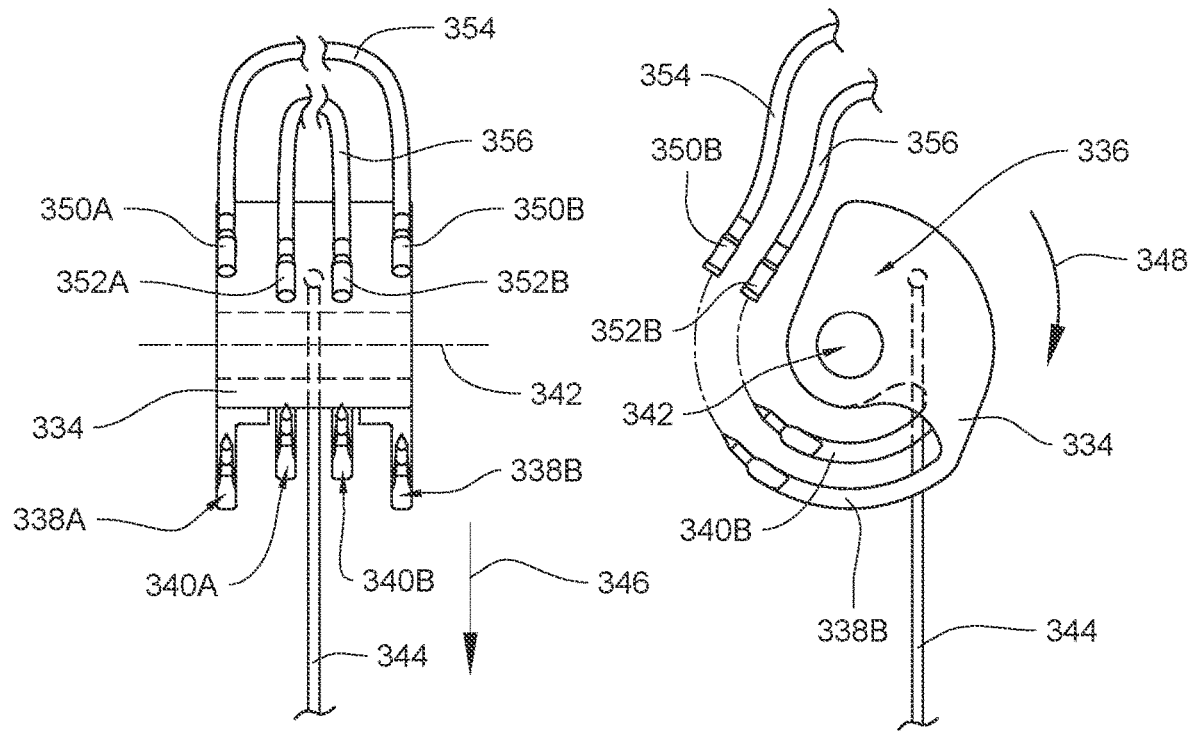
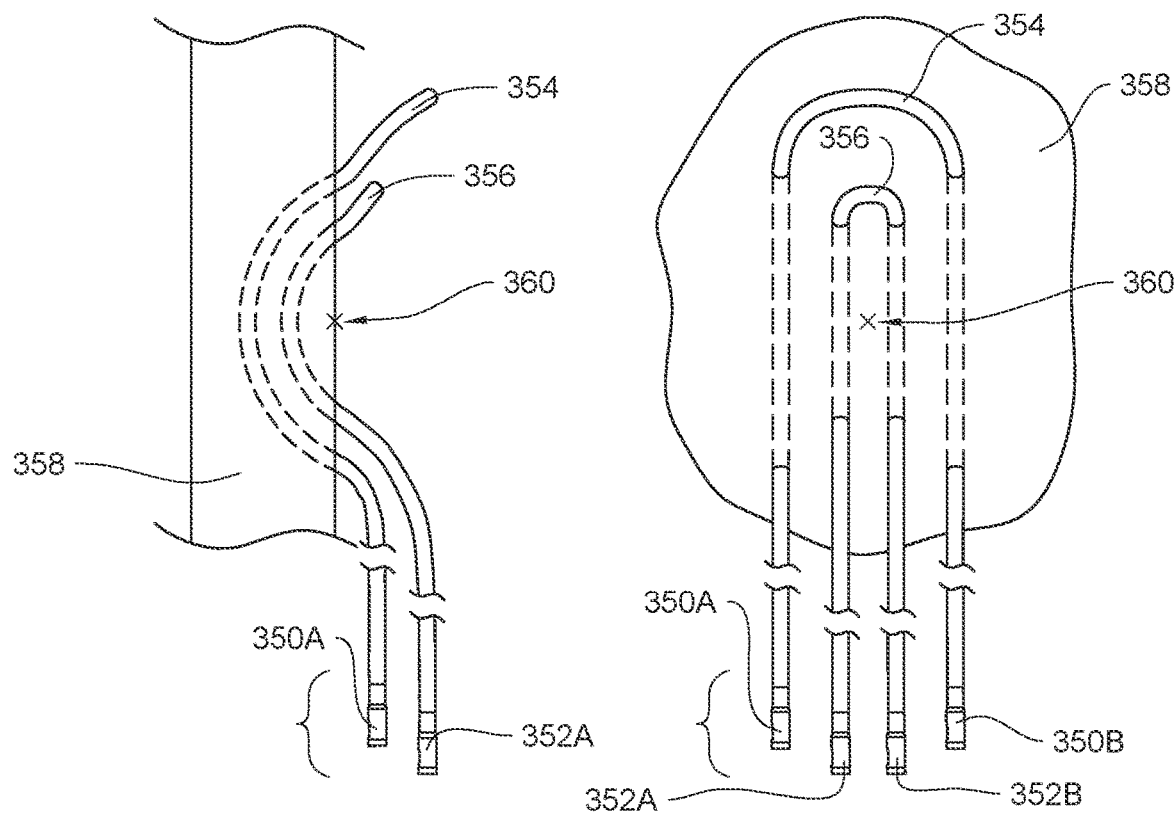

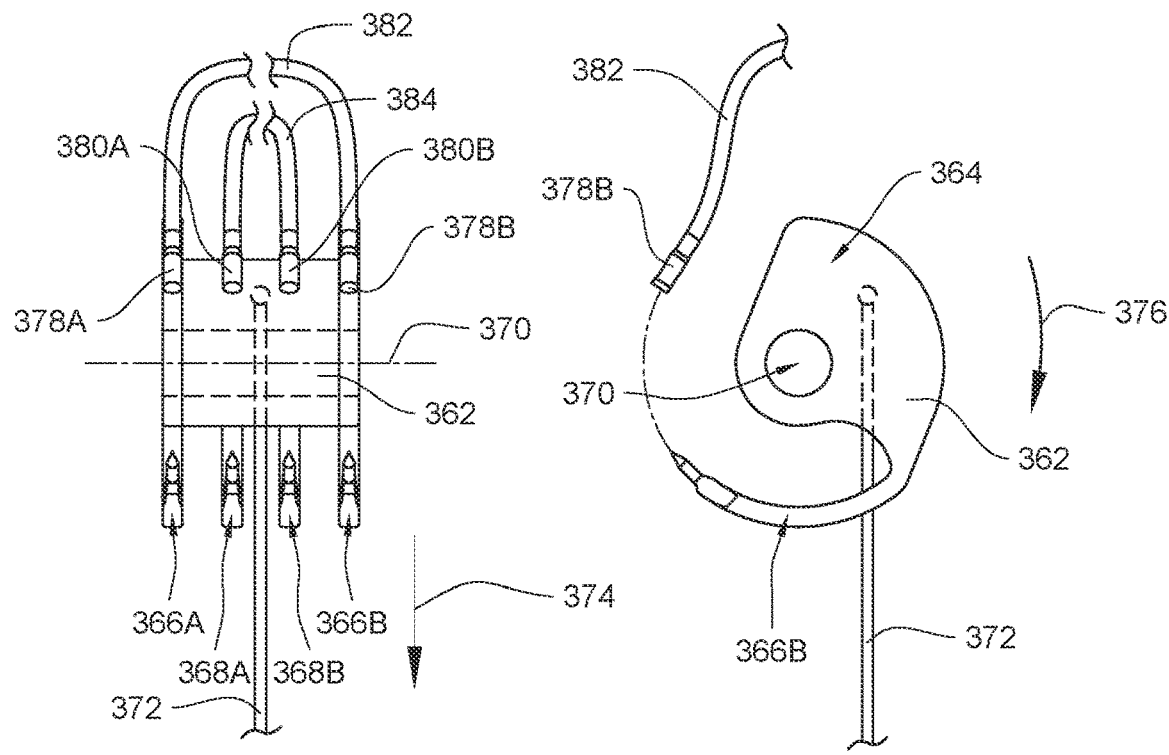
FIG. 22A
FIG. 22B
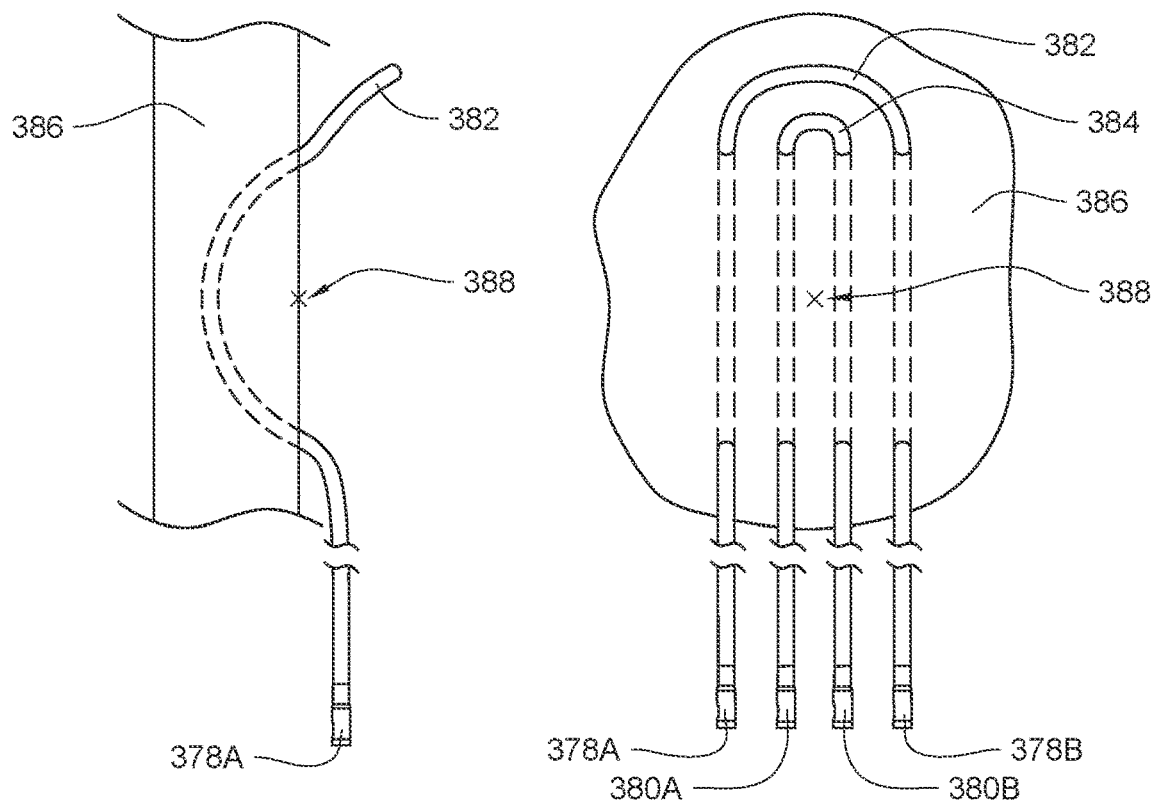
FIG. 23B
FIG. 23A

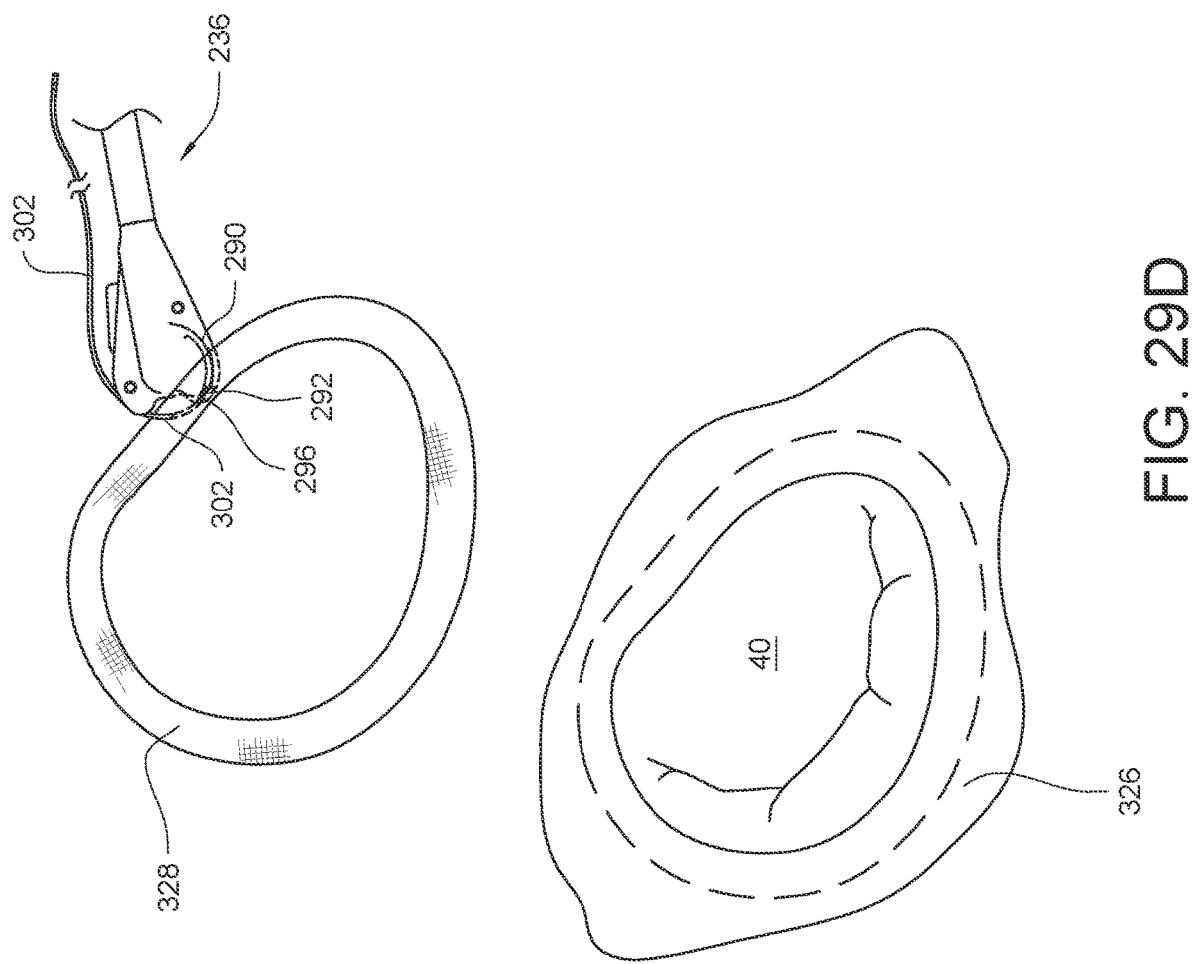

SUTURING DEVICE FOR MINIMALLY INVASIVE SURGERY AND NEEDLES AND METHODS THEREOF

RELATED APPLICATIONS

This patent application is a continuation of U.S. patent application Ser. No. 16/259,666, filed on Jan. 28, 2019, which is a continuation-in-part of U.S. patent application Ser. No. 14/727,235, filed Jun. 1, 2015. U.S. patent application Ser. No. 16/259,666 also claims priority to U.S. Provisional Patent Application No. 62/622,923, filed Jan. 28, 2018. The contents of each of U.S. patent application Ser. No. 16/259,666, U.S. patent application Ser. No. 14/727,235, and U.S. Provisional Patent Application No. 62/622,923 is hereby incorporated by reference in its entirety.

FIELD

The claimed invention relates to surgical suturing, and more specifically to minimally invasive surgical suturing devices, needles, and methods for suturing tissue and prosthetic devices such as, but not limited to, papillary muscles, aortic roots, and annuloplasty rings.

BACKGROUND

The human heart relies on a series of one-way valves to help control the flow of blood through the chambers of the heart. For example, referring to FIG. 1, deoxygenated blood returns to the heart 20, via the superior vena cava 22 and the inferior vena cava 24, entering the right atrium 26. The heart muscle tissue contracts in a rhythmic, coordinated heartbeat, first with an atrial contraction which aids blood in the right atrium 26 to pass through the tricuspid valve 28 and into the right ventricle 30. Following atrial contraction, ventricular contraction occurs and the tricuspid valve 28 closes. Ventricular contraction is stronger than atrial contraction, assisting blood flow through the pulmonic valve 32, out of the heart 20 via the pulmonary artery 34, and to the lungs (not shown) for oxygenation. Following the ventricular contraction, the pulmonic valve 32 closes, preventing the backwards flow of blood from the pulmonary artery 34 into the heart 20.

Oxygenated blood returns to the heart 20, via the pulmonary veins 36, entering the left atrium 38. Left atrial contraction assists blood in the left atrium 38 to pass through the mitral valve 40 and into the left ventricle 42. Following the atrial contraction, ensuing ventricular contraction causes mitral valve 40 closure, and pushes oxygenated blood from the left ventricle 42 through the aortic valve 44 and into the aorta 46 where it then circulates throughout the body. Under nominal conditions, prolapse of mitral valve 40 is prevented during ventricular contraction by chordae 40A attached between the mitral valve 40 leaflets and papillary muscles 40B. Following left ventricular contraction, the aortic valve 44 closes, preventing the backwards flow of blood from the aorta 46 into the heart 20.

Unfortunately, one or more of a person's heart valves 28, 32, 40, and 44 can have or develop problems which adversely affect their function and, consequently, negatively impact the person's health. Generally, problems with heart valves can be organized into two categories: regurgitation and/or stenosis. Regurgitation occurs if a heart valve does not seal tightly, thereby allowing blood to flow back into a chamber rather than advancing through and out of the heart. This can cause the heart to work harder to remain an effective pump. Regurgitation is frequently observed when the mitral valve 40 fails to properly close during a ventricular contraction. Mitral regurgitation can be caused by chordae 40A stretching, tearing, or rupturing, along with other structural changes within the heart.

Neochordal replacement for stretched or torn chordae is one option to reduce regurgitation. In such a procedure, chords to be replaced are identified and dissected as required. A papillary suture is placed in a papillary muscle corresponding to the dissected chord. The papillary suture may optionally be pledgeted on one or both sides of the papillary muscle. A leaflet suture is also placed in the corresponding mitral valve leaflet. The papillary suture and the leaflet suture may then be tied or otherwise fastened together to create a replacement chord to help support the mitral valve leaflet and prevent regurgitation.

Regurgitation with the mitral valve or the aortic valve may also occur when the valve's leaflets are unable to coapt properly. In such a situation, if the leaflets are still viable, surgeons may determine that the improper coaption is caused by changes in the surrounding annulus tissue whereby the annulus has become distorted due to disease or patient genetics/aging. One possible treatment in such situations is a valve annuloplasty, whereby a device (typically a ring) is sutured around the heart valve to help pull the valve leaflets together.

In cases of stenosis, when a heart valve does not fully patent due to stiff or fused leaflets, blood flow tract narrowing, or obstructive material buildup (e.g., calcium), installation of a replacement heart valve may be more appropriate. In these situations, the diseased heart valve may be removed and then a replacement valve may be sutured into the surrounding tissue.

Unfortunately, while many of the above techniques are proven methods of heart valve repair, technical challenges impede their widespread utilization, especially in minimally invasive cardiac surgery. In particular, it is difficult and time consuming to manipulate a suture needle with forceps through a minimally invasive opening to place the sutures for neochordal replacement, valve annuloplasty, or valve replacement. An innovative system that remotely delivers and reliably secures suture for a variety of surgical situations would dramatically improve the accessibility and clinical outcomes following cardiac and other types of surgery.

Therefore, there is a need for an efficient and precise minimally invasive surgical suturing device that enables surgeons to utilize a minimal invasive entry point for cardiac and other procedures without sacrificing suturing effectiveness.

SUMMARY

A suturing device for minimally invasive surgery is disclosed. The suturing device has a head defining one or more ferrule holders and a tissue bite area. The suturing device also has a shaft having a distal end which is coupled to the head, with the tissue bite area facing a direction substantially parallel to a longitudinal axis of the shaft. The suturing device also has a first needle comprising a flywheel portion and one or more curved arms extending from the flywheel portion, each of the one or more curved arms comprising a ferrule engaging tip, wherein the first needle is pivotably coupled to the head. The suturing device further has a first actuator coupled to the first needle and configured to rotate it from a retracted position, where the ferrule engaging tip of each of the one or more curved arms starts away from the one or more ferrule holders, through the tissue bite area, and to an engaged position where the ferrule engaging tip of each of the one or more curved arms is operationally aligned with the one or more ferrule holders.

Another suturing device for minimally invasive surgery is disclosed. The suturing device has a head defining first and second ferrule holders and a tissue bite area. The suturing device also includes a shaft, with the head coupled to the shaft at a distal end of the shaft, the tissue bite area facing a direction substantially parallel to a longitudinal axis of the shaft. The suturing device also has a needle pivotably coupled to the head. The needle includes 1) a flywheel portion, 2) a first curved arm extending from the flywheel portion, the first curved arm comprising a first ferrule engaging tip; and 3) a second curved arm extending from the flywheel portion, the second curved arm comprising a second ferrule engaging tip. The suturing device further includes an actuator comprising a drive link coupled to the needle and configured to rotate it from: 1) a retracted position where the first and second ferrule engaging tips start away from the first and second ferrule holders; 2) then through the tissue bite area; and 3) then to an engaged position where i) the first ferrule engaging tip is operationally aligned with the first ferrule holder; and ii) the second ferrule engaging tip is operationally aligned with the second ferrule holder.

BRIEF DESCRIPTION OF THE DRAWINGS

FIGS. 4A-4F show front, right side, left side, top, bottom, and rear views, respectively, for one embodiment of a needle for a surgical suturing device.

FIGS. 5A-5C illustrate the distal end of the surgical suturing device of FIG. 2 in a partially sectioned perspective view, loaded with a suture, and illustrating the movement of the needle from a retracted position to an engaged position and back to the retracted position.

FIGS. 10A-10F show front, right side, left side, top, bottom, and rear views, respectively, for another embodiment of a needle for a surgical suturing device.

FIGS. 11A-11C illustrate the distal end of the surgical suturing device of FIG. 8 in a partially sectioned perspective view, loaded with a suture, and illustrating the movement of the needle from a retracted position to an engaged position and back to the retracted position.

FIGS. 12A-12C illustrate the distal end of the surgical suturing device of FIG. 8 in a partially sectioned side view, loaded with a suture, and illustrating the movement of the needle from a retracted position to an engaged position and back to the retracted position.

FIGS. 16A-16F show front, right side, left side, top, bottom, and rear views, respectively, for a further embodiment of a needle for a surgical suturing device.

FIGS. 19I-19J illustrate a method of coupling a first suture and then multiple sutures placed in an annuloplasty ring and underlying tissue to the ring as part of an annuloplasty.

FIGS. 20A and 20B schematically illustrate another embodiment of a surgical suturing device in top and side views, respectively, this embodiment having a needle with multiple pairs of curved arms, each pair of curved arms following a path having a different radius.

FIGS. 21A and 21B schematically illustrate a resultant placement of sutures in tissue from the surgical suturing device of FIGS. 20A and 20B.

FIGS. 22A and 22B schematically illustrate a further embodiment of a surgical suturing device in top and side views, respectively, this embodiment having a needle with multiple pairs of curved arms, each pair of curved arms following paths having substantially the same radius.

FIGS. 23A and 23B schematically illustrate a resultant placement of sutures in tissue from the surgical suturing device of FIGS. 22A and 22B.

Figure 1:
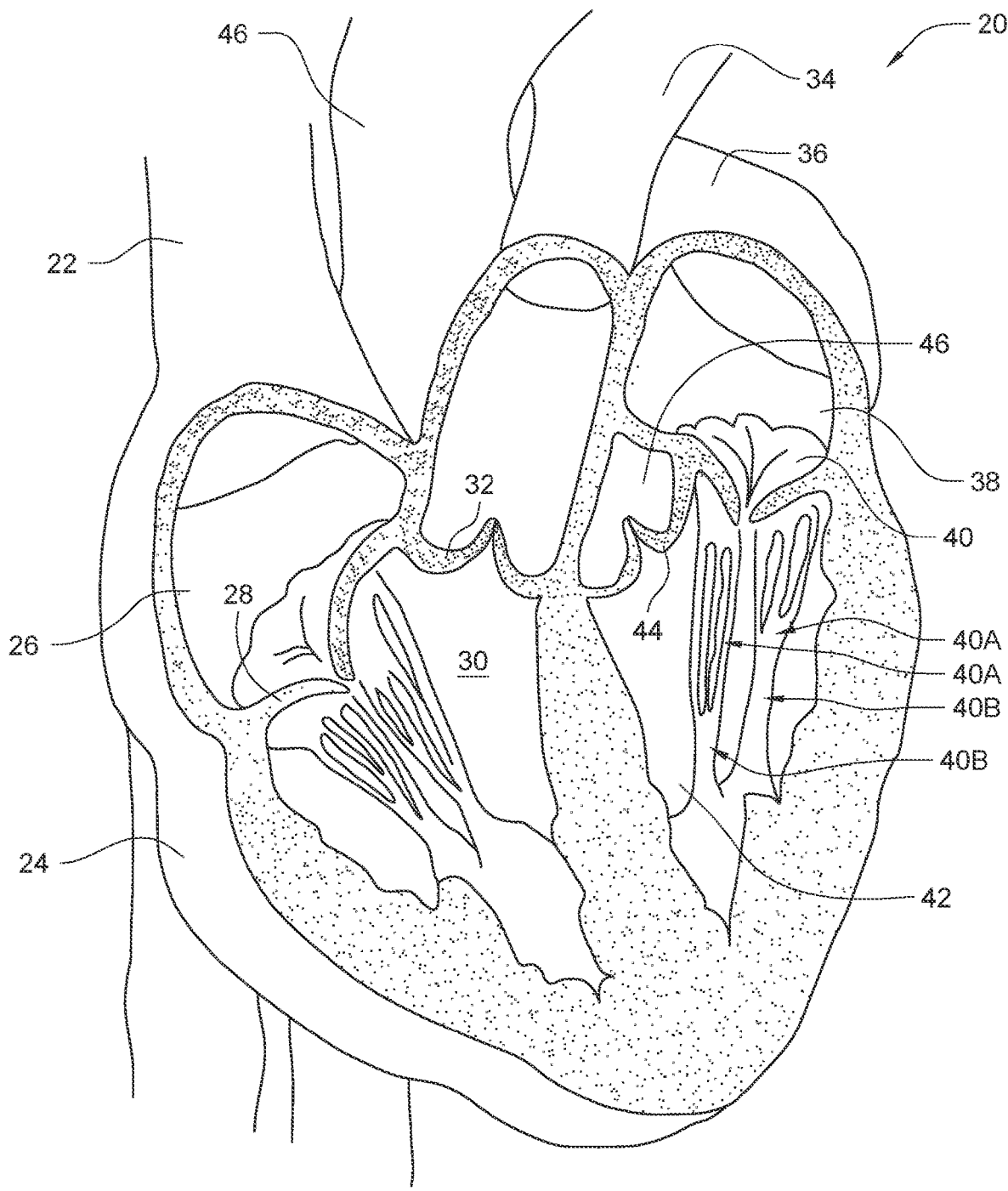
FIG. 1 is a cross-sectional view of a heart, illustrating the chambers and valves which function therein.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 2:
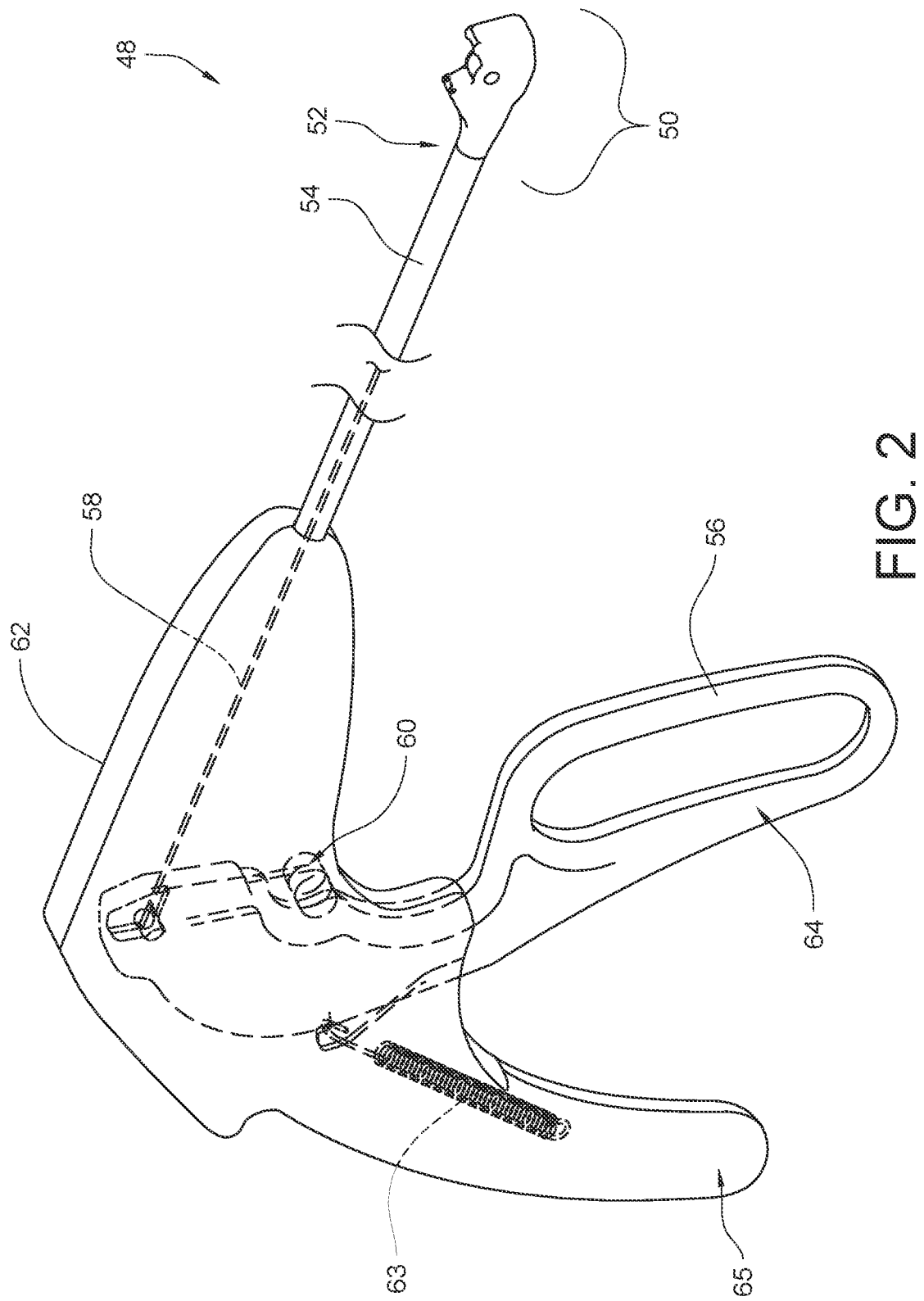
FIG. 2 is a perspective view of one embodiment of a surgical suturing device.

FIG. 2 is a perspective view of one embodiment of a surgical suturing device 48. The surgical suturing device 48 has a device tip 50 which is located at a distal end 52 of a shaft 54 and which will be discussed in more detail below. The surgical suturing device 48 also has an actuator 56 which is coupled to an actuator rod 58. The actuator 56 has an actuator pivot point 60 supported by a housing 62. An actuator spring 63 is coupled between the actuator 56 and the housing 62 to bias the actuator 56 into a retracted position, such as the position shown in FIG. 2. In this embodiment, a handle 64 of the actuator 56 is configured to be moved from the retracted position of FIG. 2 to an engaged position where the actuator 56 is pivoted around the pivot point 60 to move the handle 64 closer to a grip 65 of the housing 64. Since the pivot point 60 is between the handle 64 and the point where the actuator rod 58 couples to the actuator 56 in this embodiment, the actuator rod 58 will move distally, toward the device tip 50 when the handle 64 is squeezed towards the grip 65. Conversely, in this embodiment, the actuator rod 58 will move proximally, toward the housing 62, when the handle 64 is moved away from the grip 65. Although the actuator 56 in this embodiment includes a lever, other embodiments may utilize a variety of other actuators, including, but not limited to, a control knob, a control wheel, a solenoid, a slider, a screw, one or more gears, one or more pulleys, a motor, or any plurality and/or combination thereof.

Figure 3:
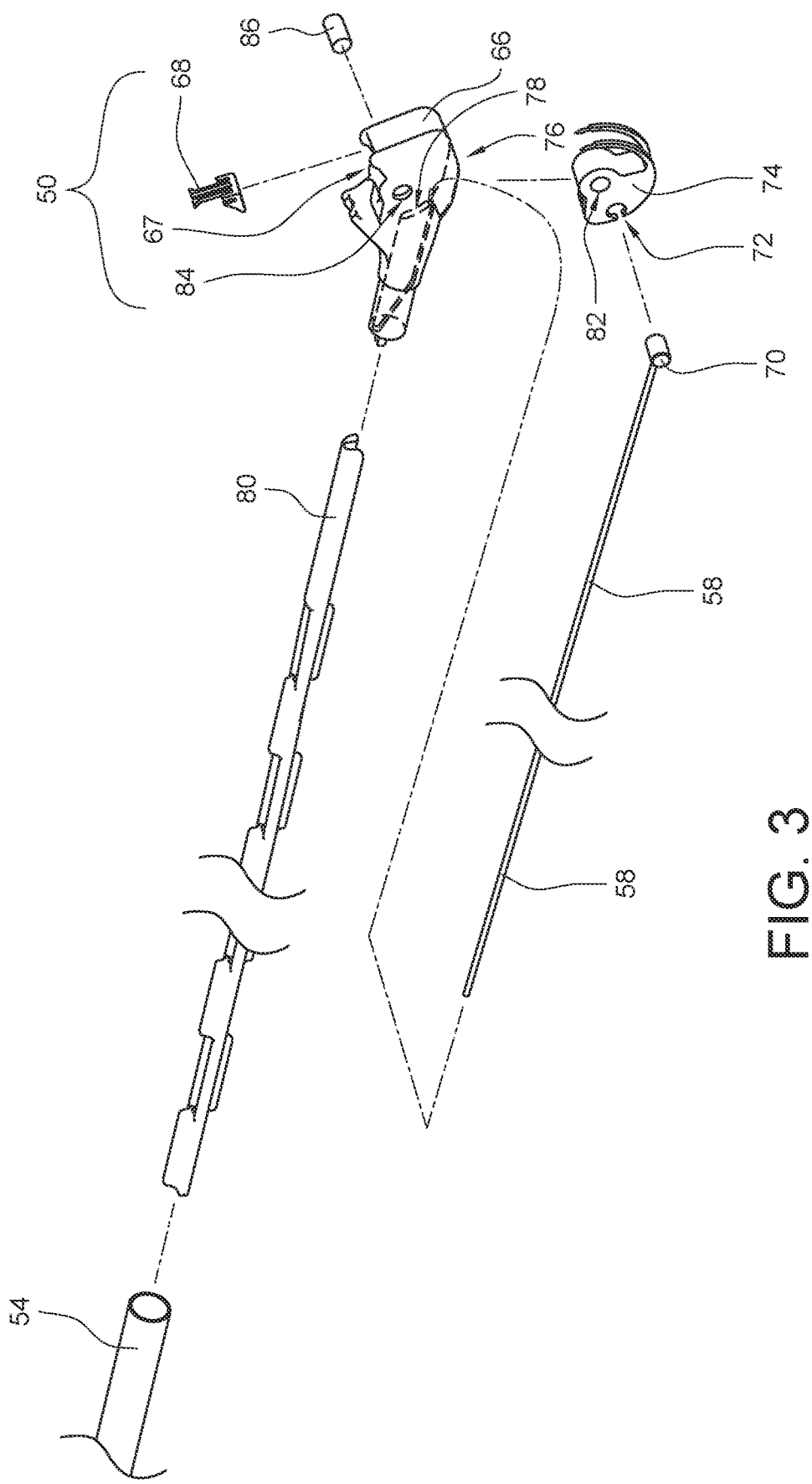
FIG. 3 is an exploded perspective view of the embodied surgical suturing device of FIG. 2 without the housing or needle actuator.

FIG. 3 is an exploded perspective view of the embodied surgical suturing device of FIG. 2 without the housing or needle actuator. The device tip 50 includes a head 66 having a first opening 67 through which a ferrule release feature 68 may be inserted. The actuator rod 58 has an actuator end effector 70 coupled to a distal end of the actuator rod 58. The actuator end effector 70 may be inserted into an actuator coupler 72 defined by a needle 74. The needle 74 may be inserted into a needle access hole 76 in a side of the head 66 opposite the first opening 67, while the actuator rod 58 may be positioned within an actuator access channel 78 also defined by the head 66. The actuator rod 58 will extend out of the head 66 and can be fitted within an actuator rod guide 80 which fits within the shaft 54. Other embodiments may forego an actuator rod guide 80, and may instead just use the shaft 54 to contain the actuator rod 58. The head 66 couples to the shaft 54.

The needle 74 also defines a needle pivot axis 82 which may be aligned with one or more holes 84 in the head 66. The needle pivot axis 82 may be kept in alignment with the one or more holes 84 by a pivot pin 86 which can be inserted into the one or more holes 84 and the needle pivot axis 82. The exploded assembly of the embodiment in FIG. 3 is just one of many possible assemblies, and it should be understood that those skilled in the art will realize other assembly configurations and methods of assembly which can produce the claimed surgical suturing device and its equivalents. Such assembly methods and their equivalents are intended to be included in the scope of this disclosure.

FIGS. 4A-4F show front, right side, left side, top, bottom, and rear views, respectively, for one embodiment of a needle 74 for a surgical suturing device. As noted earlier, in this embodiment, the needle 74 defines an actuator coupler 72 and a needle pivot axis 82. In this embodiment, the needle pivot axis 82 is a cylindrical channel in the needle through which an axle pin may be inserted. In other embodiments, the needle pivot axis 82 may be defined by protrusions on one or more side of the needle 74. The needle 74 also has a flywheel portion 87 which will be discussed in more detail below.

In this embodiment, the needle 74 has first and second curved arms 88 and 92 extending from the flywheel portion 87. The first curved arm 88 has a first ferrule engaging tip 90 at an end of the first curved arm 88 away from the flywheel portion 87. Likewise, the second curved arm 92 has a second ferrule engaging tip 94 at an end of the second curved arm 92 away from the flywheel portion 87. The first and second ferrule engaging tips 90, 94 and their respective curved arms 88, 92 are configured to be able to pierce tissue as the needle 74 is rotated about the needle pivot axis 82. The first and second ferrule engaging tips 90, 94 are each further configured to releasably engage a ferrule attached to suture (not shown here, as the needle does not include any ferrules).

In this embodiment, the first and second curved arms 88, 92 each extend from the flywheel portion 87 on substantially identical arcs following substantially parallel paths. Furthermore, in this embodiment, the first and second curved arms 88, 92 each have a respective arc centerpoint which falls on the needle pivot axis 82. Also, in this embodiment, each of the first and second curved arms 88, 92 has a substantially square cross-section. Other embodiments may have other cross-sectional shapes, including, but not limited to substantially round cross-sections or substantially triangular cross-sections.

In this embodiment, the first curved arm 88, of needle 74, also includes a first release ramp 96 adjacent to the first ferrule engaging tip 90. Similarly, the second curved arm 92 also includes a second release ramp 98 adjacent to the second ferrule engaging tip 94. The first and second release ramps 96, 98 enable a portion of a ferrule release feature (not shown here, since it is not part of the needle) to be biased against the first and second curved arms 88, 92, and depending on a rotational position of the needle 74, the ferrule release feature can ride up the first and second release ramps 96, 98 to push a ferrule off of each of the first and second ferrule engaging tips 90, 94.

As noted above, the flywheel portion 87 defines an actuator coupler 72. In this embodiment, the actuator coupler 72 is accessible in a first direction, parallel to the pivot axis 82 of the needle 74. This access to the actuator coupler 72 in the first direction may be seen in the views of FIGS. 4A and 4F. The actuator coupler 72 is also accessible in a second direction, perpendicular to the pivot axis 82 of the needle 74. In this embodiment, the flywheel portion 87 also defines an actuator access slot 100 which also facilitates access to the actuator coupler 72 in the second direction. Access to the actuator coupler 72 may be important in some embodiments so that the actuator end effector on the actuator rod (neither item shown here, since they are not part of the needle) may be coupled to the needle 74 and so that the actuator (via the actuator rod in this example) can rotate the needle 74.

The needle 74 may be made from a variety of materials, including, but not limited to one or more metals, alloys, plastics, polymers, types of glass, ceramics, silicon, and any combination and/or plurality thereof. The flywheel portion 87 of the needle 74 adds mass to the needle to help ensure a smooth rotational needle movement and to help control the orientation of the needle as it moves through tissue by stabilizing the needle 74 against one or more inside surfaces of the device head. In many embodiments, the mass of the flywheel portion 87 may be greater than or equal to the mass of the one or more curved arms 88, 92 of the needle 74. In other embodiments, the mass of the flywheel portion 87 may be less than the mass of the one or more curved arms 88, 92 of the needle 74. Without being tied to one specific theory, the mass of the flywheel portion 87 can also eliminate the need for a guide for the curved arms 88, 92 since the needle 74 may be stabilized by the mass and dimensions of the flywheel portion 87. As can be seen in the views of FIGS. 4A and 4F, the flywheel portion 87 sweeps across an arc of approximately ninety degrees in addition to helping define the needle pivot axis 82. Other embodiments may include one or more arc sweeps of lesser, greater, or similar size. As can be seen in the views of FIGS. 4B, 4C, 4D, and 4E, the flywheel portion 87 also has a width which reaches between the two curved arms 88, 92. In other embodiments, the flywheel portion may have thinner or wider widths. The flywheel portion 87 may also include a tissue-engaging portion as will be discussed in the examples below.

Figure 6A:
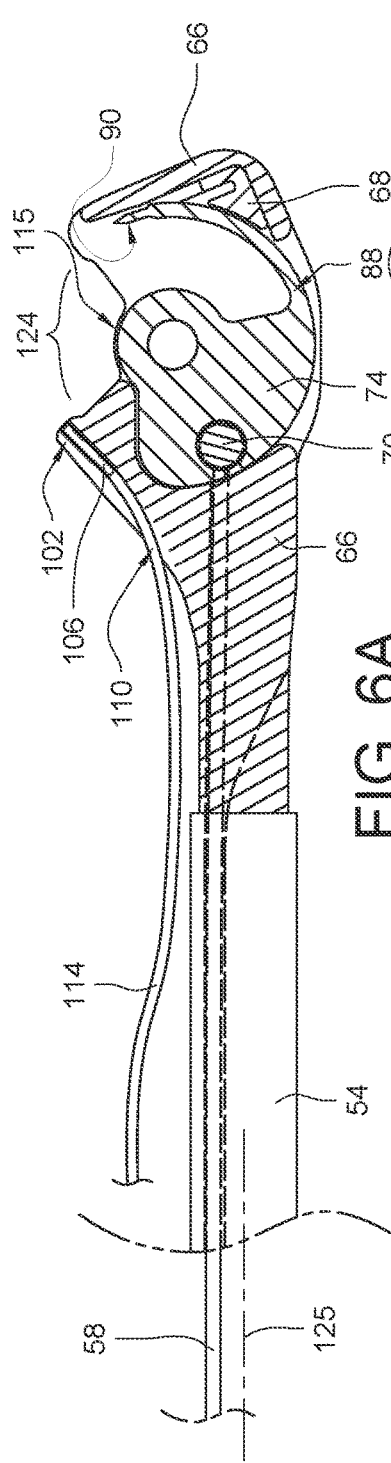
FIGS. 6A-6C illustrate the distal end of the surgical suturing device of FIG. 2 in a partially sectioned side view, loaded with a suture, and illustrating the movement of the needle from a retracted position to an engaged position and back to the retracted position.

FIGS. 5A-5C show the distal end of the surgical suturing device of FIG. 2 in a partially sectioned perspective view, illustrating the movement of the needle 74. FIG. 5A corresponds to FIG. 6A, FIG. 5B corresponds to FIG. 6B, and FIG. 5C corresponds to FIG. 6C. In FIG. 5A, the needle 74 is shown in a retracted position, where the first ferrule engaging tip 90 and the second ferrule engaging tip (not visible in this view) start away from their respective first and second ferrule holders 102, 104. The ferrule holders 102, 104 are either formed from or coupled to the device head 66. A first ferrule 106 and a second ferrule 108 are each installed in and held by respective first and second ferrule holders 102, 104. The first ferrule 106 is coupled to a first end 110 of a suture 114, while the second ferrule 108 is coupled to a second end 112 of the suture 114. The suture 114 may be of a variety of lengths, and for convenience the portion of the suture 114 where it loops back on itself is not shown. It should be understood that the term "suture", as used herein, is intended to cover any thread, cable, wire, filament, strand, line, yarn, gut, or similar structure, whether natural and/or synthetic, in monofilament, composite filament, or multi-filament form (whether braided, woven, twisted, or otherwise held together), as well as equivalents, substitutions, combinations, and pluralities thereof for such materials and structures.

The head 66, along with a tissue engaging surface 115 of the flywheel portion of the needle 74, defines a tissue bite area 124. In this embodiment, as can be better seen in FIG. 6A, the tissue bite area 124 faces a direction which is substantially perpendicular to a longitudinal axis 125 of the shaft 54.

Figure 6B:
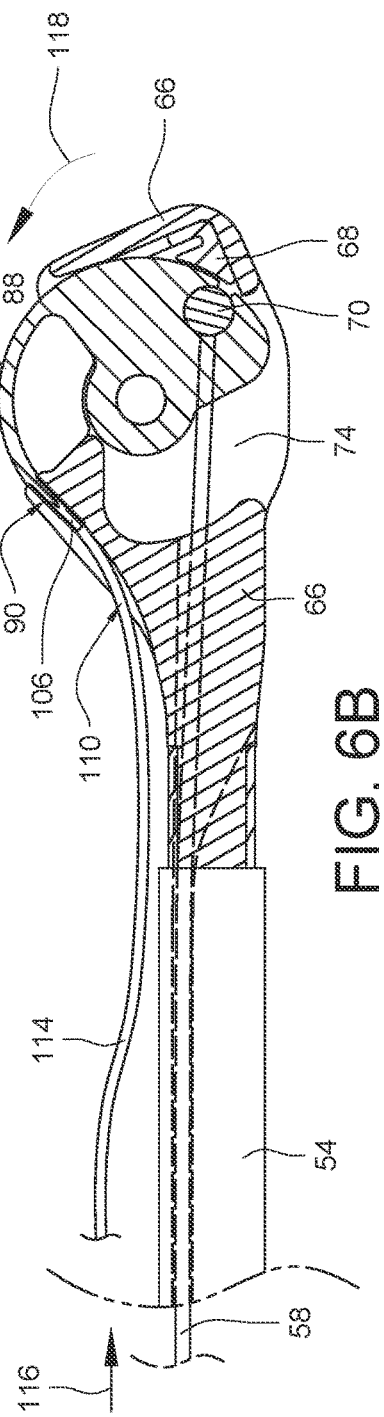

As shown in FIGS. 5B and 6B, the actuator rod 58 may be moved in a distal direction 116, which will cause the needle 74 to rotate in a first direction 118 about its needle pivot axis. While rotating in this first direction 118, the ferrule engaging tips 90, 94 of the curved arms 88, 92 pass from their retracted position (shown in FIGS. 5A, 6A), through the tissue bite area 124, and to an engaged position (shown in FIGS. 5B, 6B). In this embodiment, the ferrule engaging tips 90, 94 move along an arcuate path from a distal end of the head 66 towards a proximal side of the head 66. In the engaged position of FIGS. 5B, 6B, the ferrule engaging tips 90, 94 are each coupled to corresponding ferrules 106, 108 by an interference fit or alternate attachment mechanism, the choice of which is known to those skilled in the art. This coupling of the ferrule engaging tips 90, 94 with the corresponding ferrules 106, 108 may be referred to as operational alignment.

Figure 6C:
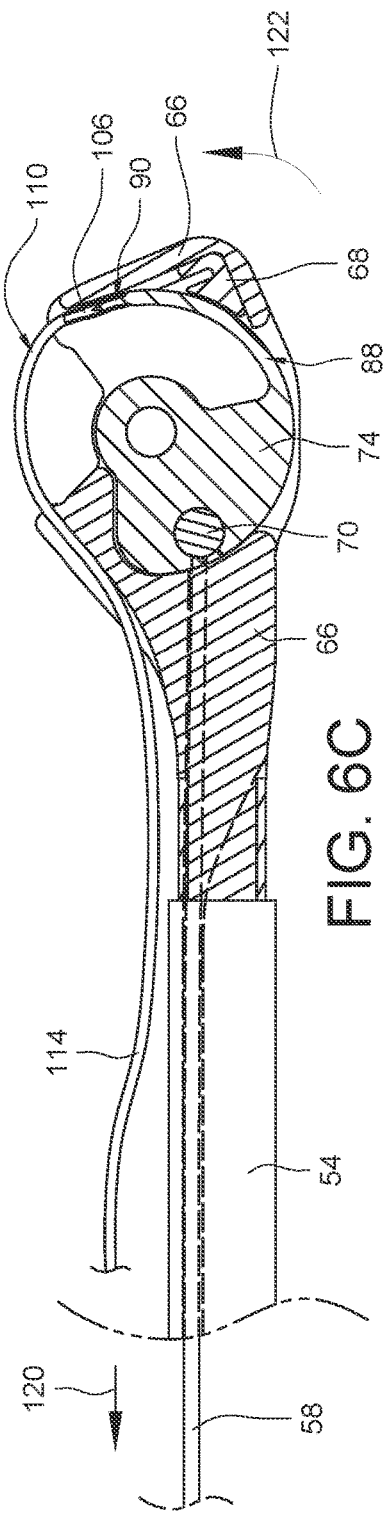

As shown in FIGS. 5C and 6C, the actuator rod 58 may be moved in a proximal direction 120, which will cause the needle 74 to rotate in a second direction 122 (opposite the first direction 118) about its needle pivot axis. While rotating in this second direction 122, the ferrule engaging tips 90, 94 of the curved arms 88, 92 (and the ferrules 106, 108 which are coupled to them) pass from their engaged position (shown in FIGS. 5B and 6B), back through the tissue bite area 124, and to the retracted position as shown in FIGS. 5C and 6C. In this embodiment, while moving back to the retracted position, the ferrule engaging tips 90, 94 move along an arcuate path from the proximal side of the head 66 to the distal side of the head 66. Depending on the embodiment, if a ferrule release feature 68 is present in the device, the ferrule release feature 68 may have elements which are positioned to ride against the curved arms, up the release ramps of the curved arms, and against the ferrules 106, 108 to remove the ferrules 106, 108 from the ferrule engaging tips 90, 94 when the tips 90, 94 return to the retracted position. In other embodiments, the actuator 58 may be configured to selectively rotate the needle past the retracted position, away from the engaged position, when desired in order to then force the captured ferrules to engage the ferrule release feature 68. Some embodiments may not include a ferrule release feature at all.

Figure 7A:
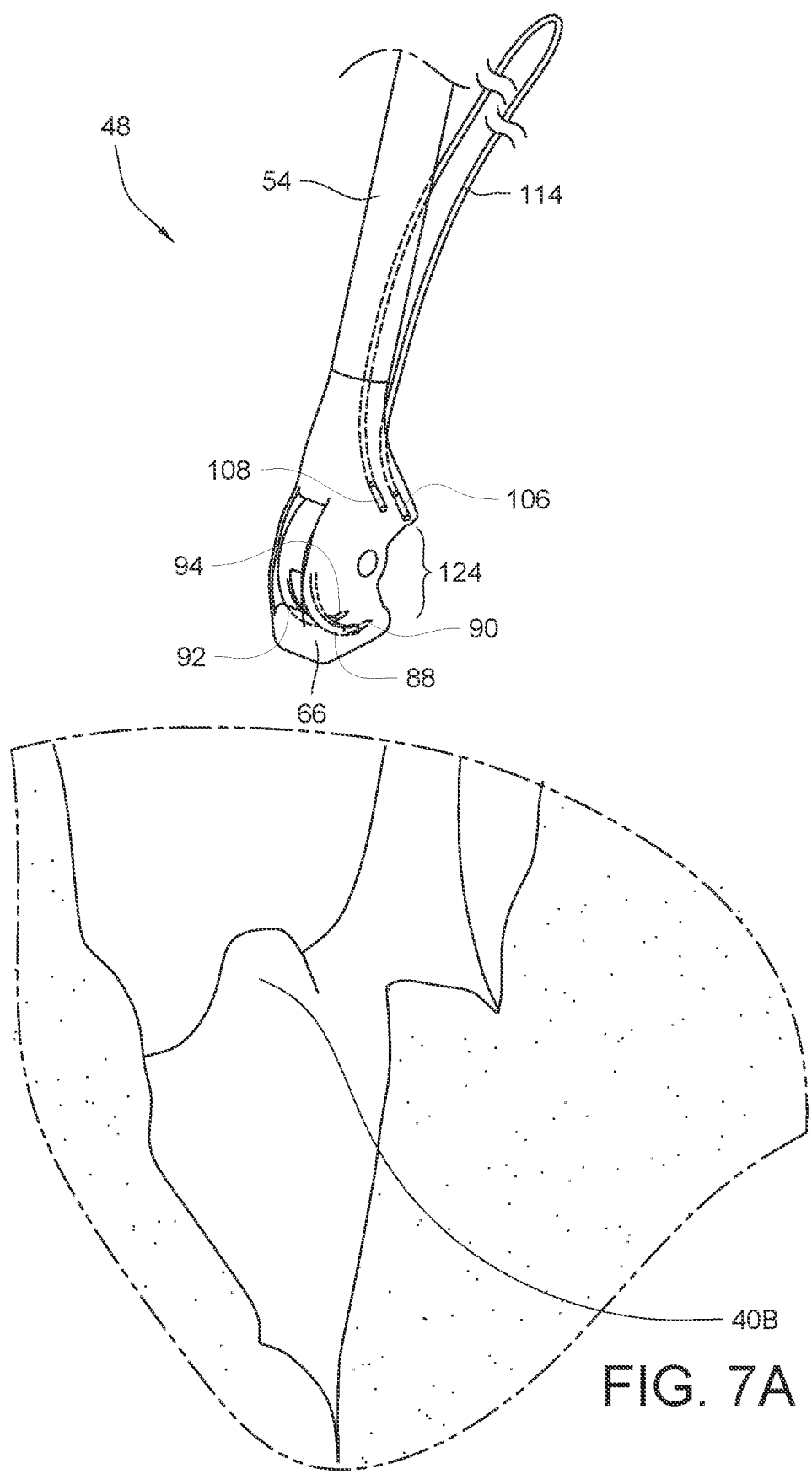
FIGS. 7A-7E illustrate a method of using an embodiment of the surgical suturing device from FIG. 2 to place a suture in a papillary muscle.

FIGS. 7A-7E illustrate a method of using an embodiment of the surgical suturing device from FIG. 2 to place a suture in a papillary muscle 40B. FIG. 7A schematically illustrates a surgical situation. Minimally invasive access has been gained to the left ventricle of the heart. A pathologic chord has been removed from the illustrated papillary muscle 40B, and the suturing device 48 is ready to be used. For convenience, the handle, actuator, and entire shaft are not shown in these views. As before, the device 48 has a tissue bite area 124 defined at least in part by the head 66 at the end of the shaft 54. First and second ferrules 106, 108, coupled to the ends of suture 114 are held in ferrule holders on the proximal side of the tissue bite area 124 in the device head 66. The first and second curved arms 88, 92 and their respective first and second ferrule engaging tips 90, 94 are in a retracted position on the distal side of the tissue bite area 124.

Figure 7B:
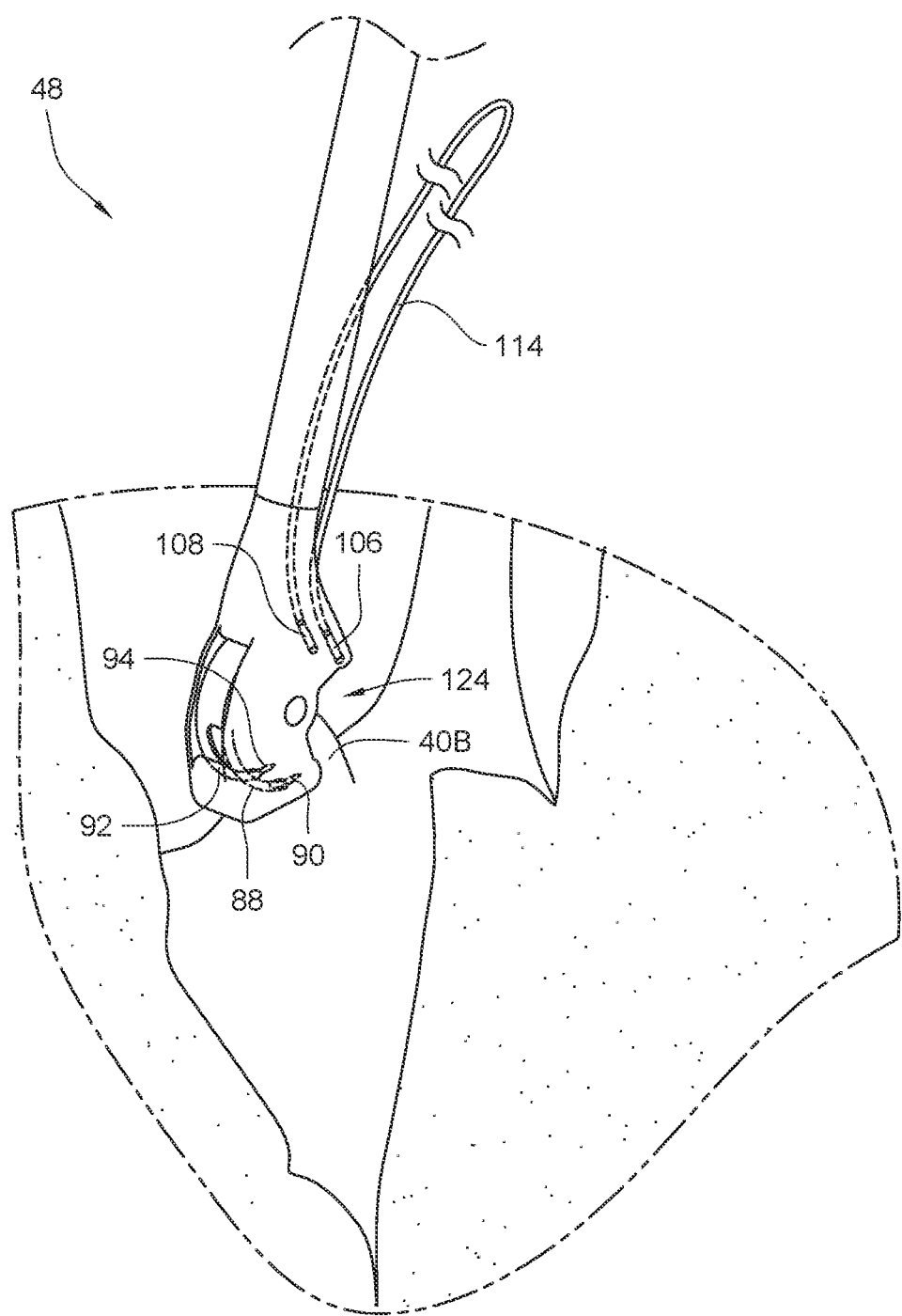
Figure 7C:
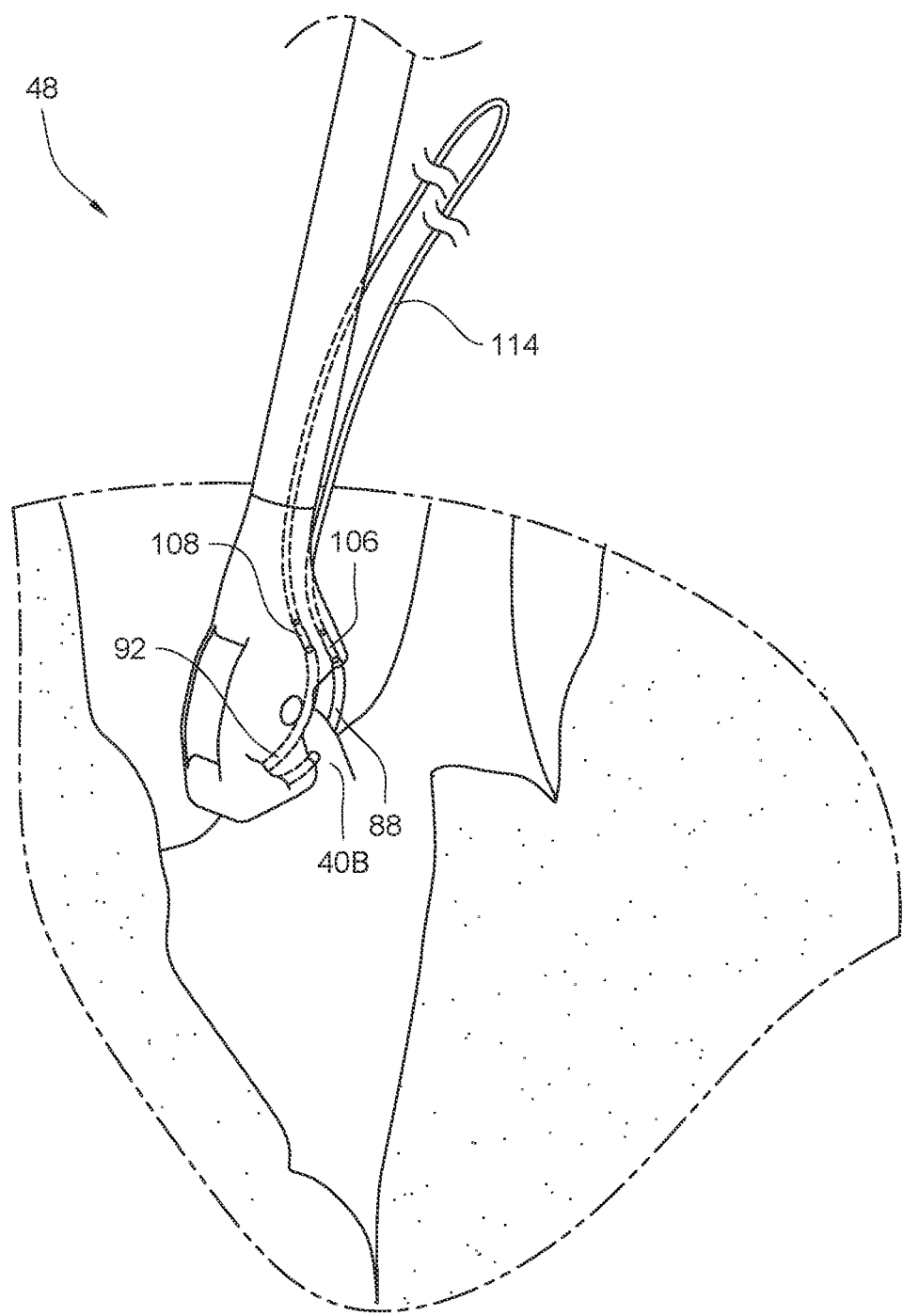
Figure 7D:
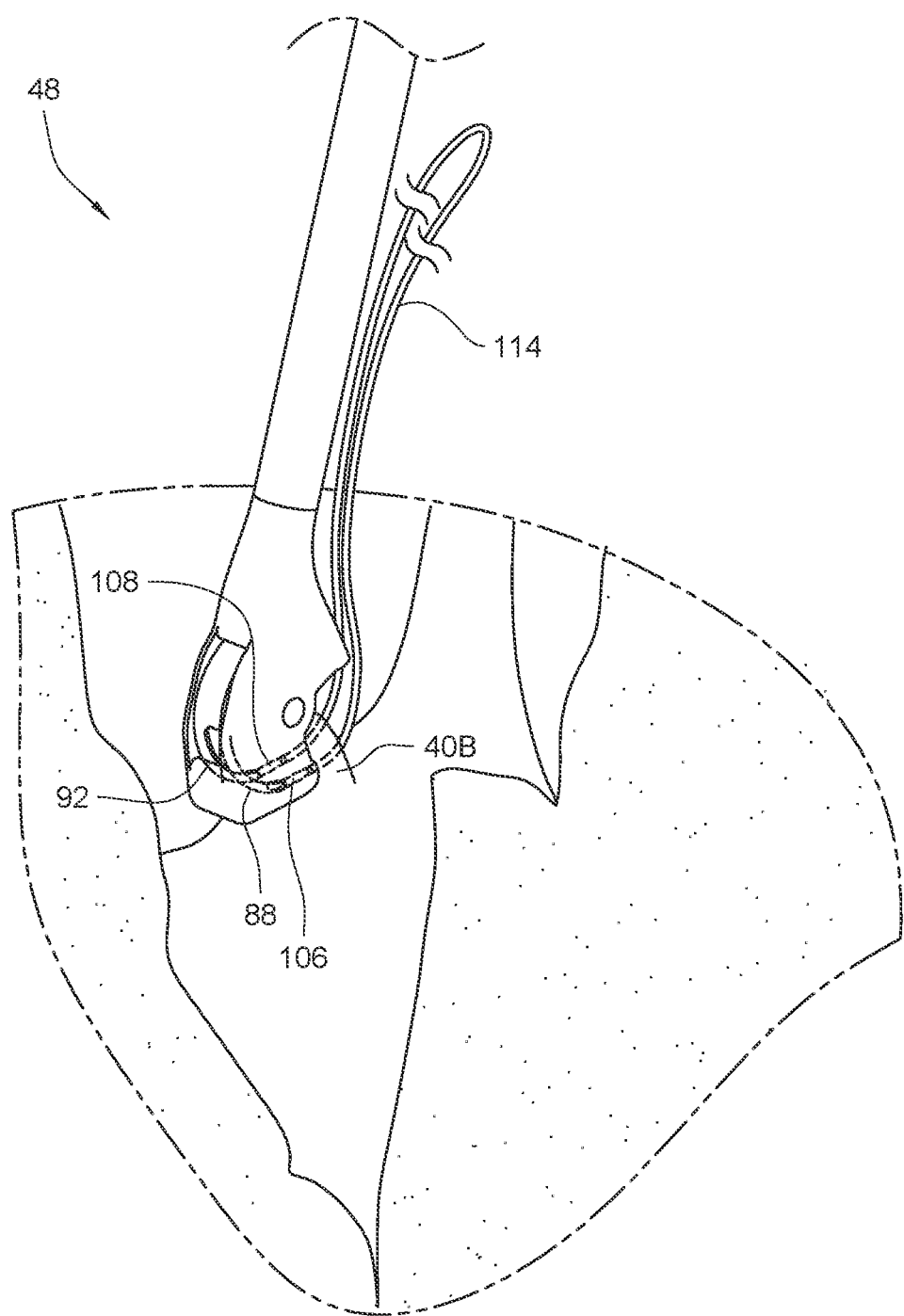
Figure 7E:
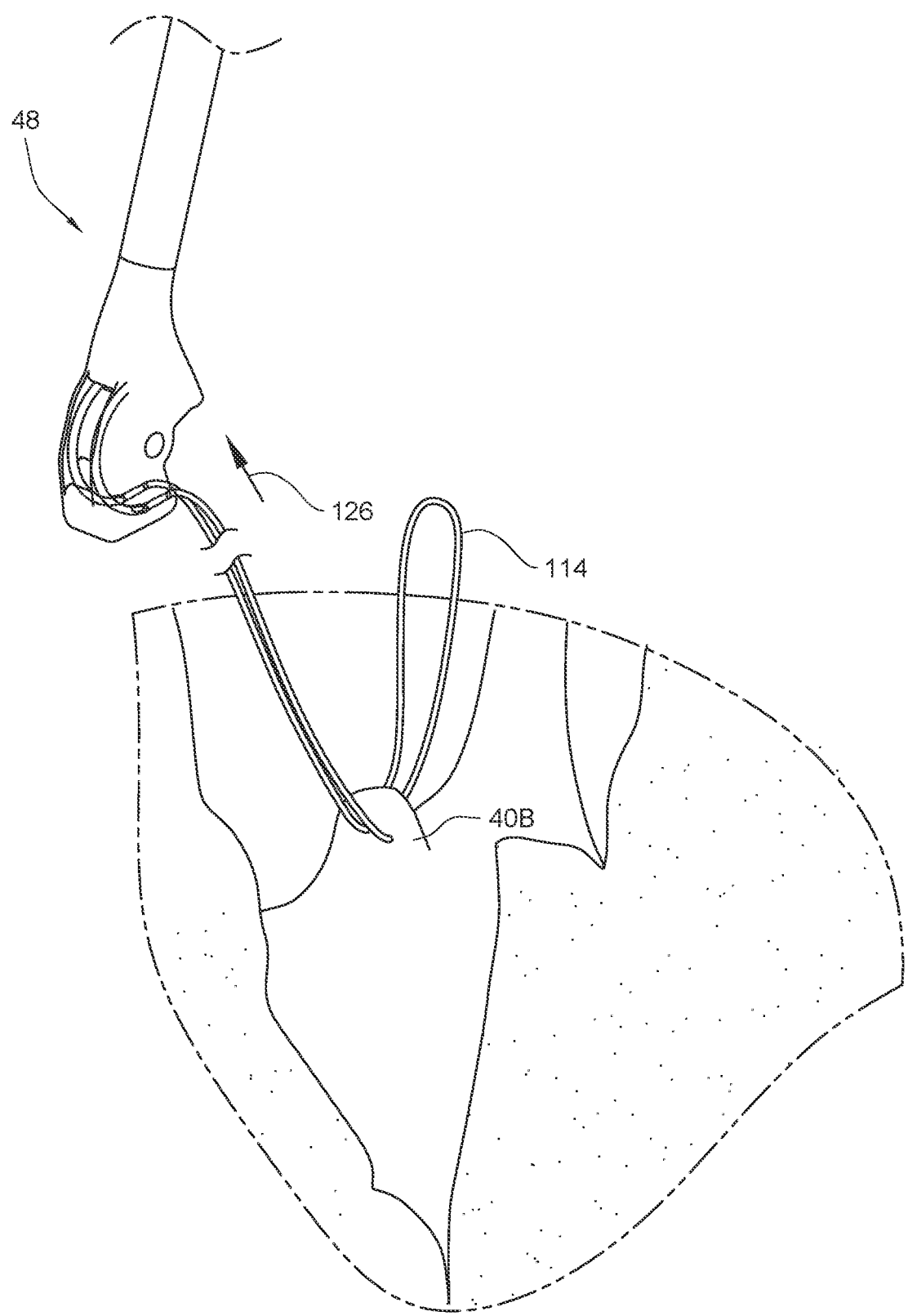

As shown in FIG. 7B, the tissue bite area 124 is placed over the papillary muscle 40B. As shown in FIG. 7C, the needle is actuated so that the first and second curved arms 88, 92, and their respective ferrule engaging tips, pass through the papillary muscle in the tissue bite area and engage the corresponding first and second ferrules 106, 108. As shown in FIG. 7D, the needle is actuated so that the first and second curved arms 88, 92 and their respective ferrule engaging tips and the respective ferrules 106, 108 held by those ferrule engaging tips are pulled back through the tissue 40B in the tissue bite area and into a retracted position again. Since the ends of suture 114 are coupled to the ferrules 106, 108, the suture 114 is also pulled through the papillary muscle 40B. As illustrated in FIG. 7E, the suturing device 48 may be pulled away 126 from the papillary muscle 40B in order to take up the slack in the suture 114. Although this embodiment does not illustrate the use of a pledget on the suture 114, other embodiments may include a pledget which was pre-installed on the suture 114. The ferrules 106, 108 may be removed from the suture.

Figure 7F:
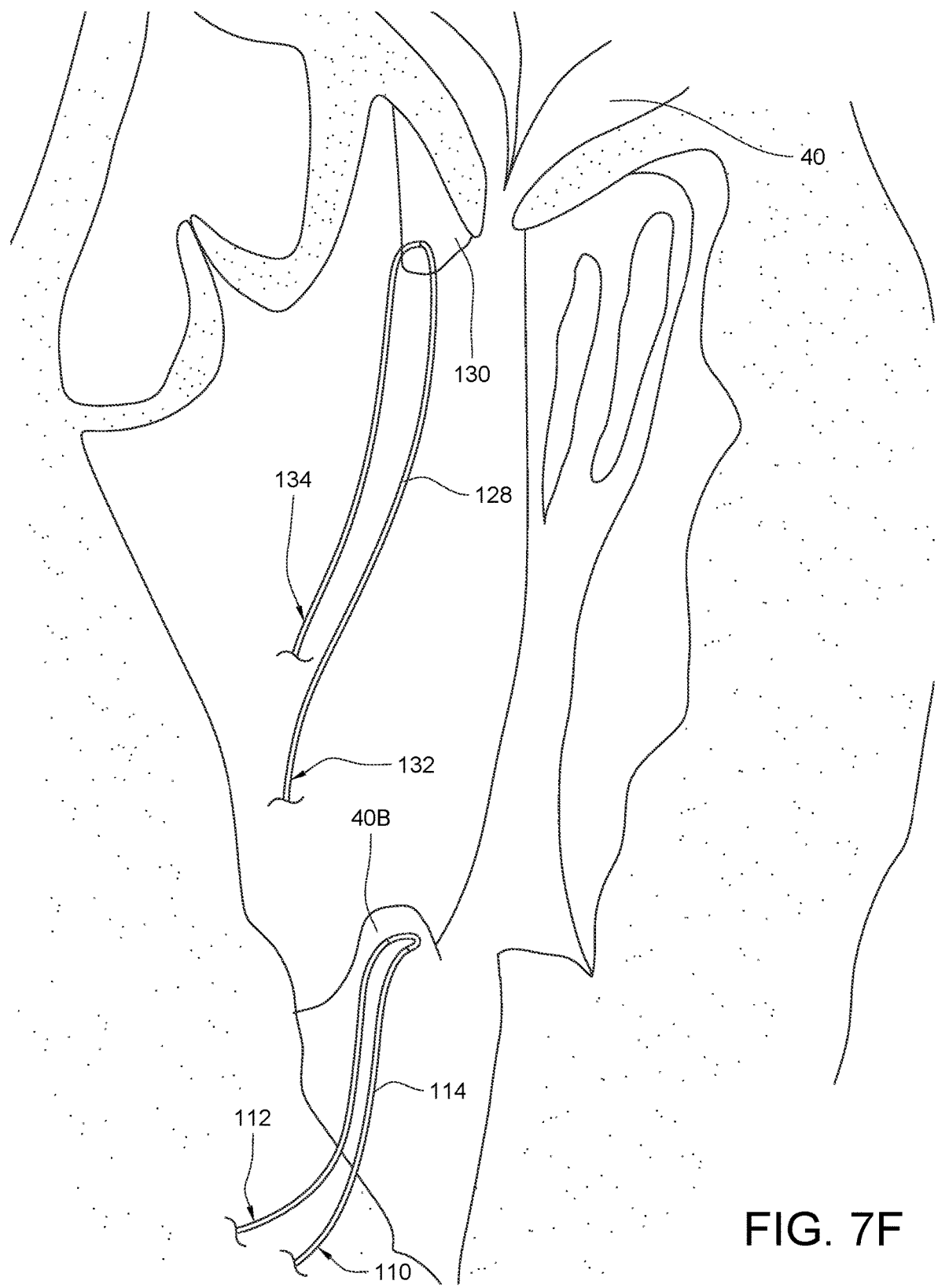
FIGS. 7F-7G illustrate a method of coupling a first suture placed in a papillary muscle and a second suture placed in a valve leaflet to each other using a mechanical fastener to replace a chordae tendinae of the heart.
Figure 7G:
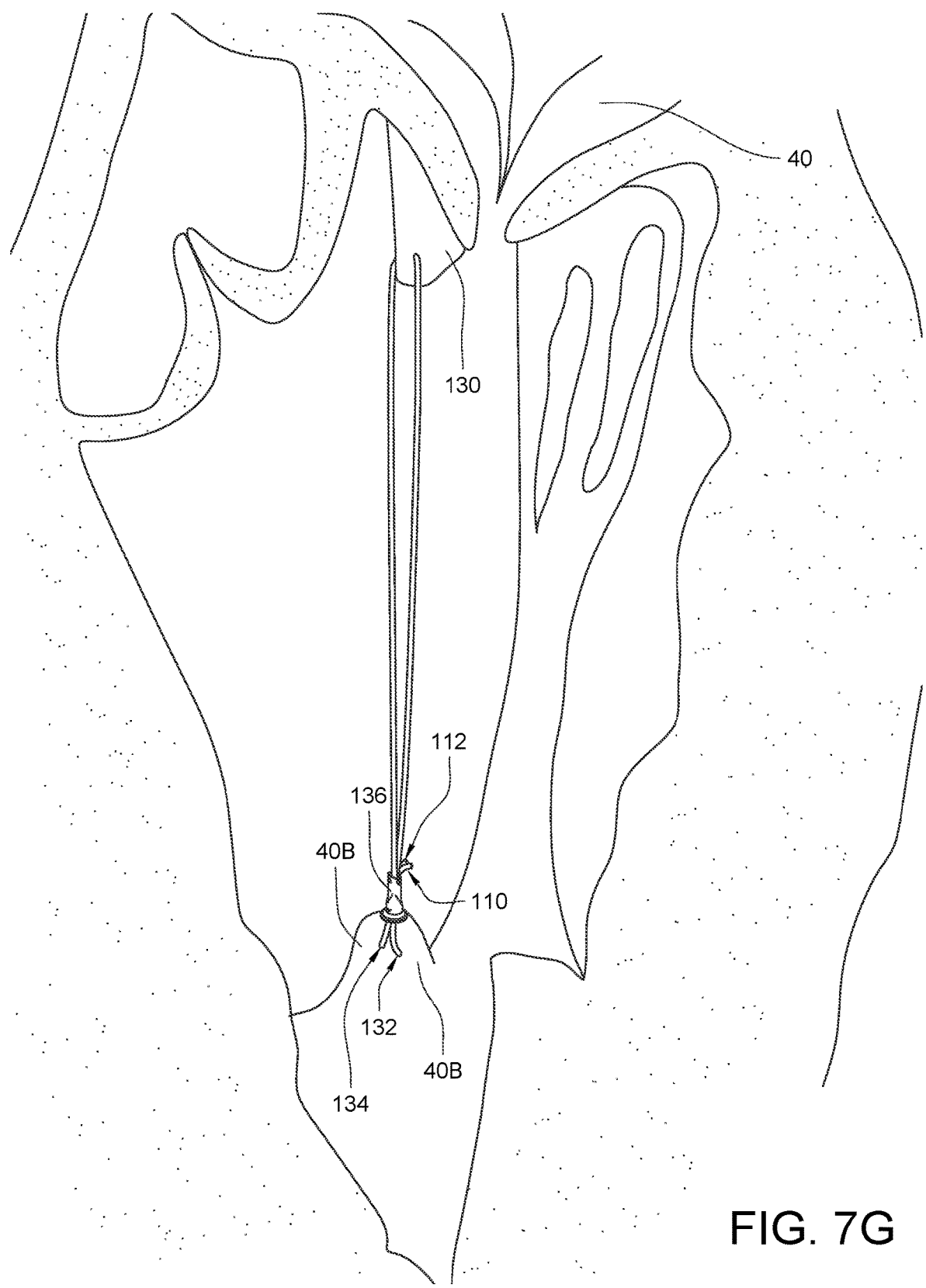

FIGS. 7F-7G illustrate a method of coupling a first suture 114 placed in a papillary muscle 40B and a second suture 128 placed in a valve leaflet 130 to each other using a mechanical fastener 136 to replace a chordae tendinae of the heart. FIG. 7F simply shows the second suture 128 after it has been stitched through a leaflet 130 of the mitral valve 40. Those skilled in the art will be familiar with a variety of ways to create this stitch of the second suture 128. FIG. 7G illustrates a mechanical fastener 136 which has been fastened to hold a first set of suture ends 110, 112 of the first suture 114 which have been passed up through the mechanical faster 136. The mechanical fastener 136 also holds a second set of suture ends 132, 134 of the second suture 128 which have been passed down through the mechanical fastener 136. One suitable method for fastening the two sets of suture ends together in this fashion is disclosed in U.S. Patent Application Publication 2014/0276979, published Sep. 18, 2014 for U.S. patent application Ser. No. 13/840,481 filed Mar. 15, 2013, the entirety of which is hereby incorporated by reference.

Figure 8:
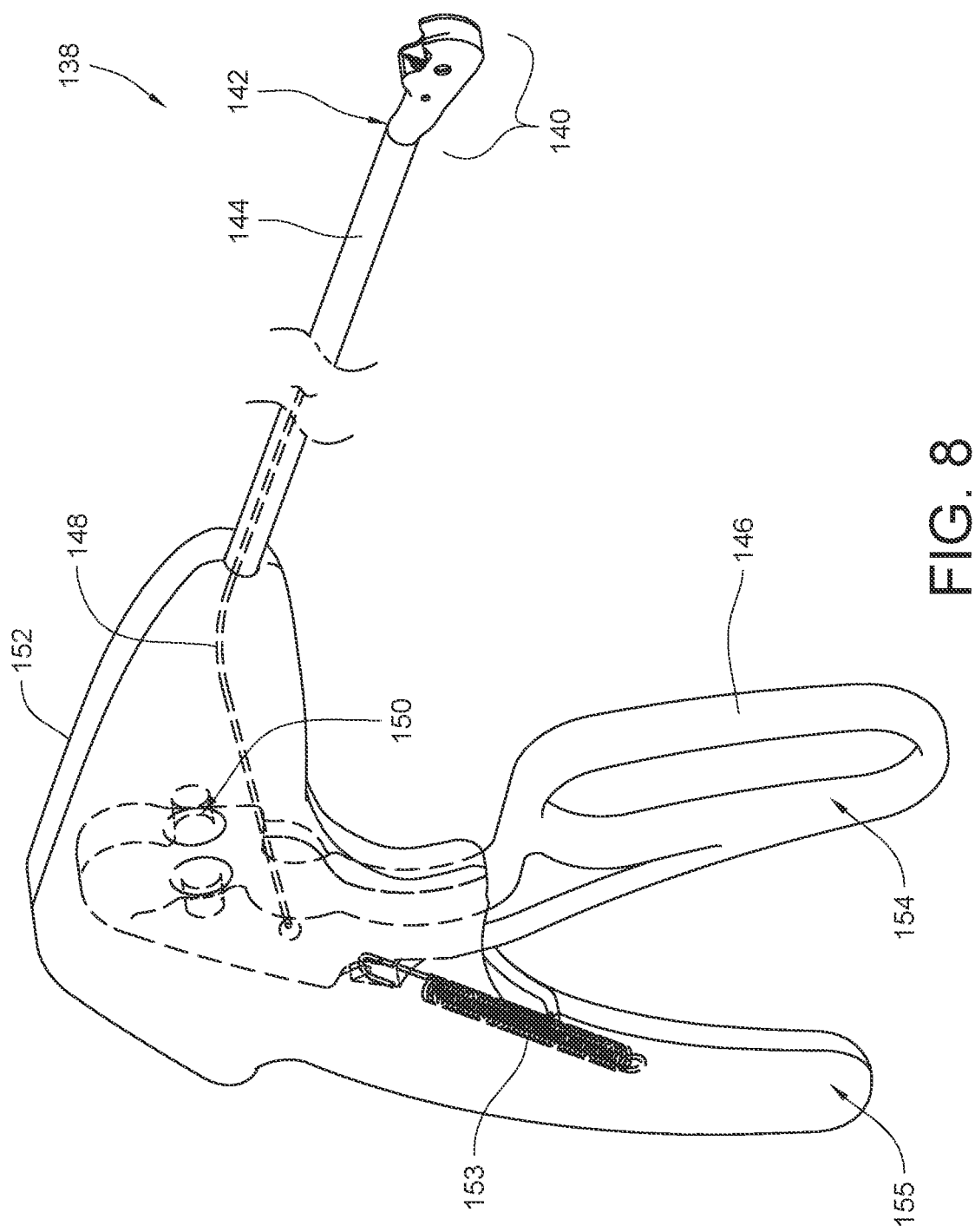
FIG. 8 is a perspective view of another embodiment of a surgical suturing device.

FIG. 8 is a perspective view of another embodiment of a surgical suturing device 138. The surgical suturing device 138 has a device tip 140 which is located at a distal end 142 of a shaft 144 and which will be discussed in more detail below. The surgical suturing device 138 also has an actuator 146 which is coupled to an actuator rod 148. The actuator 146 has an actuator pivot point 150 supported by a housing 152. An actuator spring 153 is coupled between the actuator 146 and the housing 152 to bias the actuator 146 into a retracted position, such as the position shown in FIG. 8. In this embodiment, a handle 154 of the actuator 146 is configured to be moved from the retracted position of FIG. 8 to an engaged position where the actuator 146 is pivoted around the pivot point 150 to move the handle 154 closer to a grip 155 of the housing 152. Since the point where the actuator rod 148 couples to the actuator 146 is between the handle 154 and the pivot point 150 in this embodiment, the actuator rod 148 will move proximally, away from the device tip 140 when the handle 154 is squeezed towards the grip 155. Conversely, in this embodiment, the actuator rod 148 will move distally, toward the device tip 140, when the handle 154 is moved away from the grip 155. Although the actuator 146 in this embodiment includes a lever, other embodiments may utilize a variety of other actuators, including, but not limited to, a control knob, a control wheel, a solenoid, a slider, a screw, one or more gears, one or more pulleys, a motor, or any plurality and/or combination thereof.

Figure 9:
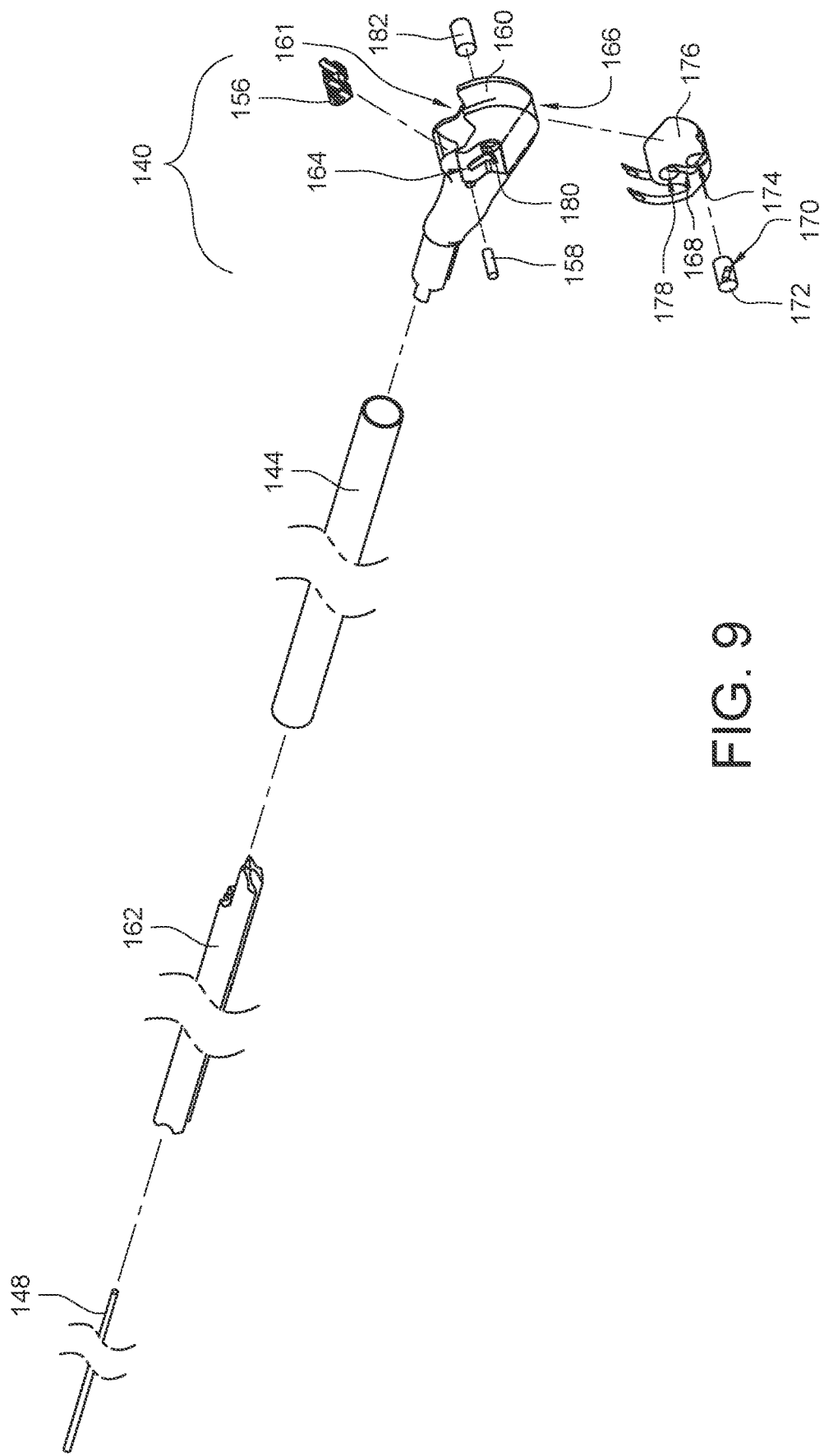
FIG. 9 is an exploded perspective view of the embodied surgical suturing device of FIG. 8 without the housing or needle actuator.

FIG. 9 is an exploded perspective view of the embodied surgical suturing device of FIG. 8 without the housing or needle actuator. The device tip 140 includes a head 160 having a first opening 161 through which a ferrule release feature 156 may be inserted and held in place with a pin 158. The actuator rod 148 may be passed through an actuator rod guide 162 which is sized to fit within shaft 144. The actuator rod 148 also passes through an actuator access channel 164 defined by the head 160. The actuator rod 148 may then temporarily be passed out through a needle access hole 166 defined in the head 160 opposite the first opening 161. The actuator rod 148 can then be passed through an actuator access slot 168 defined by a needle 176 and into a receiving hole 170 of an actuator end effector 172 which fits within an actuator coupler 174 also defined by the needle 176. The actuator rod 148 is coupled to the actuator end effector 172. The needle 176 may be inserted into the needle access hole 166 and the head 160 couples to the shaft 144.

The needle 176 also defines a needle pivot axis 178 which may be aligned with one or more holes 180 in the head 160. The needle pivot axis 178 may be kept in alignment with the one or more holes 180 by a pivot pin 182 which can be inserted into the one or more holes 180 and the needle pivot axis 178. The exploded assembly of the embodiment in FIG. 9 is just one of many possible assemblies, and it should be understood that those skilled in the art will realize other assembly configurations and methods of assembly which can produce the claimed surgical suturing device and its equivalents. Such assembly methods and their equivalents are intended to be included in the scope of this disclosure.

FIGS. 10A-10F show front, right side, left side, top, bottom, and rear views, respectively, for one embodiment of a needle 176 for a surgical suturing device. As noted earlier, in this embodiment, the needle 176 defines an actuator coupler 174 and a needle pivot axis 178. In this embodiment, the needle pivot axis 178 is a cylindrical channel in the needle through which an axle pin may be inserted. In other embodiments, the needle pivot axis may be defined by protrusions on one or more sides of the needle 176. The needle 176 also has a flywheel portion 183 which will be discussed in more detail below.

In this embodiment, the needle 176 has first and second curved arms 184 and 188 extending from the flywheel portion 183. The first curved arm 184 has a first ferrule engaging tip 186 at an end of the first curved arm 184 away from the flywheel portion 183. Likewise, the second curved arm 188 has a second ferrule engaging tip 190 at an end of the second curved arm 188 away from the flywheel portion 183. The first and second ferrule engaging tips 186, 190 and their respective curved arms 184, 188 are configured to be able to pierce tissue as the needle 176 is rotated about the needle pivot axis 178. The first and second ferrule engaging tips 186, 190 are each further configured to releasably engage a ferrule attached to suture (not shown here, as the needle does not include any ferrules).

In this embodiment, the first and second curved arms 184, 188 each extend from the flywheel portion 183 on substantially identical arcs following substantially parallel paths. Furthermore, in this embodiment, the first and second curved arms 184, 188 each have a respective arc centerpoint which falls on the needle pivot axis 178. Also, in this embodiment, each of the first and second curved arms 184, 188 has a substantially round cross-section. Other embodiments may have other cross-sectional shapes, including, but not limited to substantially square cross-sections or substantially triangular cross-sections.

In this embodiment, the first curved arm 184, of needle 176, also includes a first release ramp 192 adjacent to the first ferrule engaging tip 186. Similarly, the second curved arm 188 also includes a second release ramp 194 adjacent to the second ferrule engaging tip 190. The first and second release ramps 192, 194 enable a portion of a ferrule release feature (not shown here, since it is not part of the needle) to be biased against the first and second curved arms 184, 188, and depending on a rotational position of the needle 176, the ferrule release feature can ride up the first and second release ramps 192, 194 to push a ferrule off of each of the first and second ferrule engaging tips 186, 190.

As noted above, the flywheel portion 183 defines an actuator coupler 174. In this embodiment, the actuator coupler 174 is accessible in a first direction, parallel to the pivot axis 178 of the needle 176. This access to the actuator coupler 174 in the first direction may be seen in the views of FIGS. 10A and 10F. The actuator coupler 174 is also accessible in a second direction, perpendicular to the pivot axis 178 of the needle 176. In this embodiment, the flywheel portion 183 also defines an actuator access slot 168 which also facilitates access to the actuator coupler 174 in the second direction. Access to the actuator coupler 174 may be important in some embodiments so that the actuator end effector on the actuator rod (neither item shown here, since they are not part of the needle) may be coupled to the needle 176 and so that the actuator (via the actuator rod in this example) can rotate the needle 176.

As with the previous example, the needle 176 may be made from a variety of materials, including, but not limited to one or more metals, alloys, plastics, polymers, types of glass, ceramics, silicon, and any combination and/or plurality thereof. The flywheel portion 183 of the needle 176 adds mass to the needle to help ensure a smooth rotational needle movement and to help control the orientation of the needle as it moves through tissue by stabilizing the needle 176 against one or more inside surfaces of the device head. In many embodiments, the mass of the flywheel portion 183 may be greater than or equal to the mass of the one or more curved arms 184, 188 of the needle 176. In other embodiments, the mass of the flywheel portion 183 may be less than the mass of the one or more curved arms 184, 188 of the needle 176. Without being tied to one specific theory, the mass of the flywheel portion 183 can also eliminate the need for a guide for the curved arms 184, 188 since the needle 176 may be stabilized by the mass and dimensions of the flywheel portion 183. As can be seen in the views of FIGS. 10A and 10F, the flywheel portion 183 sweeps across an arc of approximately ninety degrees in addition to helping define the needle pivot axis 178. Other embodiments may include one or more arc sweeps of lesser, greater, or similar size. As can be seen in the views of FIGS. 10B, 10C, 10D, and 10E, the flywheel portion 183 also has a width which reaches between the two curved arms 184, 188. In other embodiments, the flywheel portion 183 may have thinner or wider widths. The flywheel portion 183 may also include a tissue-engaging portion as will be discussed in the examples below.

FIGS. 11A-11C show the distal end of the surgical suturing device of FIG. 8 in a partially sectioned perspective view, illustrating the movement of the needle 176. FIG. 11A corresponds to FIG. 12A, FIG. 11B corresponds to FIG. 12B, and FIG. 11C corresponds to FIG. 12C. In FIG. 11A, the needle 176 is shown in a retracted position, where the first ferrule engaging tip 186 and the second ferrule engaging tip (not visible in this view) start away from their respective first and second ferrule holders 196, 198. The ferrule holders 196, 198 are either formed from or coupled to the device head 160. A first ferrule 200 and a second ferrule 202 are each installed in and held by respective first and second ferrule holders 196, 198. The first ferrule 200 is coupled to a first end 204 of a suture 208, while the second ferrule 202 is coupled to a second end 206 of the suture 208. The suture 208 may be of a variety of lengths, and for convenience the portion of the suture 208 where it loops back on itself is not shown. As before, it should be understood that the term "suture", as used herein, is intended to cover any thread, cable, wire, filament, strand, line, yarn, gut, or similar structure, whether natural and/or synthetic, in monofilament, composite filament, or multifilament form (whether braided, woven, twisted, or otherwise held together), as well as equivalents, substitutions, combinations, and pluralities thereof for such materials and structures.

The head 160, along with a tissue engaging surface 209 of the flywheel portion of the needle 176, define a tissue bite area 218. In this embodiment, as can be better seen in FIG. 12A, the tissue bite area 218 faces a direction which is substantially oblique to a longitudinal axis 219 of the shaft 144.

As shown in FIGS. 11B and 12B, the actuator rod 148 may be moved in a proximal direction 210, which will cause the needle 176 to rotate in a first direction 212 about its needle pivot axis. While rotating in this first direction 212, the ferrule engaging tips 186, 190 of the curved arms 184, 188 pass from their retracted position (shown in FIGS. 11A, 12A), through the tissue bite area 218, and to an engaged position (shown in FIGS. 11B, 12B). In this embodiment, the ferrule engaging tips 186, 190 move along an arcuate path from a proximal side of the head 160 towards a distal end of the head 160. In the engaged position of FIGS. 11B, 12B, the ferrule engaging tips 186, 190 are each coupled to corresponding ferrules 200, 202 by an interference fit or alternate attachment mechanism, the choice of which is known to those skilled in the art. This coupling of the ferrule engaging tips with the corresponding ferrules may be referred to as operational alignment.

As shown in FIGS. 11C and 12C, the actuator rod 148 may be moved in a distal direction 214, which will cause the needle 176 to rotate in a second direction 216 (opposite the first direction 212) about its needle pivot axis. While rotating in this second direction 216, the ferrule engaging tips 186, 190 of the curved arms 184, 188 (and the ferrules 200, 202 which are coupled to them) pass from their engaged position (shown in FIGS. 11B and 12B), back through the tissue bite area 218, and to the retracted position as shown in FIGS. 11C and 12C. In this embodiment, while moving back to the retracted position, the ferrule engaging tips 186, 190 move along an arcuate path from the distal end of the head 160 to the proximal side of the head 160. Depending on the embodiment, if a ferrule release feature 156 is present in the device, the ferrule release feature 156 may have elements which are positioned to ride against the curved arms, up the release ramps of the curved arms, and against the ferrules 200, 202 to remove the ferrules 200, 202 from the ferrule engaging tips 186, 190 when the tips 186, 190 return to the retracted position. In other embodiments, the actuator 156 may be configured to selectively rotate the needle 176 past the retracted position, away from the engaged position, when desired, in order then to force the captured ferrules 200, 202 to engage the ferrule release feature 156. Some embodiments may not include a ferrule release feature at all.

Figure 13A:
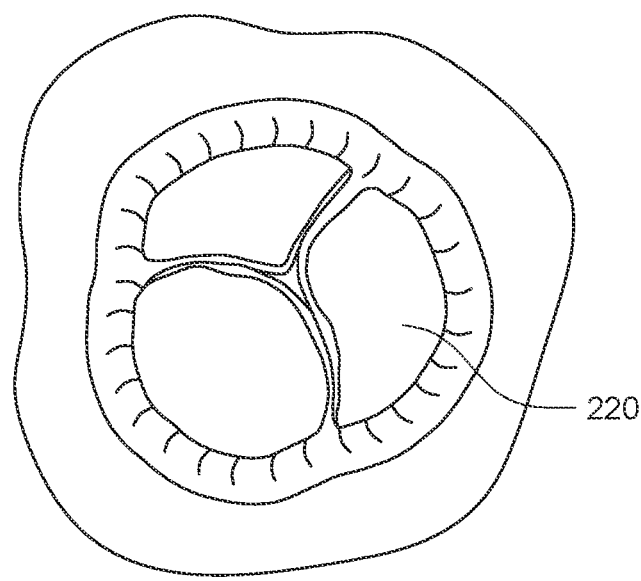
FIGS. 13A-13G illustrate a method of using an embodiment of the surgical suturing device from FIG. 8 to place a pledgeted suture in a valve annulus which has had its diseased valve leaflets removed.
Figure 13B:
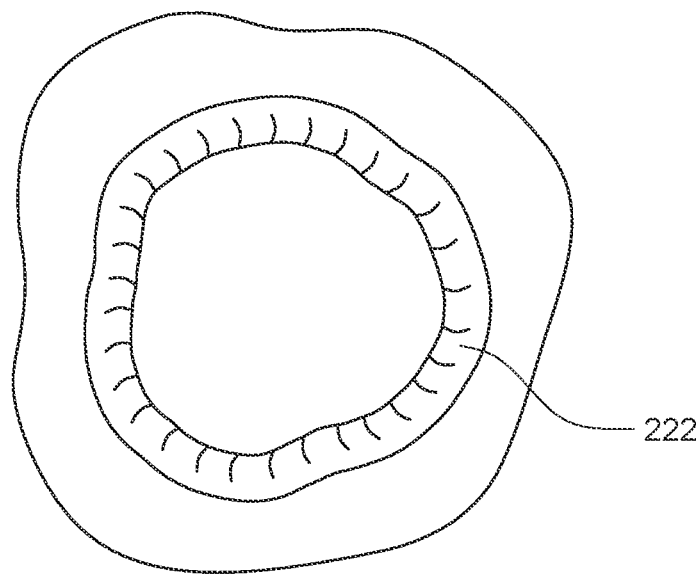
Figure 13C:
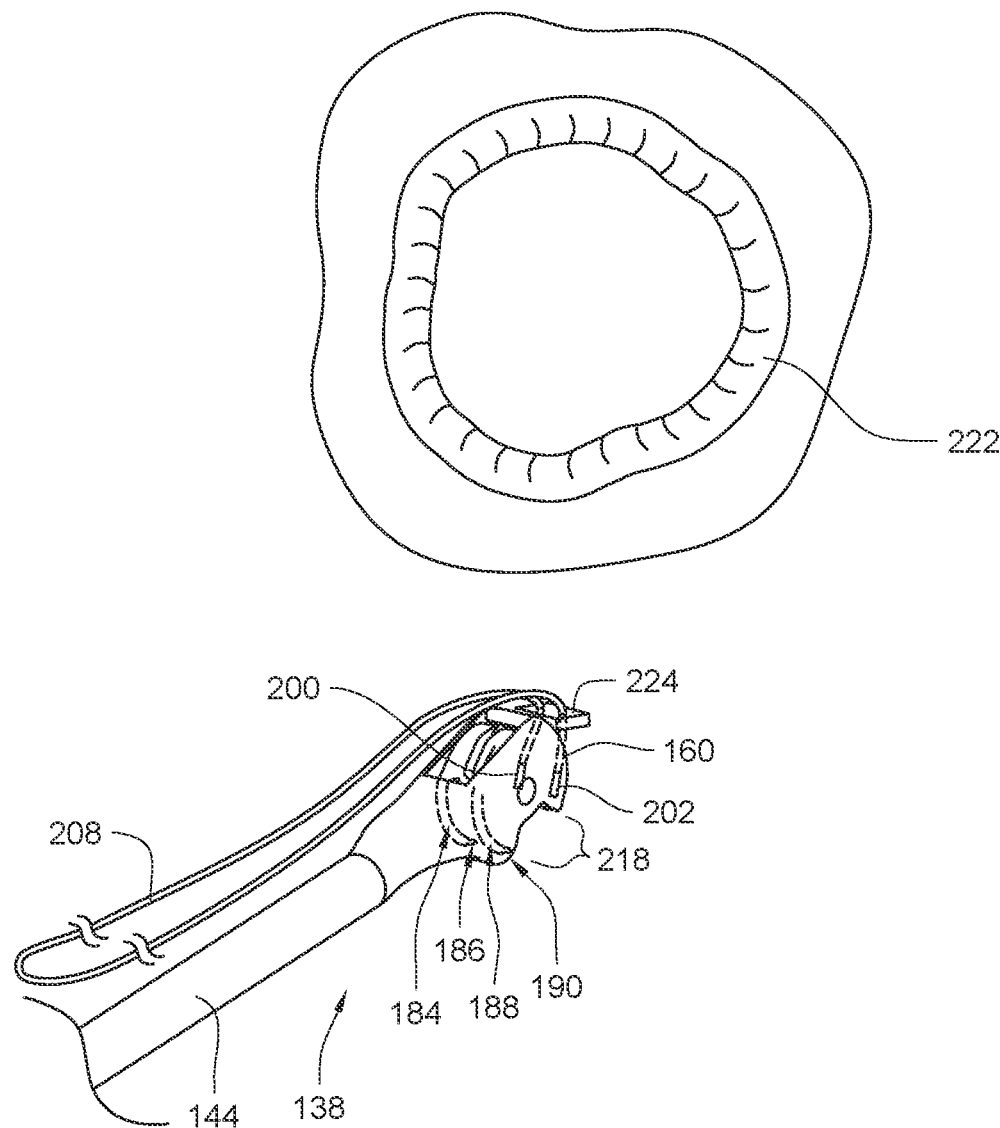

FIGS. 13A-13G illustrate a method of using an embodiment of the surgical suturing device from FIG. 8 to place a pledgeted suture in a valve annulus which has had its diseased valve leaflets removed. FIG. 13A schematically illustrates a diseased heart valve 220 in need of replacement. As a first action, a surgeon might gain access to the diseased valve 220 and dissect the leaflets of the valve, leaving the annulus 222 in preparation for installation of a replacement heart valve as shown in FIG. 13B. As illustrated in FIG. 13C, the suturing device 138 is ready to be used. For convenience, the handle, actuator, and entire shaft are not shown in these views. As before, the device 138 has a tissue bite area 218 defined at least in part by the head 160 at the end of the shaft 144. First and second ferrules 200, 202, coupled to the ends of suture 208 are held in ferrule holders on the distal side of the tissue bite area 218 in the device head 160. The first and second curved arms 184, 188 and their respective first and second ferrule engaging tips 186, 190 are in a retracted position on the proximal side of the tissue bite area 218. In this embodiment, the suture 208 is also pledgeted with a pledget 224 pre-installed on the suture 208.

Figure 13D:
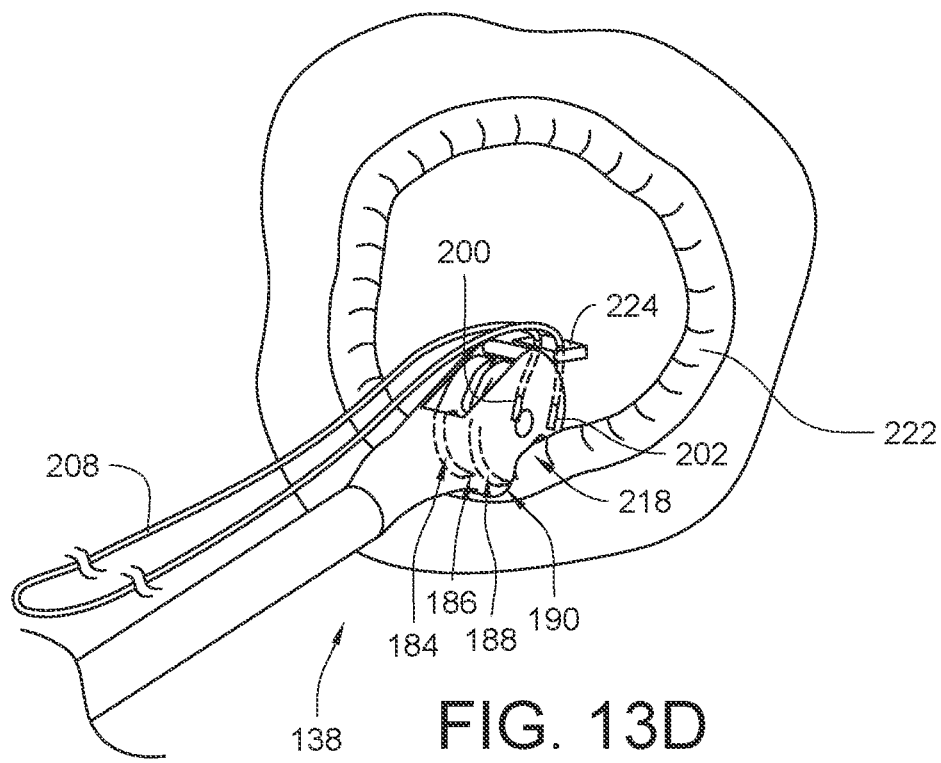

In this example, it would be desirable to attach the replacement heart valve to the remaining annulus 222. Therefore, as illustrated in FIG. 13D, the tissue bite area 218 of the surgical suturing device 138 could be placed over a portion of the annulus 222 where it would be desired to make some attachment stitches.

Figure 13E:
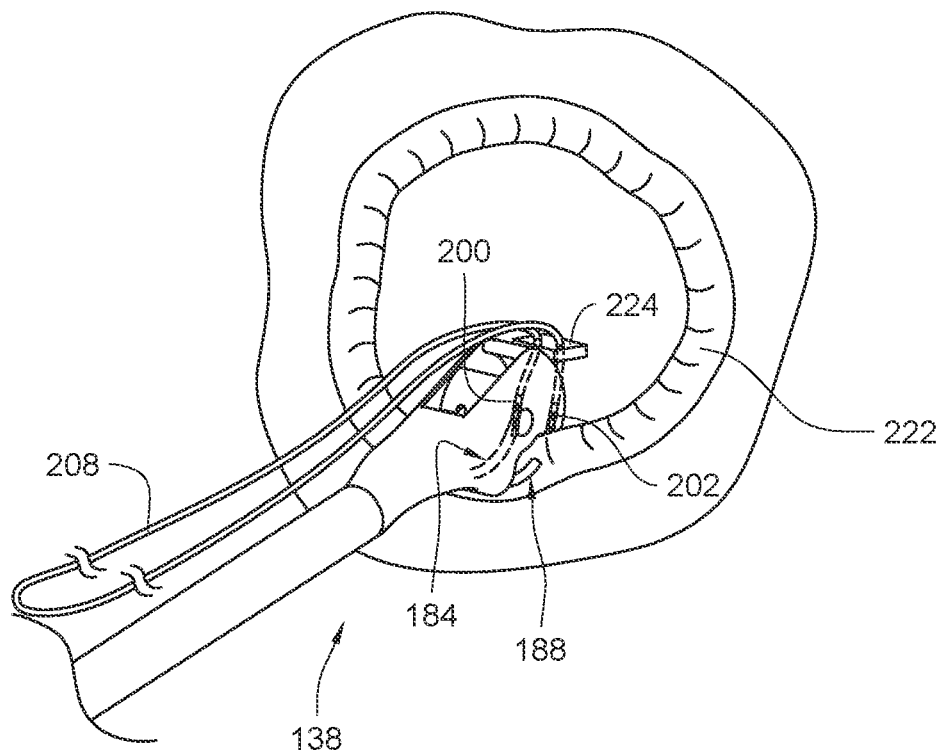
Figure 13F:
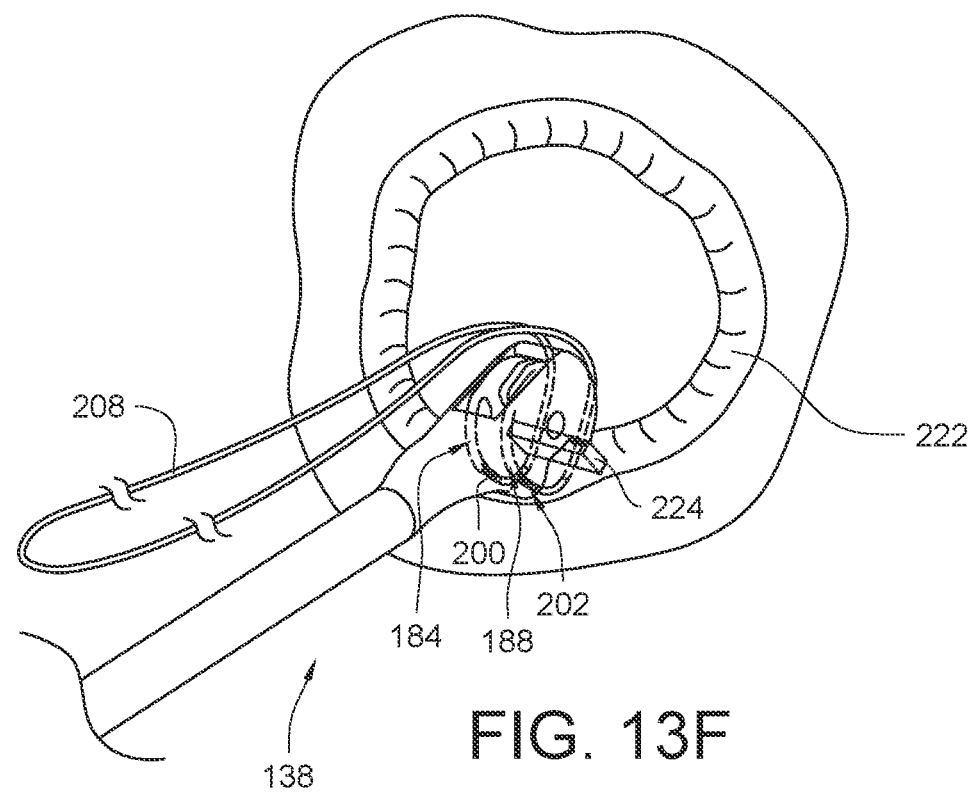
Figure 13G:
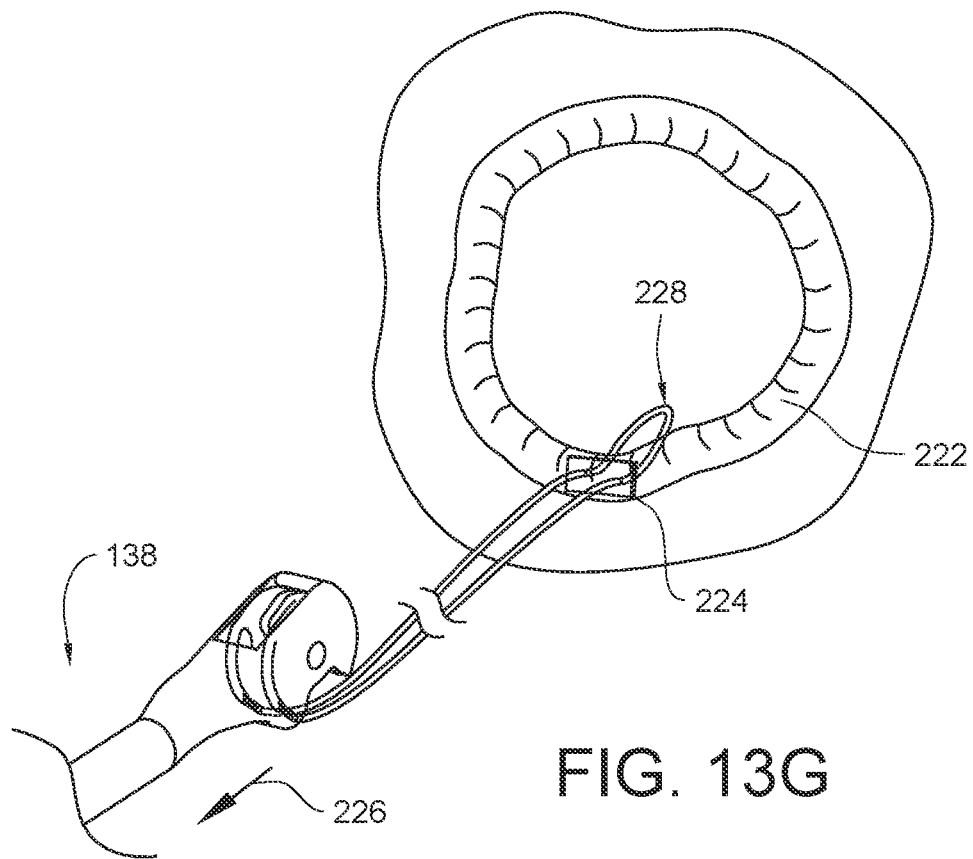

As shown in FIG. 13E, the needle is actuated so that the first and second curved arms 184, 188, and their respective ferrule engaging tips, pass through the annulus 222 in the tissue bite area and engage the corresponding first and second ferrules 200, 202. As shown in FIG. 13F, the needle is then reverse-actuated so that the first and second curved arms 184, 188 and their respective ferrule engaging tips and the respective ferrules 200, 202 held by those ferrule engaging tips are pulled back through the annulus 222 in the tissue bite area and into a retracted position again. Since the ends of suture 208 are coupled to the ferrules 200, 202, the suture 208 is also pulled through the annulus 222. The device 138 can be pulled back 226 to tighten a portion 228 of the suture 208 against the pledget 224, and ultimately against the annulus 222.

Figure 13H:
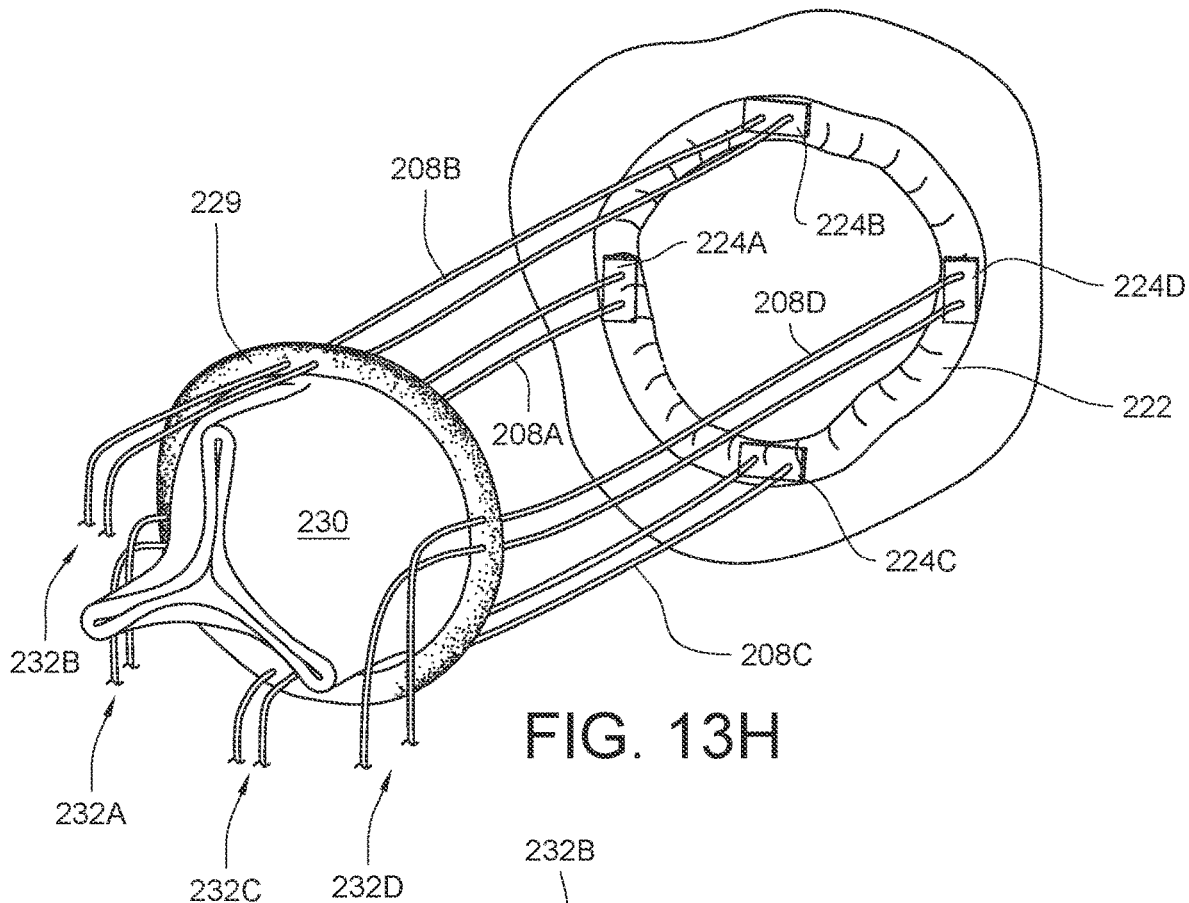
FIGS. 13H-13I illustrate a method of coupling multiple sutures placed in a valve annulus to the sewing cuff of a replacement heart valve using mechanical fasteners as part of a heart valve replacement procedure.

The ferrules 200, 202 on the ends of the suture 208 can be released or otherwise removed. Another suture can be loaded into the device, and the process can be repeated around the annulus 222 as many times as desired by the surgeon. As a simple example, FIG. 13H illustrates the result of having performed the process four times with the device 138. Four sutures 208A, 208B, 208C, 208D have been placed in desired locations through the annulus 222. Those four sutures 208A, 208B, 208C, 208D have also been placed through corresponding locations in a sewing cuff 229 of a replacement heart valve 230. Those skilled in the art are familiar with methods of placing suture stitches in a sewing cuff 229. Each suture 208A, 208B, 208C, 208D passes through both the annulus 222 and the sewing cuff 229 twice and is positioned so that it holds a respective pledget 224A, 224B, 224C, 224D against the annulus 222 and terminates in a respective pair of suture ends 232A, 232B, 232C, 232D. In practice, this process can be used for any number of sutures. The four sutures illustrated here are just for the convenience of explanation.

Figure 13I:
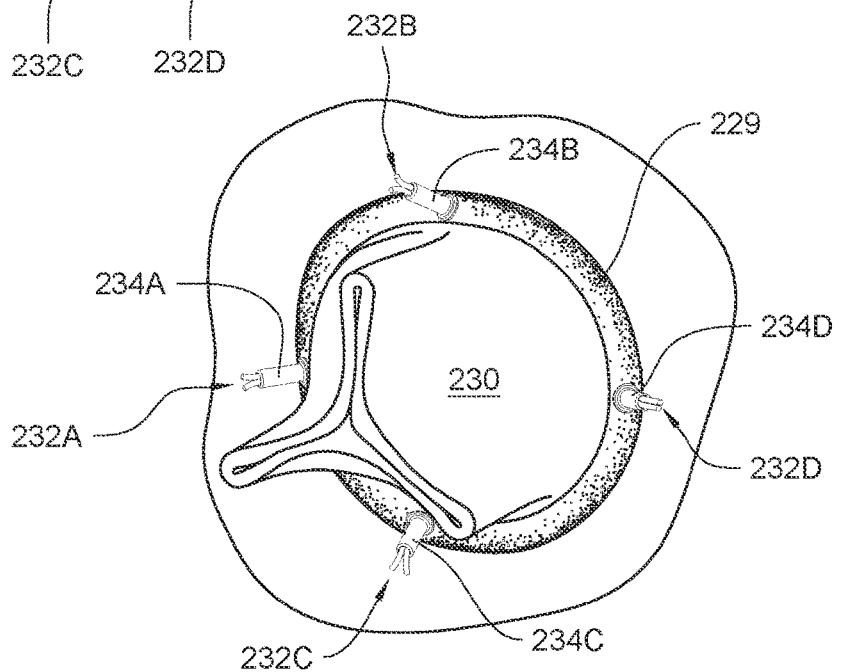

Tension can be maintained on the suture ends 232A, 232B, 232C, 232D while the replacement valve 230 is moved down the sutures and against the annulus 222. Each pair of suture ends 232A, 232B, 232C, 232D can then be tied off, knotted, clamped, or otherwise fixed against the sewing cuff 229 to hold the valve 230 in place. As one non-limiting example, each pair of suture ends 232A, 232B, 232C, 232D may be knotted with a mechanical knot 234A, 234B, 234C, 234D as illustrated in FIG. 13I. The mechanical knots 234A, 234B, 234C, 234D may be applied, for example, with a COR-KNOT® device available from LSI Solutions, Inc. of Victor, NY. (For example, find ordering contact information at www.lsisolutions.com). Other embodiments of mechanical knots or other types of knots may be used to finalize the attachment of the replacement anatomical structure.

Figure 14:
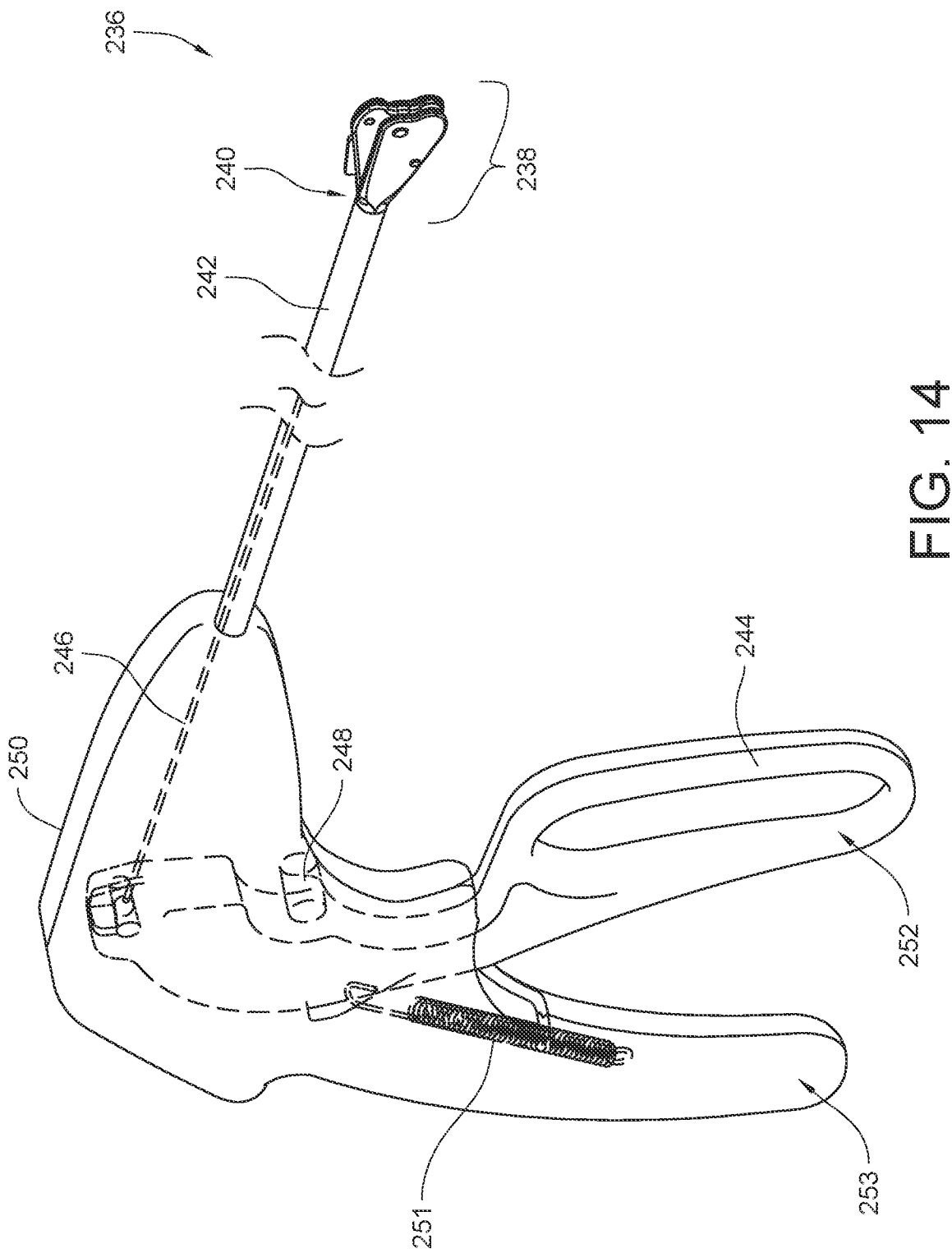
FIG. 14 is a perspective view of a further embodiment of a surgical suturing device.

FIG. 14 is a perspective view of one embodiment of a surgical suturing device 236. The surgical suturing device 236 has a device tip 238 which is located at a distal end 240 of a shaft 242 and which will be discussed in more detail below. The surgical suturing device 236 also has an actuator 244 which is coupled to an actuator rod 246. The actuator 244 has an actuator pivot point 248 supported by a housing 250. An actuator spring 251 is coupled between the actuator 244 and the housing 250 to bias the actuator 244 into a retracted position, such as the position shown in FIG. 14. In this embodiment, a handle 252 of the actuator 244 is configured to be moved from the retracted position of FIG. 14 to an engaged position where the actuator 244 is pivoted around the pivot point 248 to move the handle 252 closer to a grip 253 of the housing 250. Since the pivot point 248 is between the handle 252 and the point where the actuator rod 246 couples to the actuator 244 in this embodiment, the actuator rod 246 will move distally, toward the device tip 238 when the handle 252 is squeezed towards the grip 253. Conversely, in this embodiment, the actuator rod 246 will move proximally, toward the housing 250, when the handle 252 is moved away from the grip 253. Although the actuator 244 in this embodiment includes a lever, other embodiments may utilize a variety of other actuators, including, but not limited to, a control knob, a control wheel, a solenoid, a slider, a screw, one or more gears, one or more pulleys, a motor, or any plurality and/or combination thereof.

Figure 15:
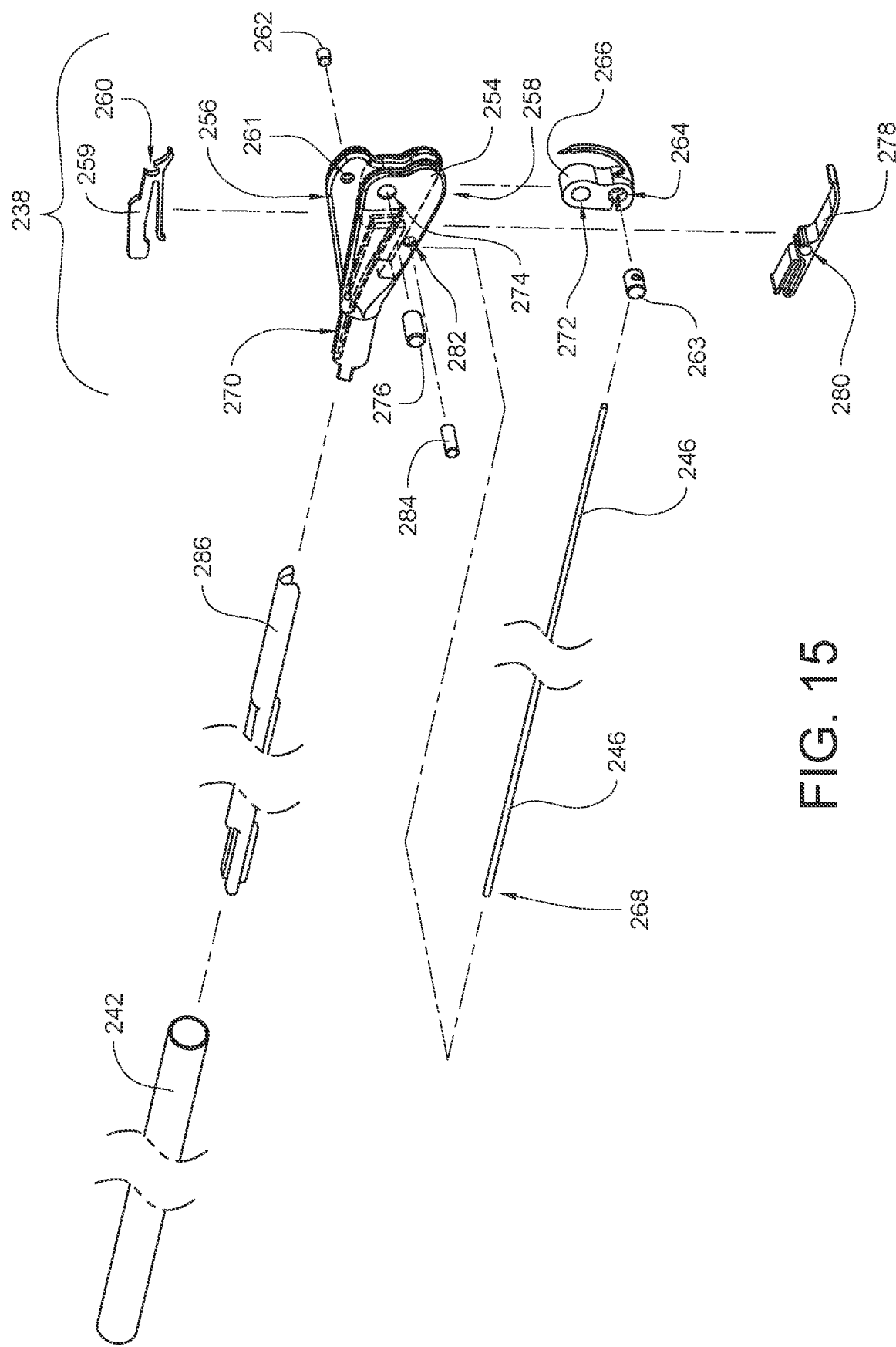
FIG. 15 is an exploded perspective view of the embodied surgical suturing device of FIG. 14 without the housing or needle actuator.

FIG. 15 is an exploded perspective view of the embodied surgical suturing device 236 of FIG. 14 without the housing or needle actuator. The device tip 238 includes a head 254 having a first opening 256 through which a first ferrule release feature 259 may be inserted. The first ferrule release feature 259 may define a pivot notch 260 that can be aligned with one or more holes 261 in the head 254. A pin 262 may be inserted into the one or more holes 261 and the pivot notch 260 to help hold the first ferrule release feature 259 in place.

A distal end of the actuator rod 246 may be coupled to an actuator end effector 263. The actuator end effector 263 may be inserted into an actuator coupler 264 defined by a needle 266. A proximal end 268 of the actuator rod 246 and the needle 266 may be inserted into a needle access hole 258 in a side of the head 254 opposite the first opening 256, the actuator rod 246 being positioned within an actuator access channel 270 also defined by the head 254. The actuator rod 246 will extend out of the head 254 and can be fitted within an actuator rod guide 286 which fits within the shaft 242. Other embodiments may forego an actuator rod guide 286, and may instead just use the shaft 242 to contain the actuator rod 246. The head 254 couples to the shaft 54.

The needle 266 also defines a needle pivot axis 272 which may be aligned with one or more holes 274 in the head 254. The needle pivot axis 272 may be kept in alignment with the one or more holes 274 by a pivot pin 276 which can be inserted into the one or more holes 274 and the needle pivot axis 272. A second ferrule release feature 278 may also be installed through the second access hole 258 in the head 254. The second ferrule release feature 278 may define a pivot point 280, which may be aligned with one or more holes 282 in the head 254. A pivot pin 284 may be inserted into the one or more holes 282 and through the pivot point 280 to position and hold the second ferrule release feature 278. The exploded assembly of the embodiment in FIG. 15 is just one of many possible assemblies, and it should be understood that those skilled in the art will realize other assembly configurations and methods of assembly which can produce the claimed surgical suturing device and its equivalents. Such assembly methods and their equivalents are intended to be included in the scope of this disclosure.

FIGS. 16A-16F show front, right side, left side, top, bottom, and rear views, respectively, for one embodiment of a needle 266 for a surgical suturing device. As noted earlier, in this embodiment, the needle 266 defines an actuator coupler 264 and a needle pivot axis 272. In this embodiment, the needle pivot axis 272 is a cylindrical channel in the needle through which an axle pin may be inserted. In other embodiments, the needle pivot axis may be defined by protrusions on one or more side of the needle 266. The needle 266 also has a flywheel portion 288 which will be discussed in more detail below.

In this embodiment, the needle 266 has a curved arm 290 extending from the flywheel portion 288. The curved arm 290 has a ferrule engaging tip 292 at an end of the curved arm 290 away from the flywheel portion 288. The ferrule engaging tip 292 and its curved arm 290 are configured to be able to pierce tissue as the needle 266 is rotated about the needle pivot axis 272. The ferrule engaging tip 292 is further configured to releasably engage a ferrule attached to suture (not shown here, as the needle does not include any ferrules).

In this embodiment, the curved arm 290 has an arc centerpoint which falls on the needle pivot axis 272. In this embodiment, the curved arm 290 also has a substantially square cross-section. Other embodiments may have other cross-sectional shapes, including, but not limited to substantially round cross-sections or substantially triangular cross-sections.

In this embodiment, the curved arm 290, of the needle 266, also includes a release ramp 293 adjacent to the ferrule engaging tip 292. The release ramp 293 enables a portion of a ferrule release feature (not shown here, since it is not part of the needle) to be biased against the curved arm 290 and, depending on a rotational position of the needle 266, the ferrule release feature can ride up the release ramp 293 to push a ferrule off of the ferrule engaging tip 292.

As noted above, the flywheel portion 288 defines an actuator coupler 264. In this embodiment, the actuator coupler 264 is accessible in a first direction, parallel to the pivot axis 272 of the needle 266. This access to the actuator coupler 264 in the first direction may be seen in the views of FIGS. 16A and 16F. The actuator coupler 264 is also accessible in a second direction, perpendicular to the pivot axis 272 of the needle 266. In this embodiment, the flywheel portion 288 also defines an actuator access slot 294 which also facilitates access to the actuator coupler 264 in the second direction. Access to the actuator coupler 264 may be important in some embodiments so that the actuator end effector on the actuator rod (neither item shown here, since they are not part of the needle) may be coupled to the needle 266 and so that the actuator (via the actuator rod in this example) can rotate the needle 266.

As noted earlier, the needle 266 may be made from a variety of materials, including, but not limited to one or more metals, alloys, plastics, polymers, types of glass, ceramics, silicon, and any combination and/or plurality thereof. The flywheel portion 288 of the needle 266 adds mass to the needle to help ensure a smooth rotational needle movement and to help control the orientation of the needle as it moves through tissue by stabilizing the needle 266 against one or more inside surfaces of the device head. In many embodiments, the mass of the flywheel portion 288 may be greater than or equal to the mass of the curved arm 290 of the needle 266. In other embodiments, the mass of the flywheel portion 288 may be less than the mass of the curved arm 290, although this is not preferred in a single curved arm needle embodiment. Without being tied to one specific theory, the mass of the flywheel portion 288 can also eliminate the need for a guide for the curved arm 290 since the needle 266 may be stabilized by the mass and dimensions of the flywheel portion 288. The flywheel portion 288 may also include a tissue-engaging portion as will be discussed in the examples below.

Figure 17:
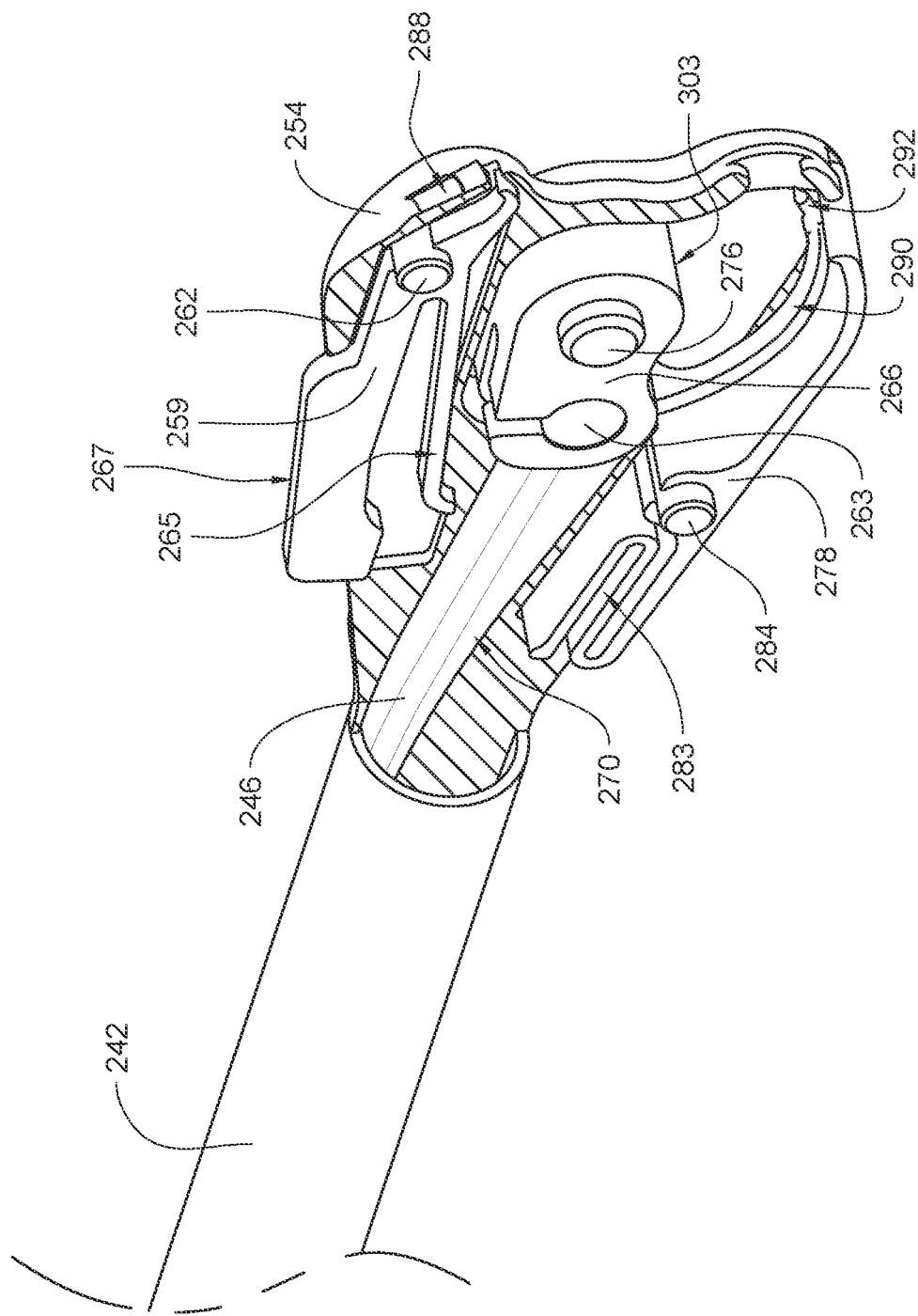
FIG. 17 illustrates the distal end of the surgical suturing device of FIG. 14 in a partially sectioned perspective view.

FIG. 17 illustrates the distal end of the surgical suturing device of FIG. 14 in a partially sectioned perspective view. The second ferrule release feature 278 may be seen. This second ferrule release feature 278 pivots on pivot pin 284 and is biased by spring portion 283 to ride against the curved arm 290. This second ferrule release feature 278 operates similarly to previously discussed ferrule release features, and is useful for releasing a ferrule and its suture from the device.

The first ferrule release feature 259 is also visible in the partially sectioned view of FIG. 17. The first ferrule release feature 259 pivots on pivot pin 262 and is biased away from a travel path of the curved arm 290 by a spring portion 265. The first ferrule release feature 259 will not engage the curved arm 290, unless manual button 267 is pushed in towards the head 254. The operation of the first ferrule release feature 259 will be discussed in more detail below.

Figure 18A:
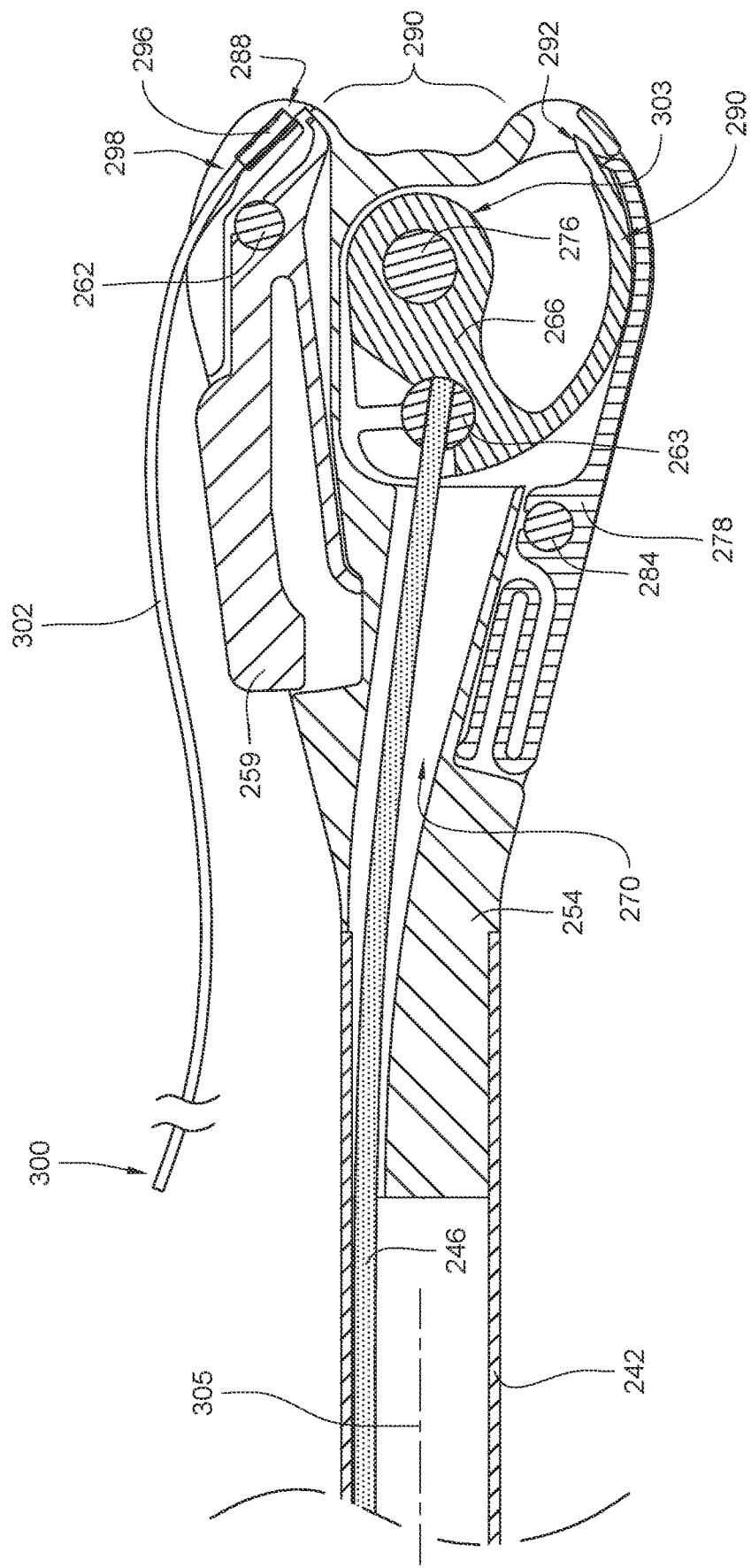
FIGS. 18A-18C illustrate the distal end of the surgical suturing device of FIG. 14 in a partially sectioned side view, loaded with a suture, and illustrating the movement of the needle from a retracted position to an engaged position and back to the retracted position.
Figure 18B:
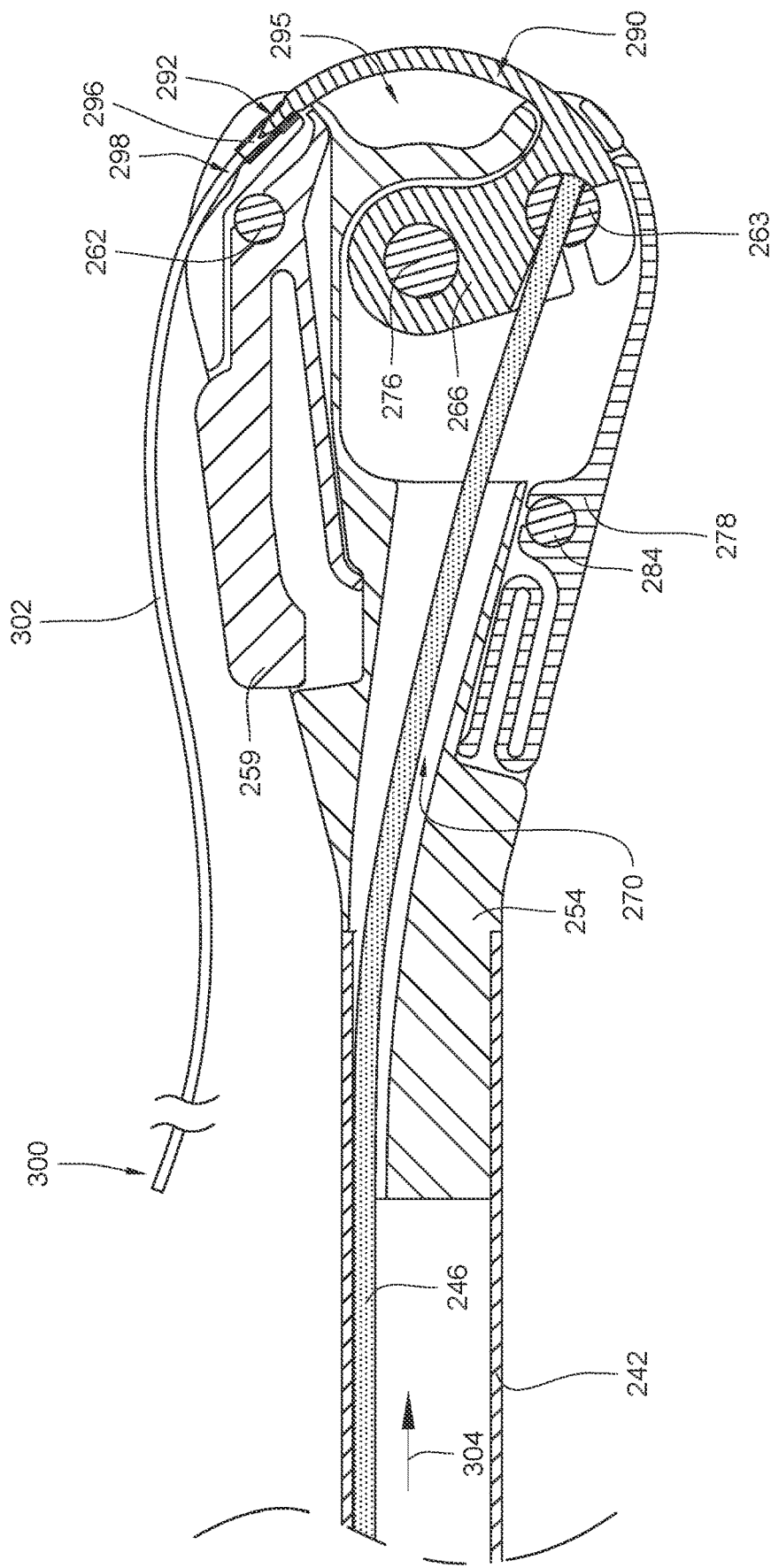
Figure 18C:
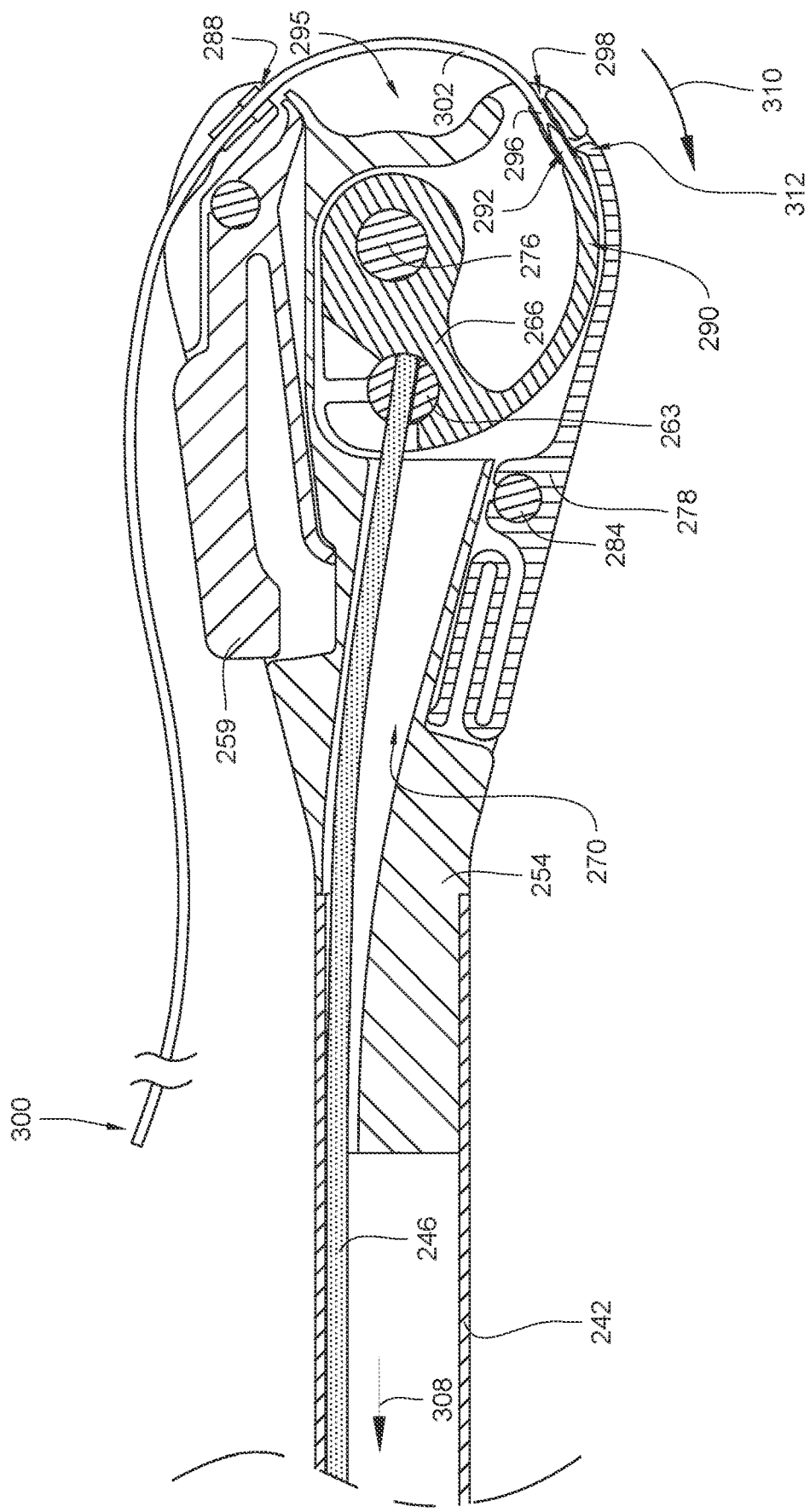

FIGS. 18A-18C show the distal end of the surgical suturing device of FIG. 14 in a partially sectioned side view, illustrating the movement of the needle 266. In FIG. 18A, the needle 266 is shown in a retracted position, where the ferrule engaging tip 292 starts away from its ferrule holder 288. The ferrule holder 288 is either formed from or coupled to the device head 254. A ferrule 296 is installed in and held by the ferrule holder 288. The ferrule 296 is coupled to a first end 298 of a suture 302. A second end 300 of the suture 302 is illustrated as not having a ferrule in this embodiment, but in some embodiments, the second end 300 of the suture 302 could also have a ferrule. As before, it should be understood that the term "suture", as used herein, is intended to cover any thread, cable, wire, filament, strand, line, yarn, gut, or similar structure, whether natural and/or synthetic, in monofilament, composite filament, or multifilament form (whether braided, woven, twisted, or otherwise held together), as well as equivalents, substitutions, combinations, and pluralities thereof for such materials and structures.

The head 254, along with a tissue engaging surface 303 of the flywheel portion of the needle 266, defines a tissue bite area 295. In this embodiment, the tissue bite area 295 faces a direction which is substantially parallel to a longitudinal axis 305 of the shaft 242.

As shown in FIG. 18B, the actuator rod 246 may be moved in a distal direction 304, which will cause the needle 266 to rotate in a first direction 306 about its needle pivot axis. While rotating in this first direction 306, the ferrule engaging tip 292 of the curved arm 290 passes from its retracted position (shown in FIG. 18A), through the tissue bite area 295, and to an engaged position (shown in FIG. 18B). In this embodiment, the ferrule engaging tip 292 moves along an arcuate path substantially transverse to the longitudinal axis 305 of the shaft 242. In the engaged position of FIG. 18B, the ferrule engaging tip 292 is coupled to the ferrule 296 by an interference fit or alternate attachment mechanism, the choice of which is known to those skilled in the art. This coupling of the ferrule engaging tips with the corresponding ferrules may be referred to as operational alignment.

As shown in FIG. 18C, the actuator rod 246 may be moved in a proximal direction 308, which will cause the needle 266 to rotate in a second direction 310 (opposite the first direction 306) about its needle pivot axis. While rotating in this second direction 310, the ferrule engaging tip 292 of the curved arm 290 (and the ferrule 296 which is coupled to it) passes from its engaged position (shown in FIG. 18B), back through the tissue bite area 295, and to the retracted position as shown in FIG. 18. In this embodiment, while moving back to the retracted position, the ferrule engaging tip 292 moves along an arcuate path.

Figure 18D:
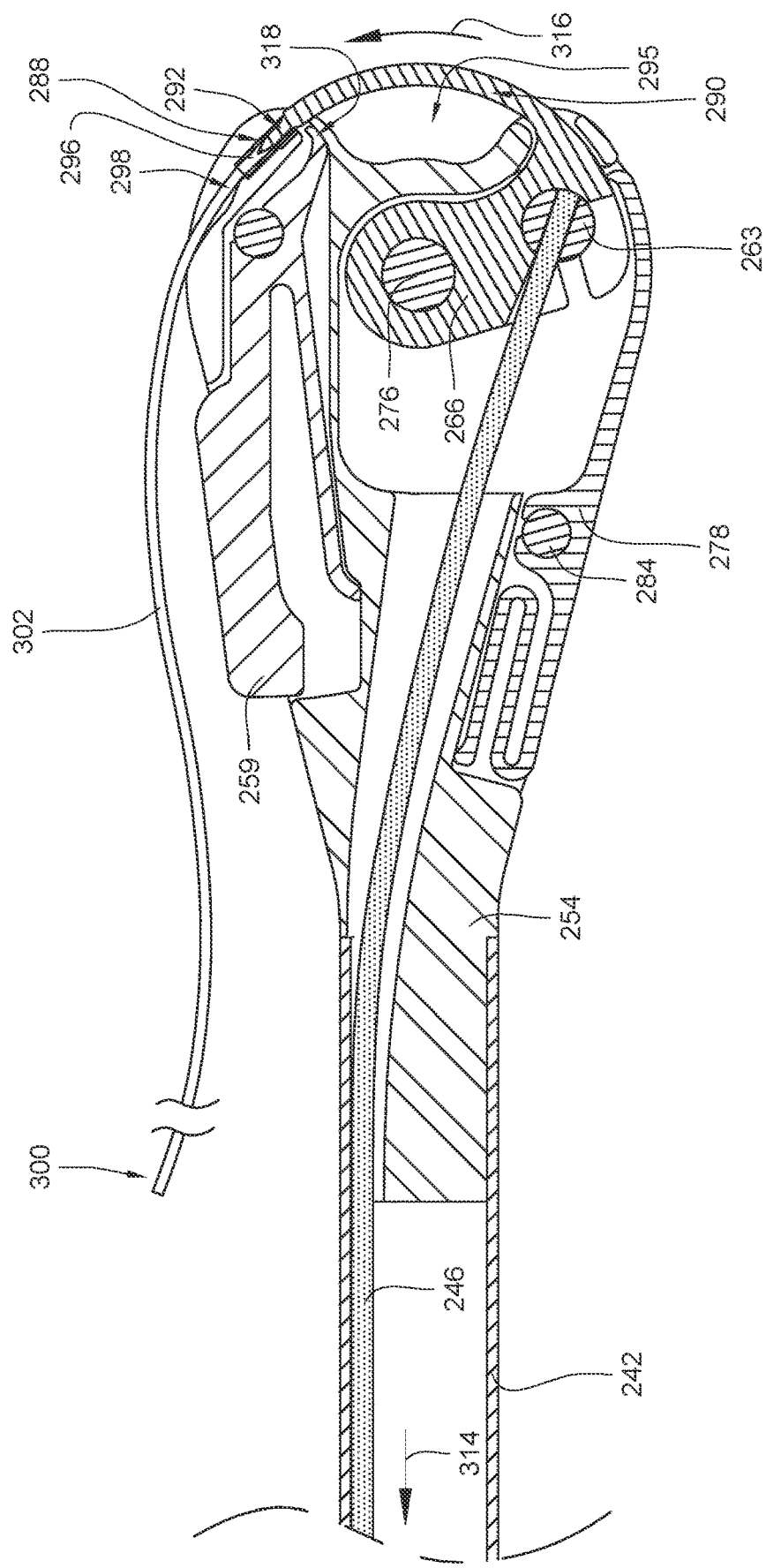
FIGS. 18D-18F illustrate the distal end of the surgical suturing device of FIG. 14 in a partially sectioned side view, where the ferrule-engaging tip of the curved arm is initially coupled to a suture ferrule, and illustrating the movement of the needle from a retracted position to an engaged position and back to the retracted position in order to deposit the suture ferrule back in a ferrule holder.
Figure 18E:
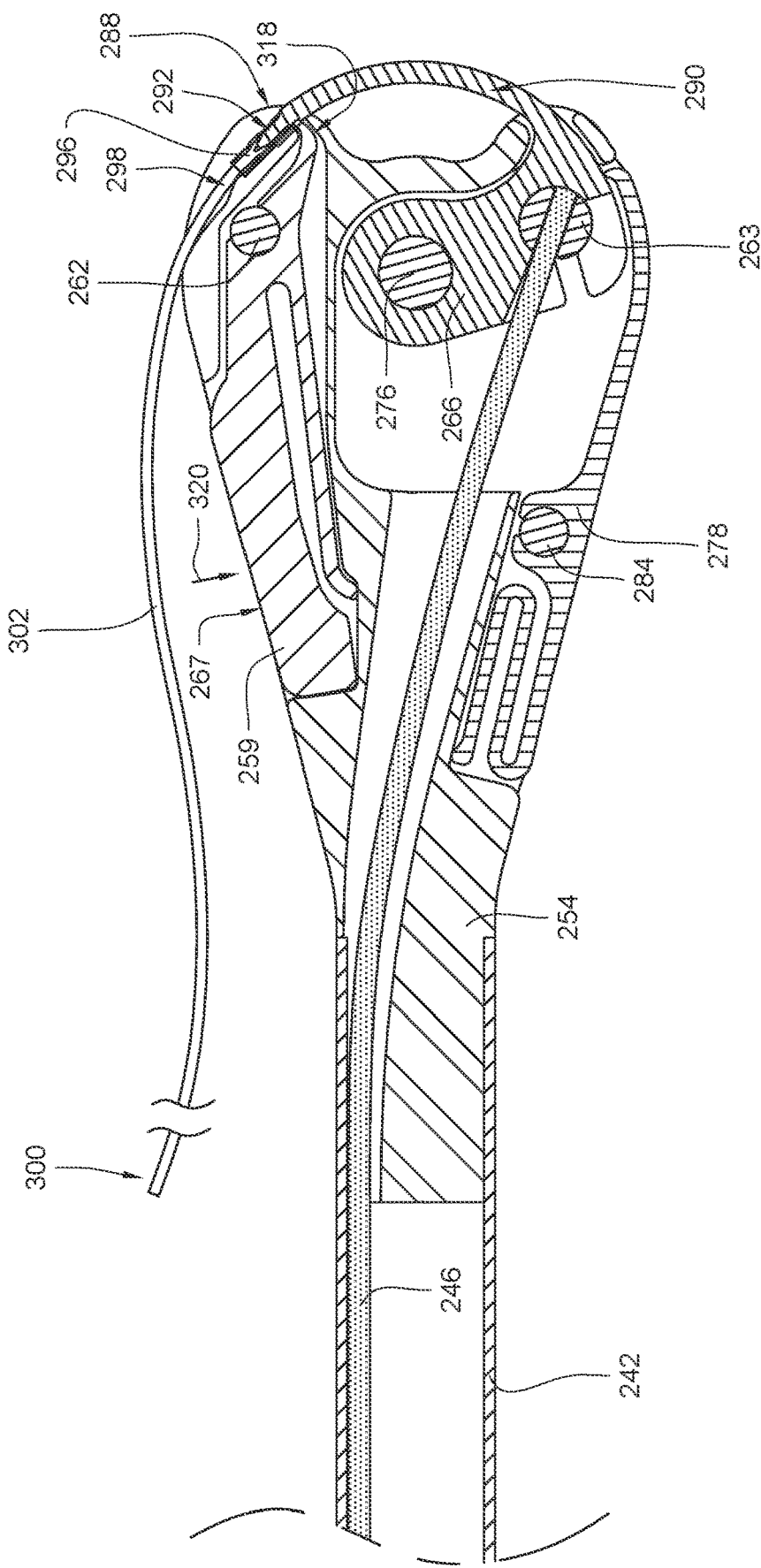
Figure 18F:
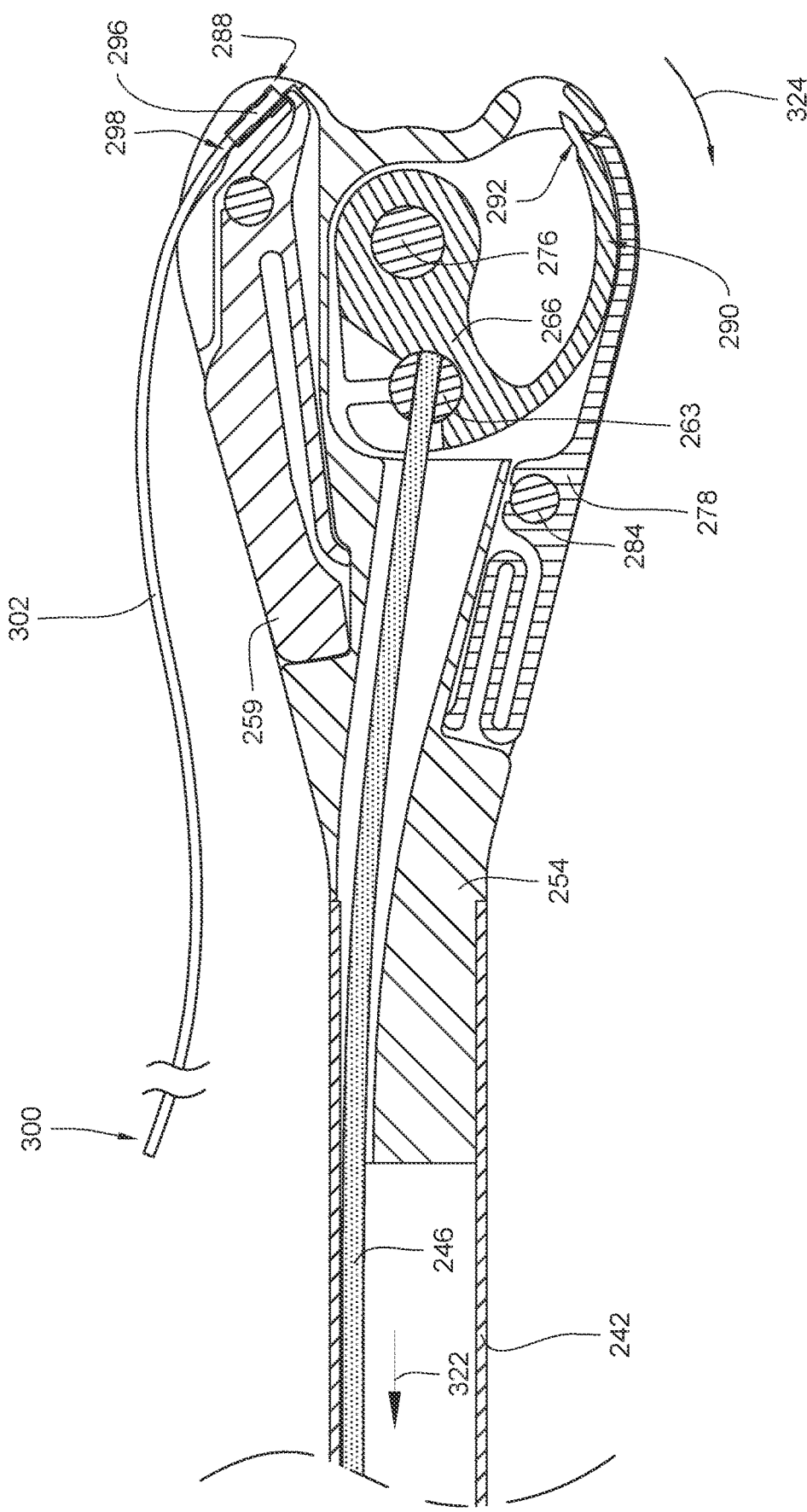

If the needle 266 is not rotated far enough for tip 312 of the second ferrule release feature 278 to remove the ferrule 296 from the ferrule engaging tip 292, a further set of actions may be taken to reset the ferrule 296 and the device to their initial positions, as illustrated in FIGS. 18D-18F. As shown in FIG. 18D, the actuator rod 246 may again be moved in a distal direction 314, which will cause the needle 266 to rotate in a first direction 316 about its needle pivot axis. While rotating in this first direction 306, the ferrule engaging tip 292 of the curved arm 290 (and the ferrule 296 which is coupled to it) passes from its starting position (shown in FIG. 18C), through the tissue bite area 295, and to the engaged position of FIG. 18D. The device is ideally moved away from the tissue it may have previously had the suture pass through prior to this step. The ferrule engaging tip 292 is still coupled to the ferrule 296, but the ferrule 296 is now positioned within the ferrule holder 288.

As illustrated in FIG. 18E, a tip 318 of the first ferrule removal feature 259 can be caused to engage the curved arm 290 below the ferrule 296 by depressing 320 the button 267 of the first ferrule removal feature 259.

As shown in FIG. 18F, while the first ferrule removal feature 259 is maintained in the position of FIG. 18E, the actuator rod 246 may be moved in a proximal direction 322, which will cause the needle 266 to rotate in a second direction 324 (opposite the first direction 316) about its needle pivot axis. While rotating in this second direction 324, the first ferrule release feature 259 retains the ferrule 296 in the ferrule holder 288 while the ferrule engaging tip 292 of the curved arm 290 passes from its engaged position (shown in FIG. 18E), back through the tissue bite area 295 without the ferrule 296, and to the retracted position as shown in FIG. 18F. The device is now reset for another stitch with the same suture if desired.

Figure 19A:
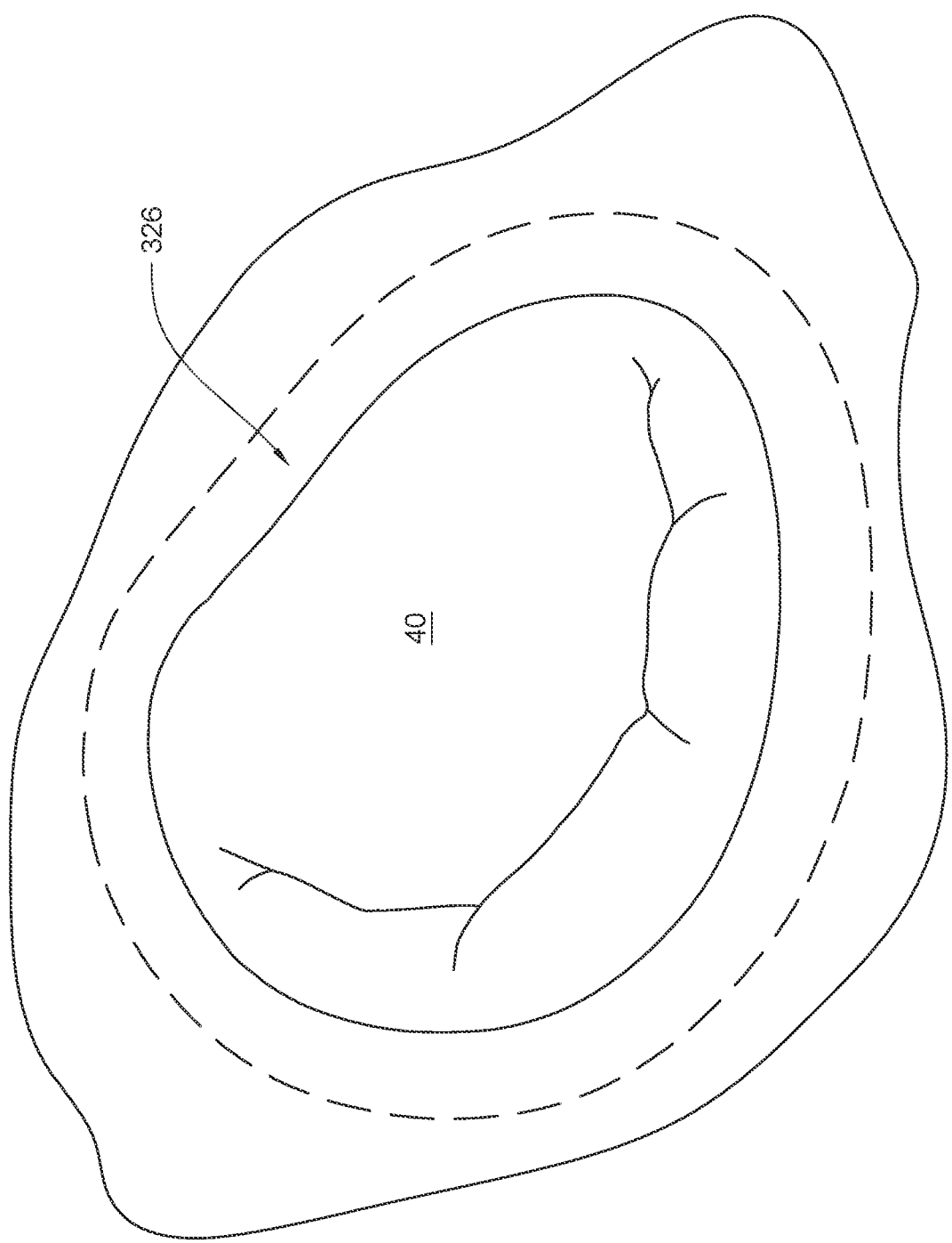
FIGS. 19A-19H illustrate a method of using an embodiment of the surgical suturing device from FIG. 14 to place a suture through an annuloplasty ring and underlying tissue.
Figure 19B:
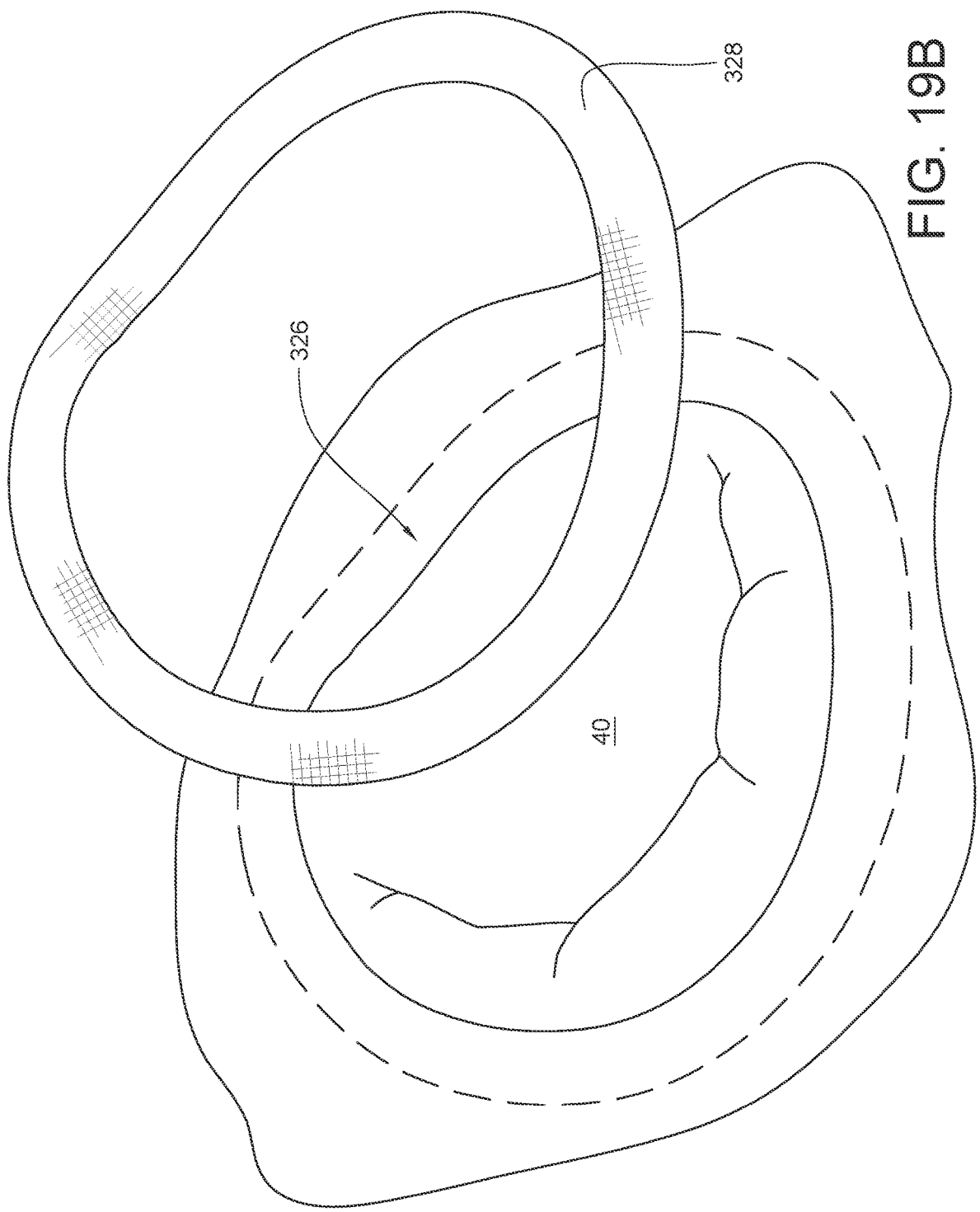
Figure 19C:
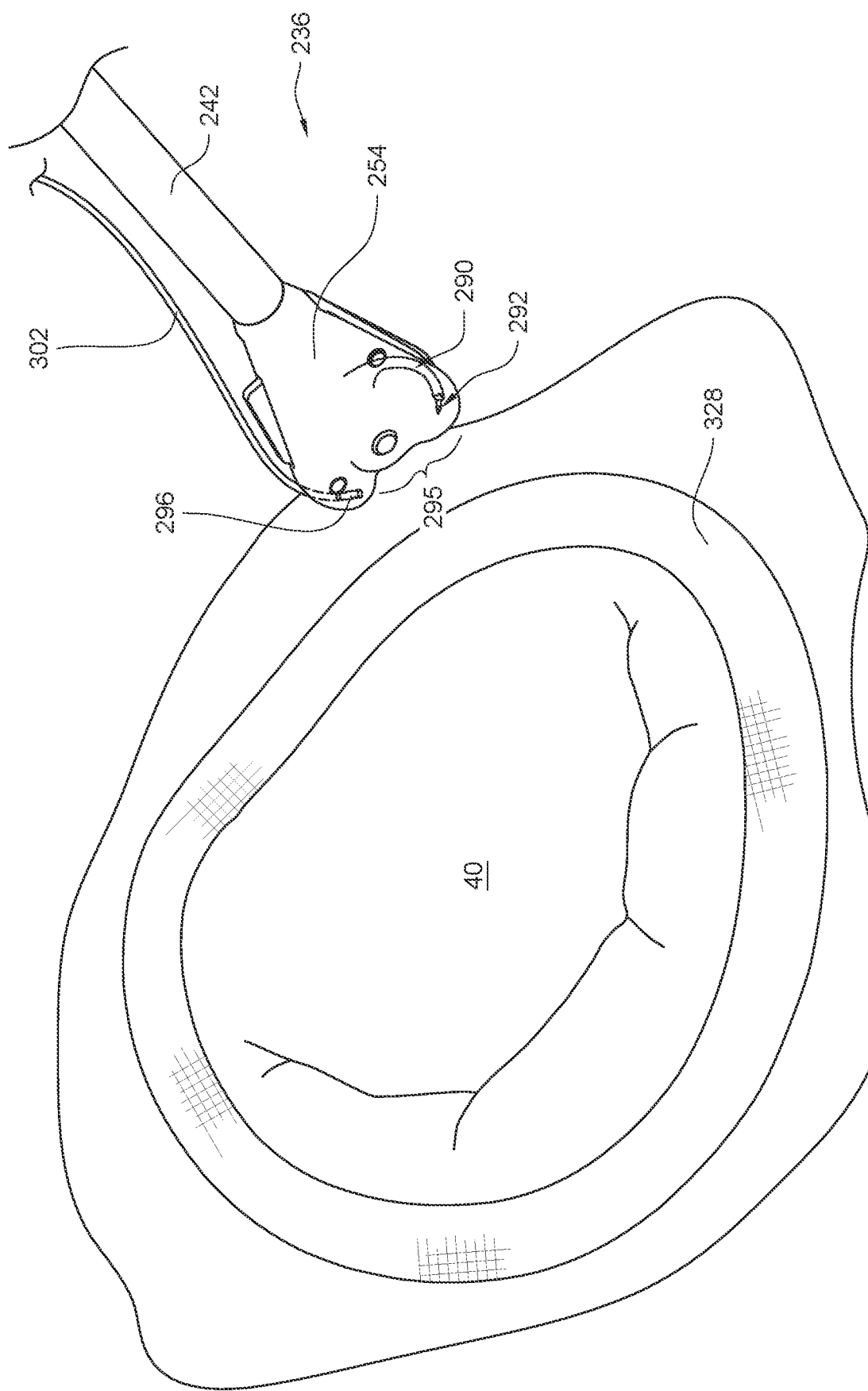

FIGS. 19A-19JE illustrate a method of using an embodiment of the surgical suturing device 236 from FIG. 14 to place a suture through an annuloplasty ring and corresponding annular tissue to help restore heart valve function. FIG. 19A schematically illustrates a surgical situation. Minimally invasive access has been gained to a chamber of the heart. Annular tissue 326 surrounding a mitral valve 40 has become enlarged and, as a result, the valve's leaflets are no longer able to maintain proper mitral valve closure. An annuloplasty ring, of a desired annulus size, may be installed over the annular tissue such that the annular tissue is snugged inward towards the prosthetic to reestablish a preferred, smaller mitral annulus. As illustrated in FIG. 19B, an annuloplasty ring 328 may be introduced into the heart and then positioned over the annular tissue 326 as shown in FIG. 19C. As also shown in FIG. 19C, the suturing device 236 is ready to be used. For convenience, the handle, actuator, and entire shaft are not shown in these views. As before, the device 236 has a bite area 295 defined at least in part by the head 254 at the end of the shaft 242. The ferrule 296, coupled to the end of suture 302 is held in the ferrule holder on one side of the bite area 295 in the device head 254. The curved arm 290 and its ferrule engaging tip 292 is in a retracted position on the other side of the bite area 295.

Figure 19D:
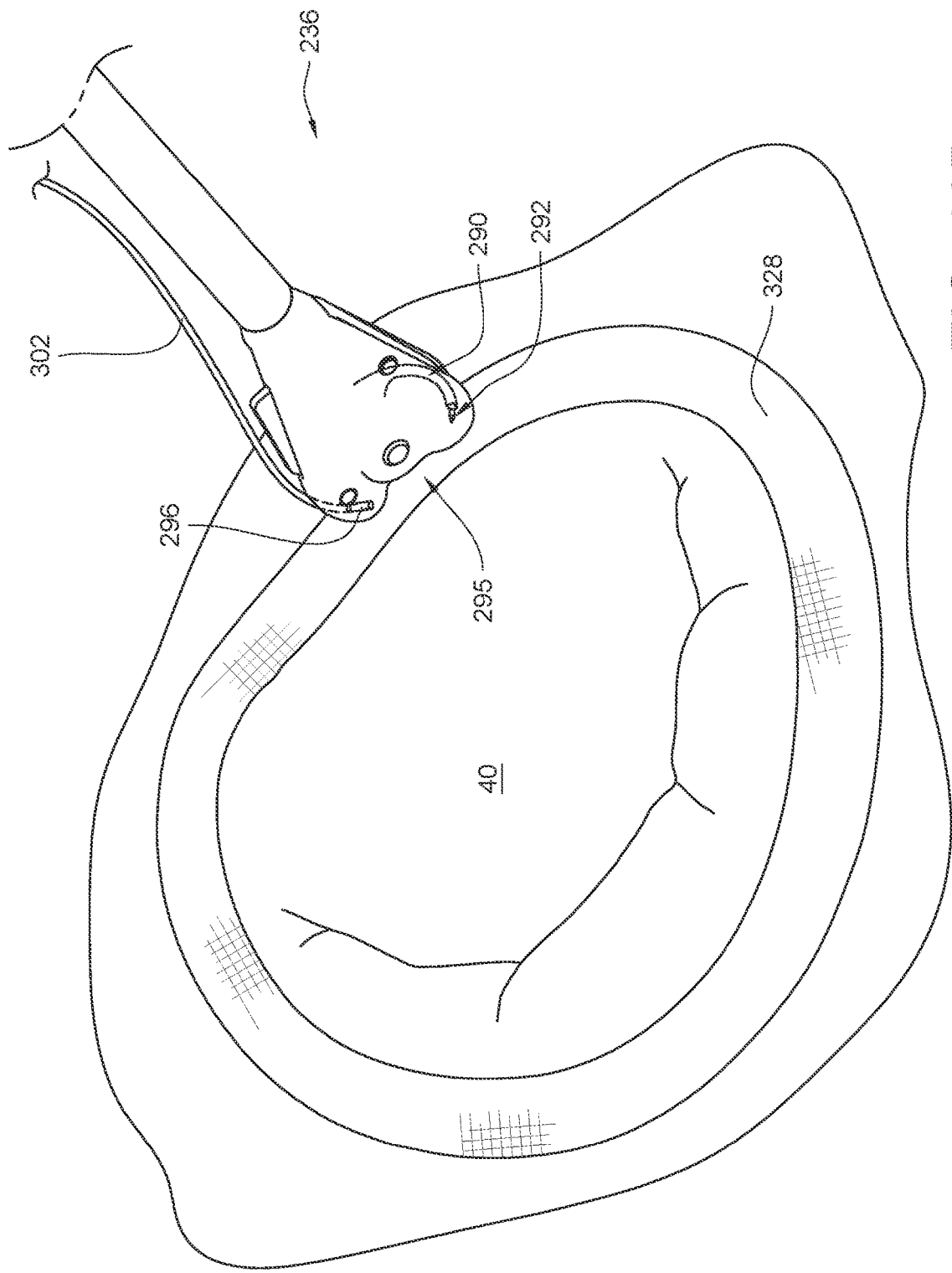
Figure 19E:
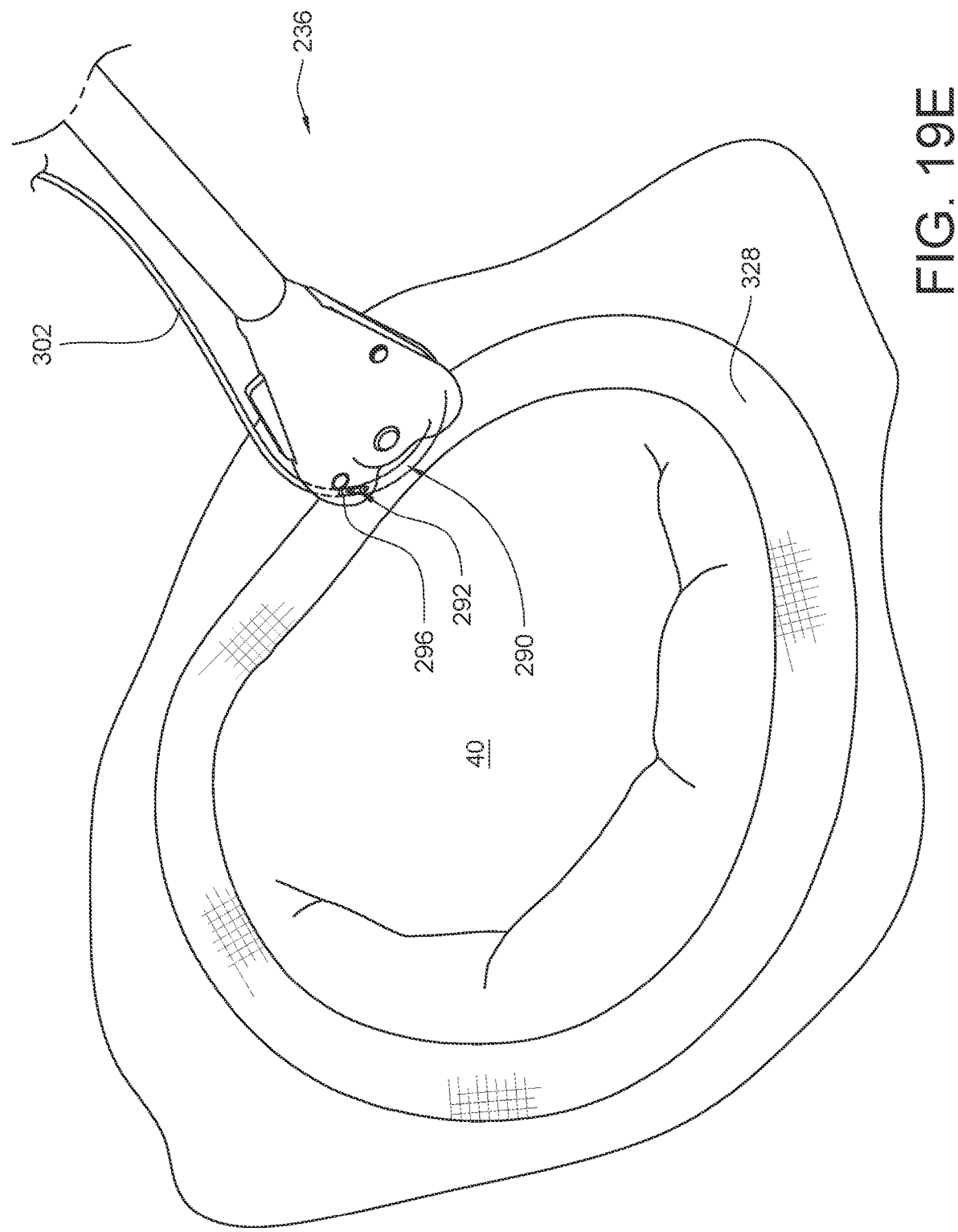
Figure 19F:
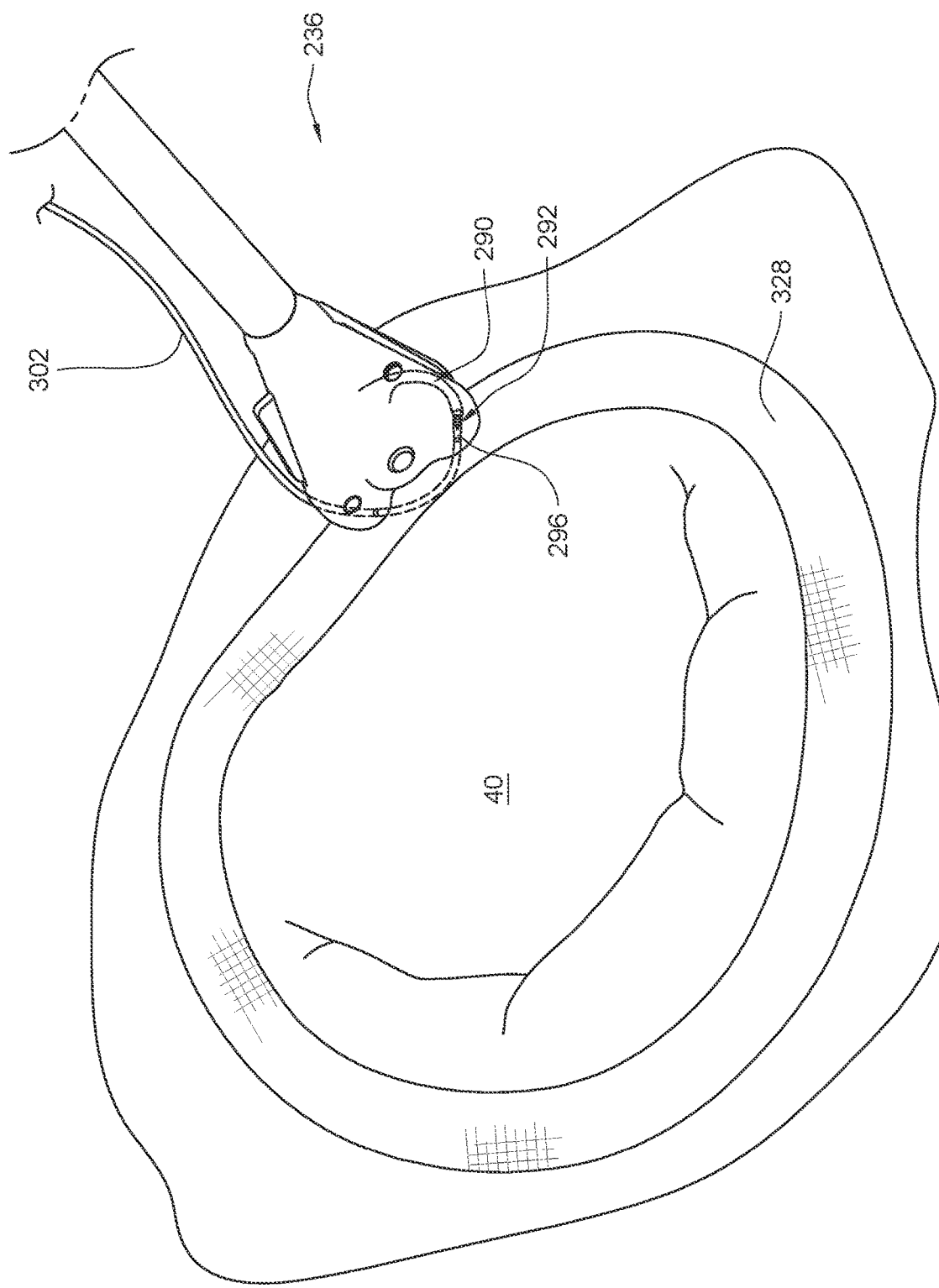
Figure 19G:
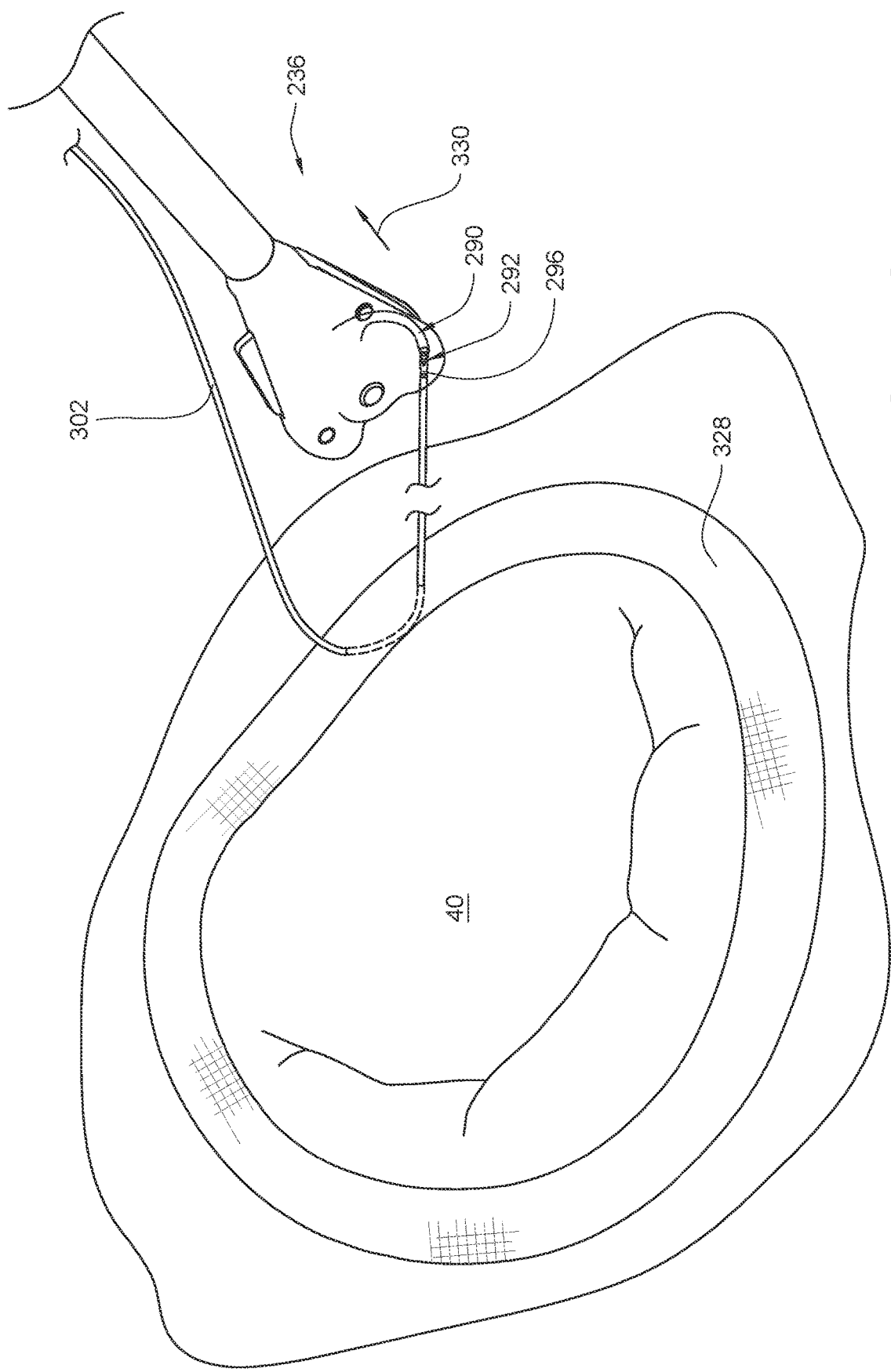
Figure 19H:
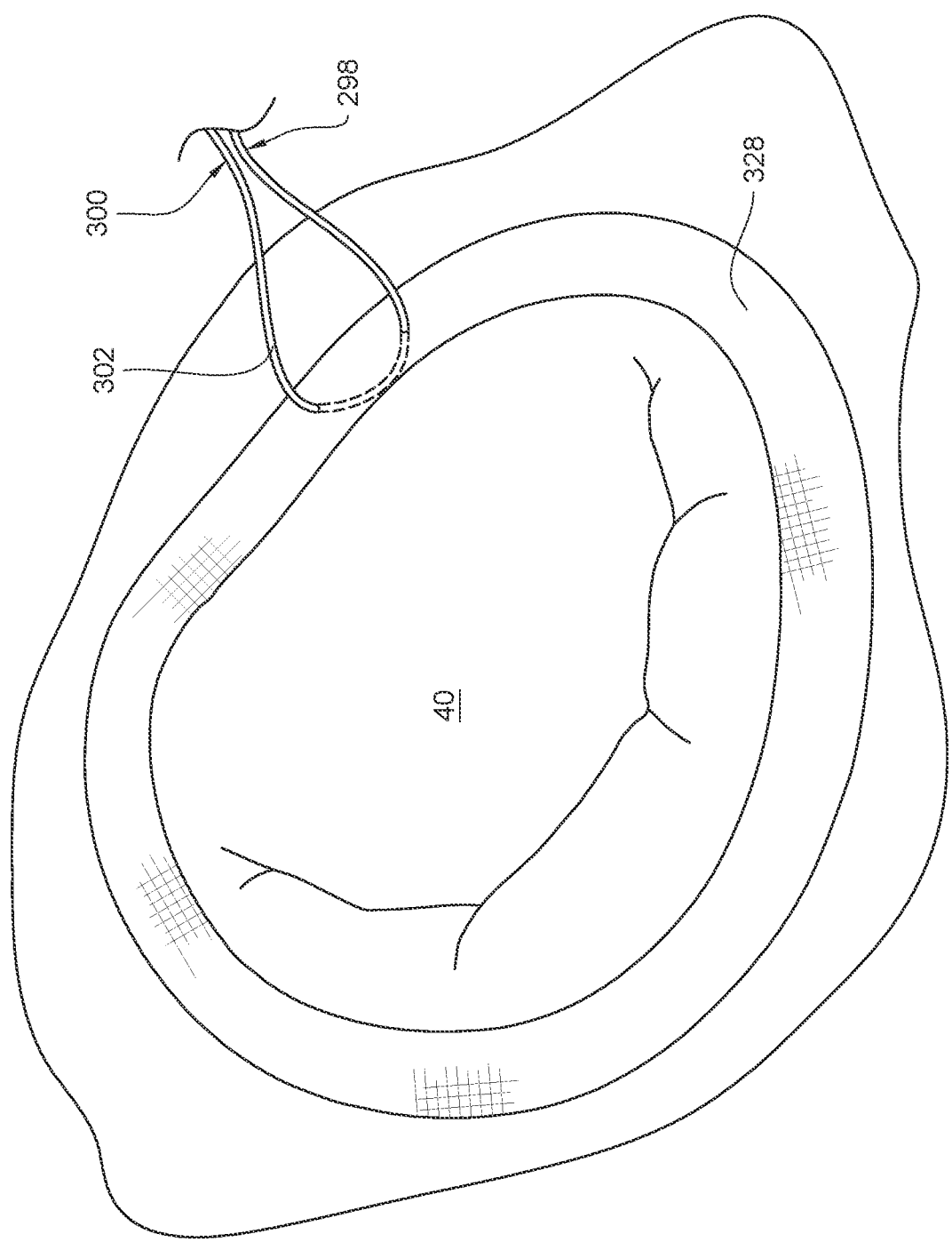
Figure 19I:
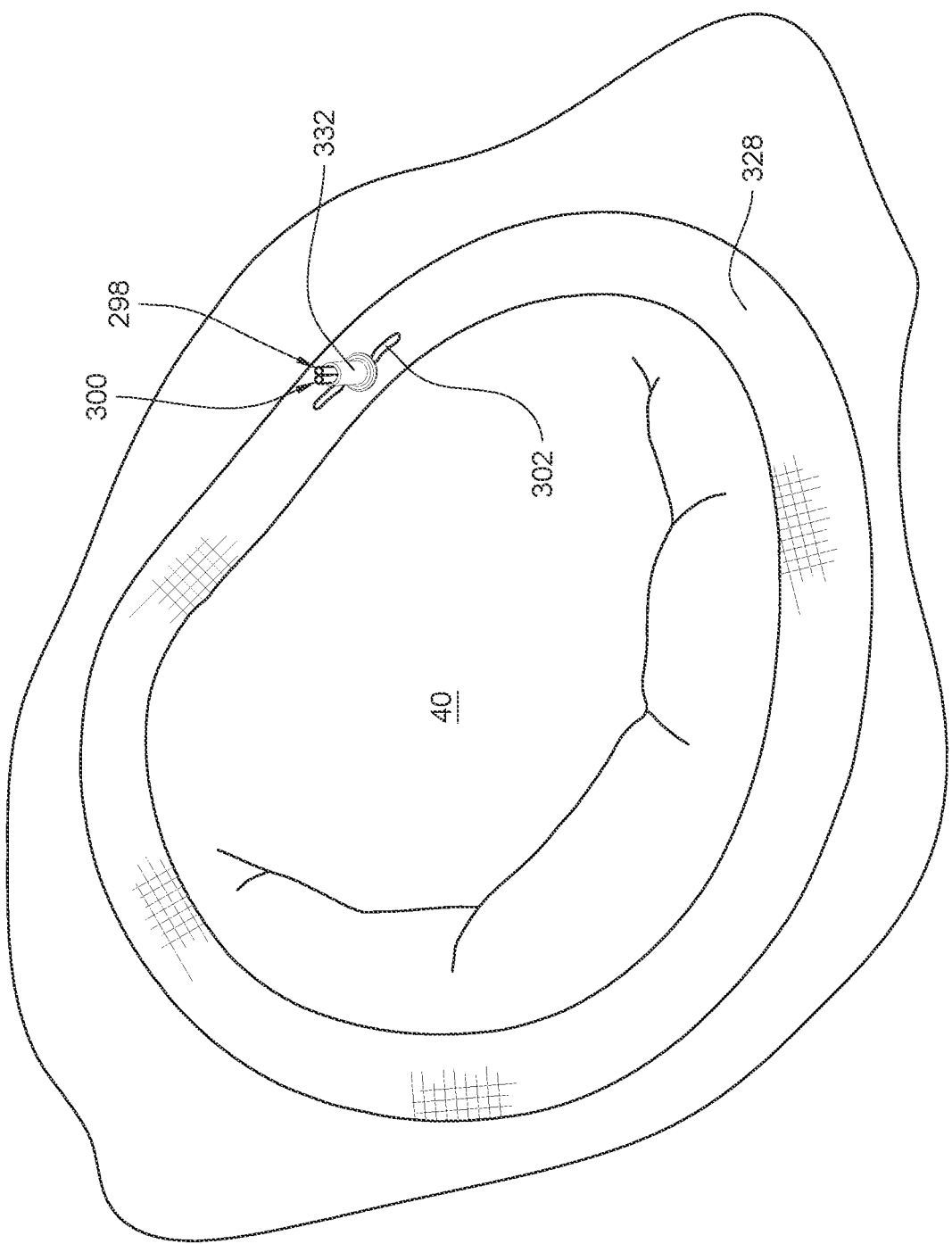

As shown in FIG. 19D, the tissue bite area 295 is placed onto the annuloplasty ring 328 which is resting on the underlying annular tissue 326. As shown in FIG. 19E, the needle is actuated so that the curved arm 290 and its ferrule engaging tip 292 pass through the annuloplasty ring 328, the underlying annular tissue, back up through the annuloplasty ring 328, and into contact with the ferrule 296. As shown in FIG. 19F, the needle is de-actuated so that the curved arm 290 and its ferrule engaging tip 292 (along with the attached ferrule 296) are pulled back through the annuloplasty ring and underlying annular tissue and into a retracted position again. Since the end of suture 302 is coupled to the ferrule 296, part of the suture 302 is also pulled through the annuloplasty ring and the annular tissue, too. As illustrated in FIG. 19G, the suturing device 236 may be pulled away 330 from the annuloplasty ring 328, thereby drawing more of the suture 302 out of the stitch. The ferrule 296 may be removed from the suture 302, leaving the suture 302 stitched through the annuloplasty ring 328 and the underlying annular tissue, with two free suture ends 298, 300 protruding from the annuloplasty ring 328 as shown in FIG. 19H. As illustrated in FIG. 19I, the loose suture ends 298, 300 may be secured with a mechanical fastener 332 to help hold the annuloplasty ring 328 in place. As illustrated in FIG. 19J, the suturing process may be repeated in multiple locations around the annuloplasty ring 328 in order to fully secure the ring 328 to the underlying tissue (for example, with mechanical fasteners 332A-332N each holding corresponding sutures 302A-302N).

Up until this point, the embodiments described herein have had a needle with a maximum of one pair of curved arms. In other embodiments, however, it is possible to have a needle with more than one pair of curved arms. For example, FIGS. 20A and 20B schematically illustrate another embodiment of a surgical suturing device in top and side views, respectively, this embodiment having a needle 334 with multiple pairs of curved arms, each pair of curved arms following an arcuate path having a different radius from the other pair. Needle 334 has a flywheel portion 336, similar to flywheel portions described previously. The needle 334 also has a first pair of curved arms 338A, 338B and a second pair of curved arms 340A, 340B. In this embodiment, the second pair of curved arms 340A, 340B are located in-between the first pair of curved arms 338A, 338B. As in previous embodiments, the needle 334 defines a needle pivot axis 342, and an actuator 344 is coupled to the needle 334 to rotate the needle 334 about the pivot axis 342. In this embodiment, when the actuator 344 is moved in a direction 346 away from the needle 334, the needle rotates in a first direction 348. As the needle 334 moves in the first direction 348, the ferrule engaging tips on each of the curved arms 338A, 338B, 340A, 340B move on an arcuate path towards corresponding ferrules 350A, 350B, 352A, 352B. The first pair of ferrules 350A, 350B are each coupled to different ends of a first suture 354, while the second pair of ferrules 352A, 352B are each coupled to different ends of a second suture 356. If the pairs of curved arms 338A, 338B, 340A, 340B are passed through tissue, engaged with their corresponding ferrules, and then rotated back to pull the first and second sutures 354, 356 through the tissue in a fashion as has been disclosed in detail above, the resultant suture placement in tissue 358 is illustrated schematically in FIGS. 21A (top view) and 21B (left side view). Each end of the first suture 354 enters and exits the tissue 358 at a distance farther from a potential incision point 360 than where the ends of the second suture 356 enter and exit the same tissue 358. Due to the difference in the arc of the first pair of curved arms 338A, 338B (larger arc) vs the second pair of curved arms 340A, 340B (smaller arc), the first suture 354 also travels deeper into the tissue 358 than the second suture 356 does. The suture stitches illustrated in FIGS. 21A and 21B are useful for setting up a purse string suture closure prior to forming an incision therebetween so that the incision may be closed and/or drawn together as needed during a surgical procedure.

FIGS. 22A and 22B schematically illustrate a further embodiment of a surgical suturing device in top and side views, respectively, this embodiment having a needle 362 with multiple pairs of curved arms, each pair of curved arms following a similar arcuate path. Needle 362 has a flywheel portion 364, similar to flywheel portions described previously. The needle 362 also has a first pair of curved arms 366A, 366B and a second pair of curved arms 368A, 368B. In this embodiment, the second pair of curved arms 368A, 368B are located in-between the first pair of curved arms 366A, 366B. As in previous embodiments, the needle 362 defines a needle pivot axis 370, and an actuator 372 is coupled to the needle 362 to rotate the needle 362 about the pivot axis 370. In this embodiment, when the actuator 372 is moved in a direction 374 away from the needle 362, the needle rotates in a first direction 376. As the needle 362 moves in the first direction 376, the ferrule engaging tips on each of the curved arms 366A, 366B, 368A, 368B move on an arcuate path towards corresponding ferrules 378A, 378B, 380A, 380B. The first pair of ferrules 378A, 378B are each coupled to different ends of a first suture 382, while the second pair of ferrules 380A, 380B are each coupled to different ends of a second suture 384. If the pairs of curved arms 366A, 366B, 368A, 368B are passed through tissue, engaged with their corresponding ferrules, and then rotated back to pull the first and second sutures 382, 384 through the tissue in a fashion as has been disclosed in detail above, the resultant suture placement in tissue 386 is illustrated schematically in FIGS. 23A (top view) and 23B (left side view). Each end of the first suture 382 enters and exits the tissue 386 at a distance farther from a potential incision point 388 than where the ends of the second suture 384 enter and exit the same tissue 386. Unlike the previous embodiment, however, since the arc of the first pair of curved arms 366A, 366B and the arc of the second pair of curved arms 368A, 368B are substantially the same, the first and second sutures 382, 384 each travel the same depth into the tissue 386. The suture stitches illustrated in FIGS. 23A and 23B are useful for setting up a purse string suture closure prior to forming an incision therebetween so that the incision may be closed and/or drawn together as needed during a surgical procedure.

Figure 24A:
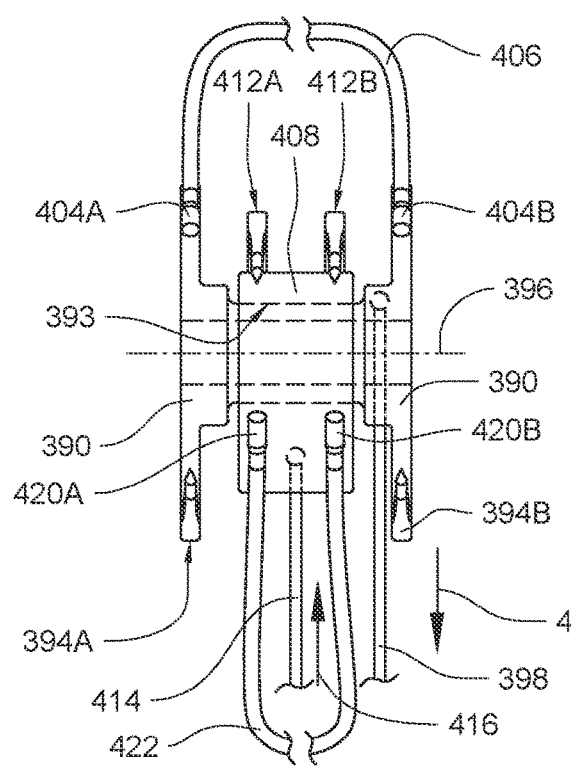
FIGS. 24A and 24B schematically illustrate another embodiment of a surgical suturing device in top and side views, respectively, this embodiment having a plurality of needles, each needle having a pair of curved arms configured to engage in a direction opposite the other pair and following paths having a different radius from the other pair.
Figure 24B:
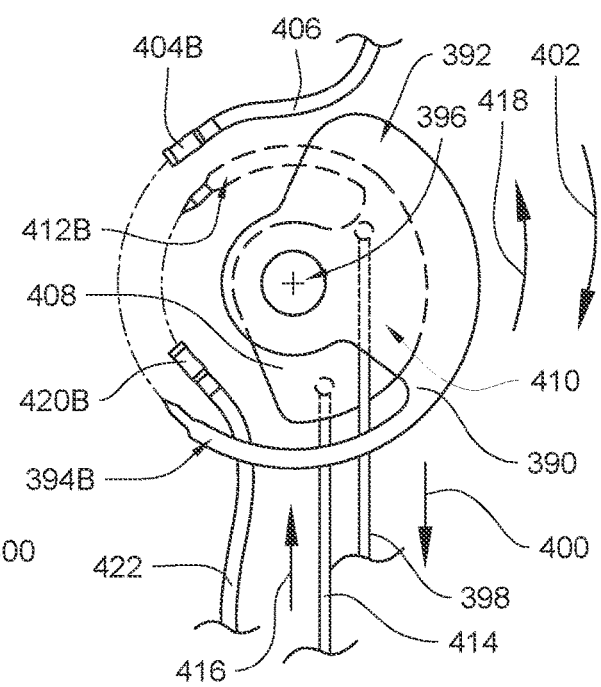

Up until this point, the embodiments described herein have had a single needle with a varying number of curved arms. In other embodiments, however, it is possible to have multiple needles. For example, FIGS. 24A and 24B schematically illustrate another embodiment of a surgical suturing device in top and side views, respectively, this embodiment having multiple needles 390 and 408. First needle 390 has a flywheel portion 392, similar to flywheel portions described previously. The first needle 390 also has a bushing surface 393 coupled to or formed as part of the flywheel portion 392 and configured to provide a surface for the second needle 408 to rotate about. The first needle 390 also has a pair of curved arms 394A, 394B. As in previous embodiments, the first needle 390 defines a needle pivot axis 396, and a first actuator rod 398 is coupled to the first needle 390 to rotate the needle 390 about the pivot axis 396. In this embodiment, when the first actuator rod 398 is moved in a direction 400 away from the first needle 390, the first needle 390 rotates in a first direction 402. As the first needle 390 moves in the first direction 402, the ferrule engaging tips on each of the curved arms 394A, 394B move on an arcuate path towards corresponding ferrules 404A, 404B. The first pair of ferrules 404A, 404B are each coupled to different ends of a first suture 406.

Similarly, second needle 408 has a flywheel portion 410, similar to flywheel portions described previously. The second needle 408 also has a pair of curved arms 412A, 412B. As in previous embodiments, the second needle 408 defines a needle pivot axis 396, but in this embodiment, the second needle 408 pivots about the bushing surface 393 of the first needle 390. A second actuator rod 414 is coupled to the second needle 408 to rotate the second needle 408 about the bushing surface 393, and therefore, about pivot axis 396. In this embodiment, when the second actuator rod 414 is moved in a direction 416 toward the second needle 408, the second needle 408 rotates in a second direction 418. As the second needle 408 moves in the second direction 418, the ferrule engaging tips on each of the curved arms 412A, 412B move on an arcuate path towards corresponding ferrules 420A, 420B. This second pair of ferrules 412A, 412B are each coupled to different ends of a second suture 422.

Figure 25B:
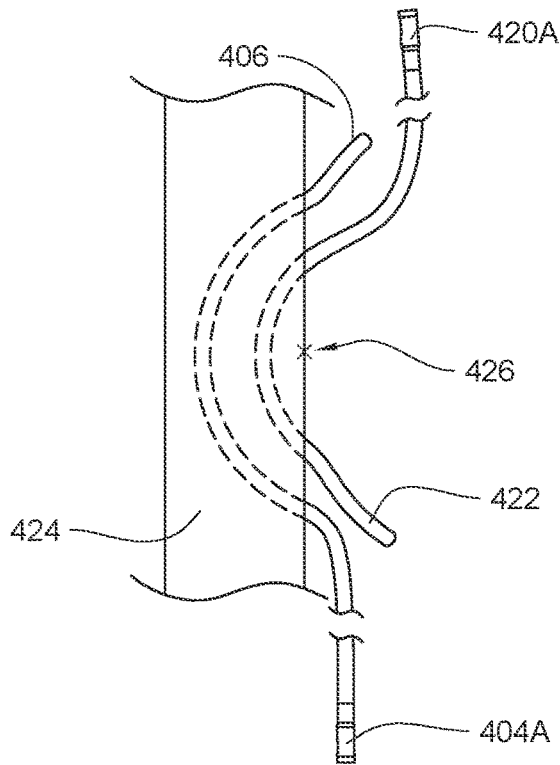
FIGS. 25A and 25B schematically illustrate a resultant placement of sutures in tissue from the surgical suturing device of FIGS. 24A and 24B.
Figure 25A:
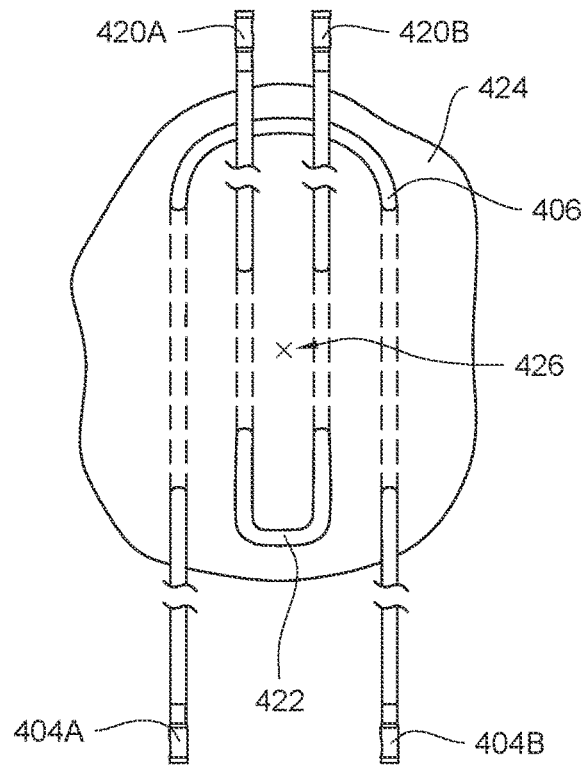

If each pair of curved arms 394A, 394B and 412A, 412B are passed through tissue (in this embodiment, in opposite directions), engaged with their corresponding ferrules, and then rotated back to pull the first and second sutures 406, 422 through the tissue in a fashion as has been disclosed in detail above, the resultant suture placement in tissue 424 is illustrated schematically in FIGS. 25A (top view) and 25B (left side view). Each end of the first suture 406 enters and exits the tissue 424 at a distance farther from a potential incision point 426 than where the ends of the second suture 422 enter and exit the same tissue 424. Due to the difference in the arc of the first pair of curved arms 394A, 394B (larger arc) vs the second pair of curved arms 412A, 412B (smaller arc), the first suture 406 also travels deeper into the tissue 424 than the second suture 422 does. The ends of the placed sutures 406, 422 also face in opposite directions in this embodiment.

The suture stitches illustrated in FIGS. 25A and 25B are useful for setting up a purse string suture closure prior to forming an incision therebetween so that the incision may be closed and/or drawn together as needed during a surgical procedure.

Figures 26A, 26B:
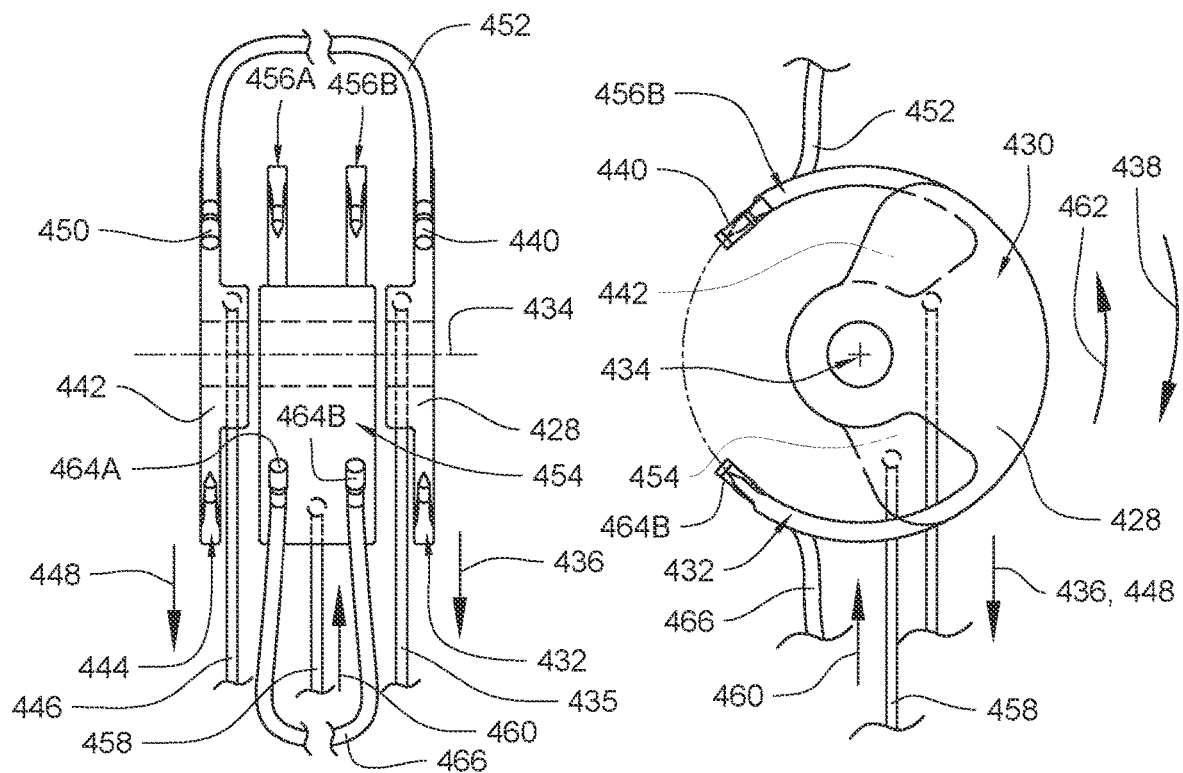
FIGS. 26A and 26B schematically illustrate a further embodiment of a surgical suturing device in top and side views, respectively, this embodiment having a plurality of needles, including a central needle having a pair of curved arms and two outer needles, each outer needle having its own curved arm configured to engaging in a direction opposite from the pair of curved arms on the central needle, but having substantially the same radius.

FIGS. 26A and 26B schematically illustrate a further embodiment of a surgical suturing device in top and side views, respectively, this embodiment having multiple needles 428, 442, and 454. First needle 428 has a flywheel portion 430, similar to flywheel portions described previously. The first needle 428 has a single curved arm 432. As in previous embodiments, the first needle 428 defines a needle pivot axis 434, and a first actuator rod 435 is coupled to the first needle 428 to rotate the needle 428 about the pivot axis 434. In this embodiment, when the first actuator rod 435 is moved in a direction 436 away from the first needle 428, the first needle 428 rotates in a first direction 438. As the first needle 428 moves in the first direction 438, the ferrule engaging tip on the curved arm 432 moves on an arcuate path towards corresponding ferrule 440.

Second needle 442 has a flywheel portion (not easily visible in this view), similar to flywheel portions described previously. The second needle 442 has a single curved arm 444. As in previous embodiments, the second needle 442 defines a needle pivot axis 434, and a second actuator rod 446 is coupled to the second needle 442 to rotate the needle 442 about the pivot axis 434. In this embodiment, when the second actuator rod 446 is moved in a direction 448 away from the second needle 442, the second needle 442 rotates in the first direction 438. As the second needle 442 moves in the first direction 438, the ferrule engaging tip on the curved arm 444 moves on an arcuate path towards corresponding ferrule 450. The first pair of ferrules 440, 450 are each coupled to different ends of a first suture 452.

Third needle 454 has a flywheel portion (not easily visible in this view), similar to flywheel portions described previously. The third needle 454 also has a pair of curved arms 456A, 456B. As in previous embodiments, the third needle 454 defines a needle pivot axis 434. A third actuator rod 458 is coupled to the third needle 454 to rotate the third needle 454 about pivot axis 434. In this embodiment, when the third actuator rod 458 is moved in a direction 460 toward the third needle 454, the third needle 454 rotates in a second direction 462. As the third needle 454 moves in the second direction 462, the ferrule engaging tips on each of the curved arms 456A, 456B move on an arcuate path towards corresponding ferrules 464A, 464B. This second pair of ferrules 464A, 464B are each coupled to different ends of a second suture 466.

Figures 27A, 27B:
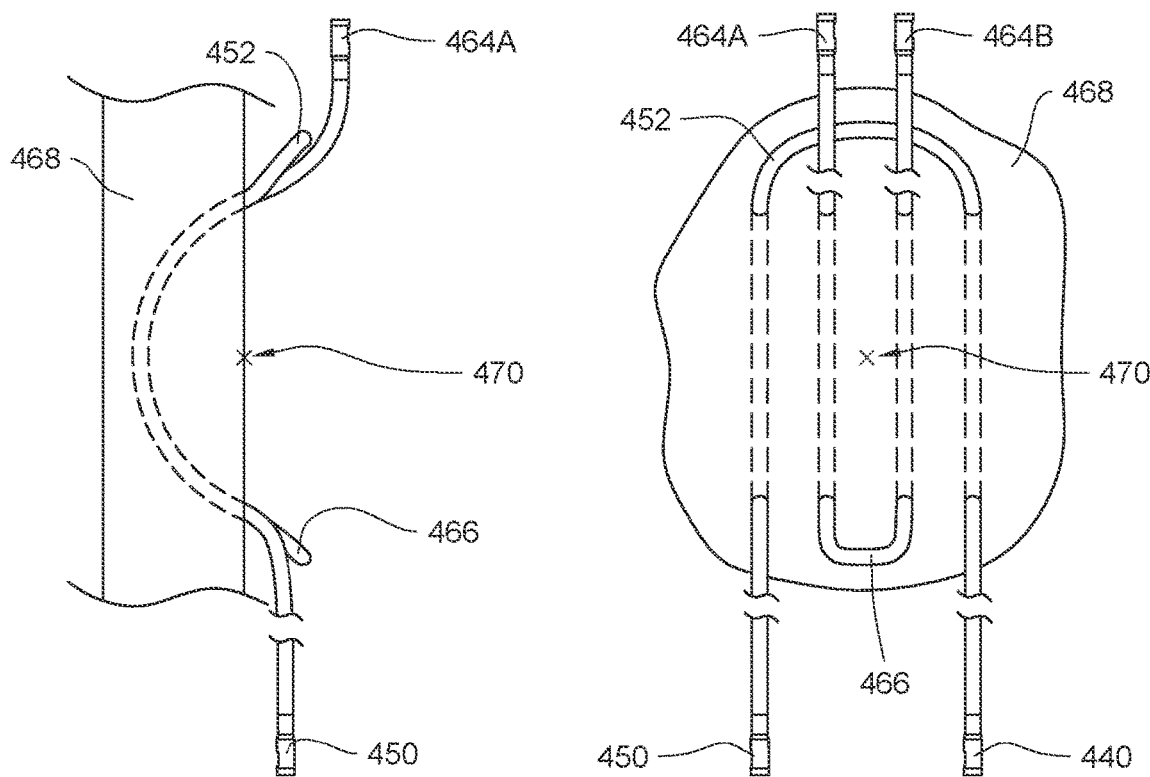
FIGS. 27A and 27B schematically illustrate a resultant placement of sutures in tissue from the surgical suturing device of FIGS. 26A and 26B.

If each pair of curved arms 332, 444 and 456A, 456B are passed through tissue (in this embodiment, in opposite directions), engaged with their corresponding ferrules, and then rotated back to pull the first and second sutures 452, 466 through the tissue in a fashion as has been disclosed in detail above, the resultant suture placement in tissue 468 is illustrated schematically in FIGS. 27A (top view) and 27B (left side view). Each end of the first suture 452 enters and exits the tissue 468 at a distance farther from a potential incision point 470 than where the ends of the second suture 466 enter and exit the same tissue 468. The ends of the placed sutures 452, 466 also face in opposite directions in this embodiment. Unlike the previous embodiment, however, since the arc of the first pair of curved arms 432, 444 and the arc of the second pair of curved arms 456A, 456B are substantially the same, the first and second sutures 452, 466 each travel the same depth into the tissue 468. The suture stitches illustrated in FIGS. 27A and 27B are useful for setting up a purse string suture closure prior to forming an incision therebetween so that the incision may be closed and/or drawn together as needed during a surgical procedure.

Figure 28A:
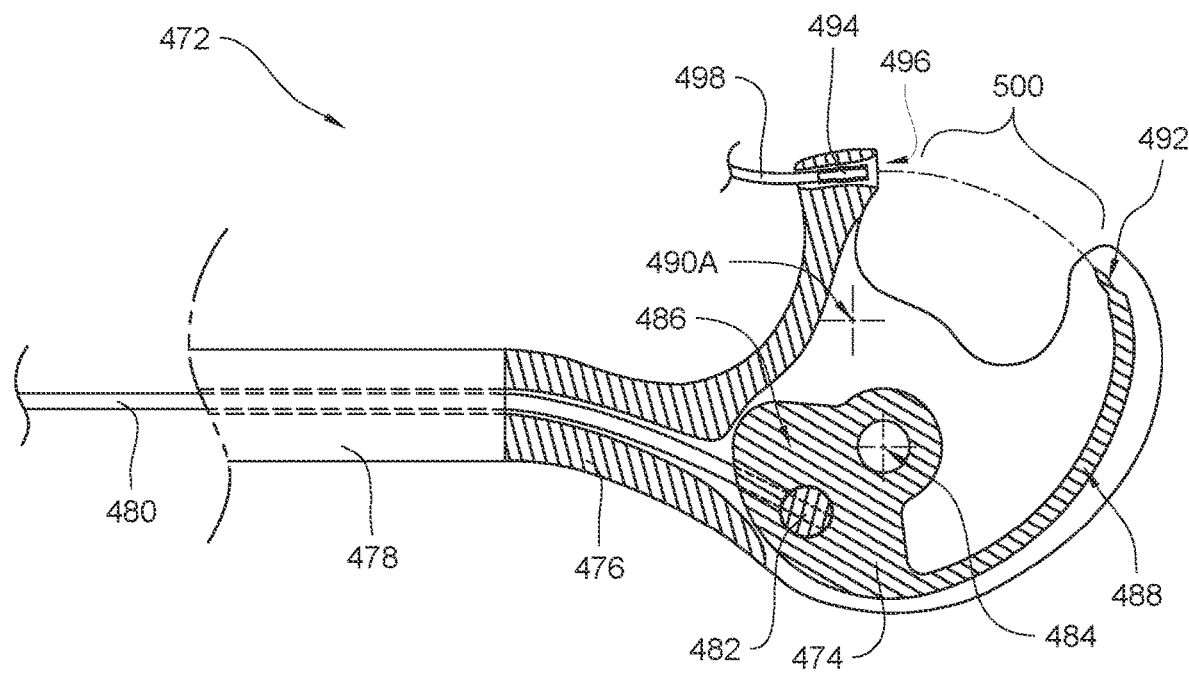
FIGS. 28A and 28B illustrate another embodiment of a surgical suturing device having a needle with one or more curved arms whereby the pivot axis of the needle and the centerpoint of the arc of the curved arms do not coincide.
Figure 28B:
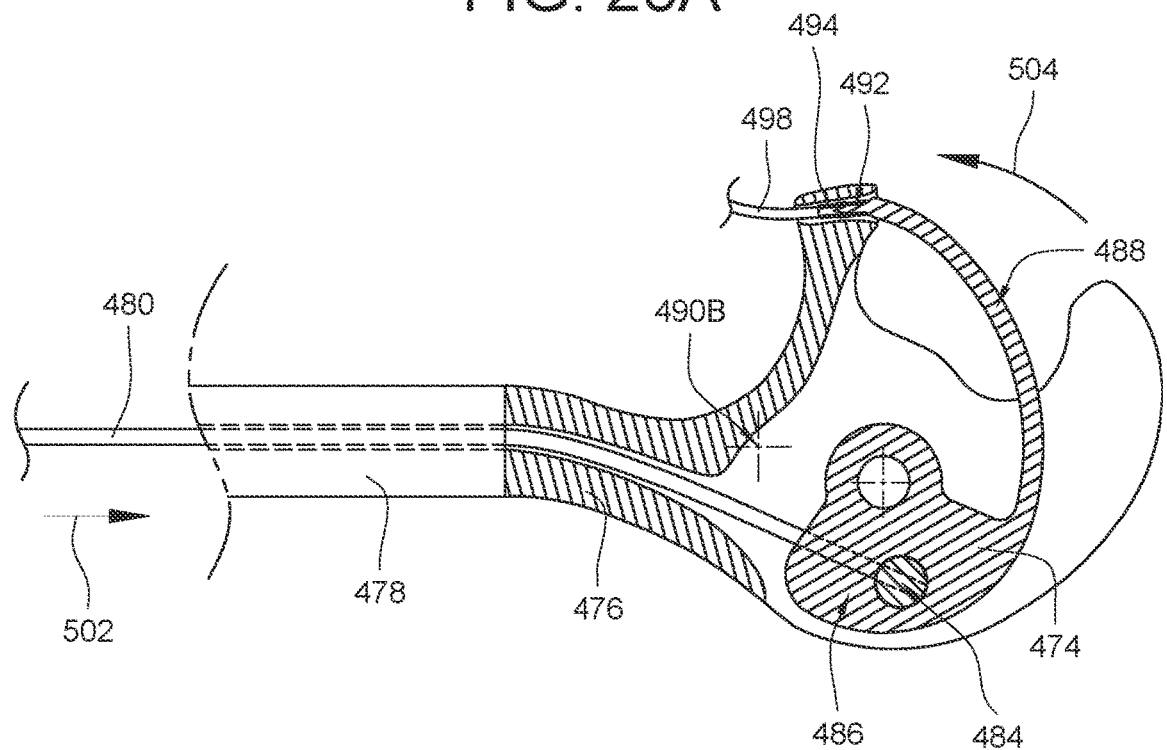

FIGS. 28A and 28B illustrate another embodiment of a surgical suturing device 472 having a needle 474 rotatable within a head 476. As with previous embodiments, the head 476 is coupled to a shaft 478, and an actuator 480 is coupled to the needle 474 by an actuator end effector 482. The needle 474 defines a pivot axis 484, and the needle 474 also has a flywheel portion 486, similar to flywheel portions discussed previously. In this embodiment, however, the one or more curved arms 488 of the needle 474 have an arc centerpoint 490A which does not coincide with the needle pivot axis 484. Each of the one or more curved arms 488 has a ferrule engaging tip 492 which is sized to engage and pick up a corresponding ferrule 494 held by the ferrule holder 496 in the device head 476. As before, the ferrule 494 may be coupled to a suture 498. The device head 476, in conjunction with the flywheel portion of the needle 474, define a bite area 500 as shown in FIG. 28A.

As illustrated in FIG. 28B, in this embodiment, when the actuator rod 502 is moved 502 towards the head 476, the needle 474 rotates in a first direction 504 about the needle axis 484. The ferrule engaging tip 492 can pick up the ferrule 494 as in previous embodiments, but in this embodiment, it should be noted that the arc centerpoint 490B is in a new location when the curved arm is engaged because the arc centerpoint (490A in FIG. 28A, and 490B in FIG. 28B) does not coincide with the needle axis 484. While this embodiment may not be preferred for some applications since the curved arm 488 will tend to pull at tissue in the bite area 500, it is another possible embodiment.

Figure 29A:
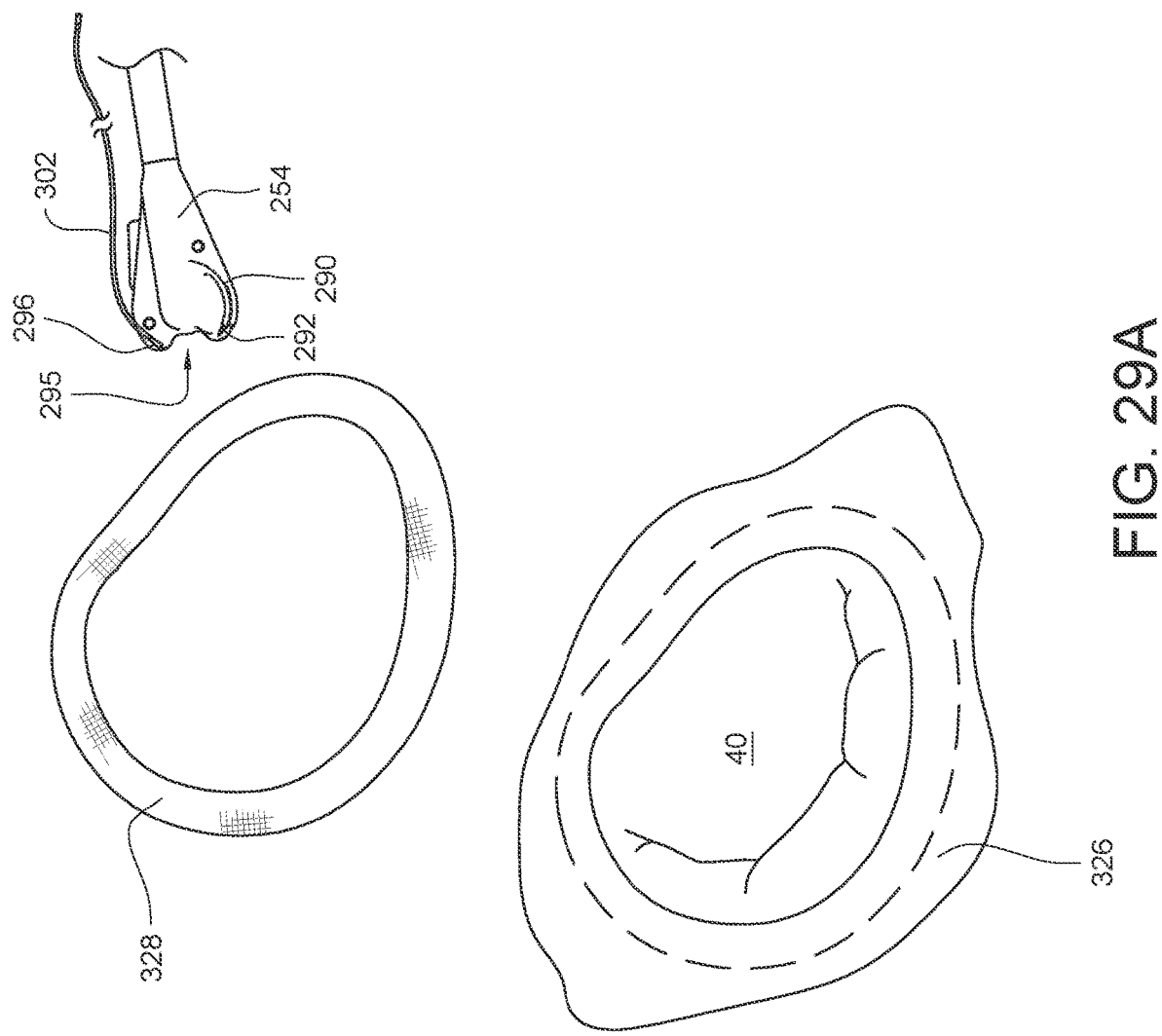
FIGS. 29A-29N illustrate another method of suturing an annuloplasty ring to underlying tissue using the surgical suturing device of FIG. 14.
Figure 29B:
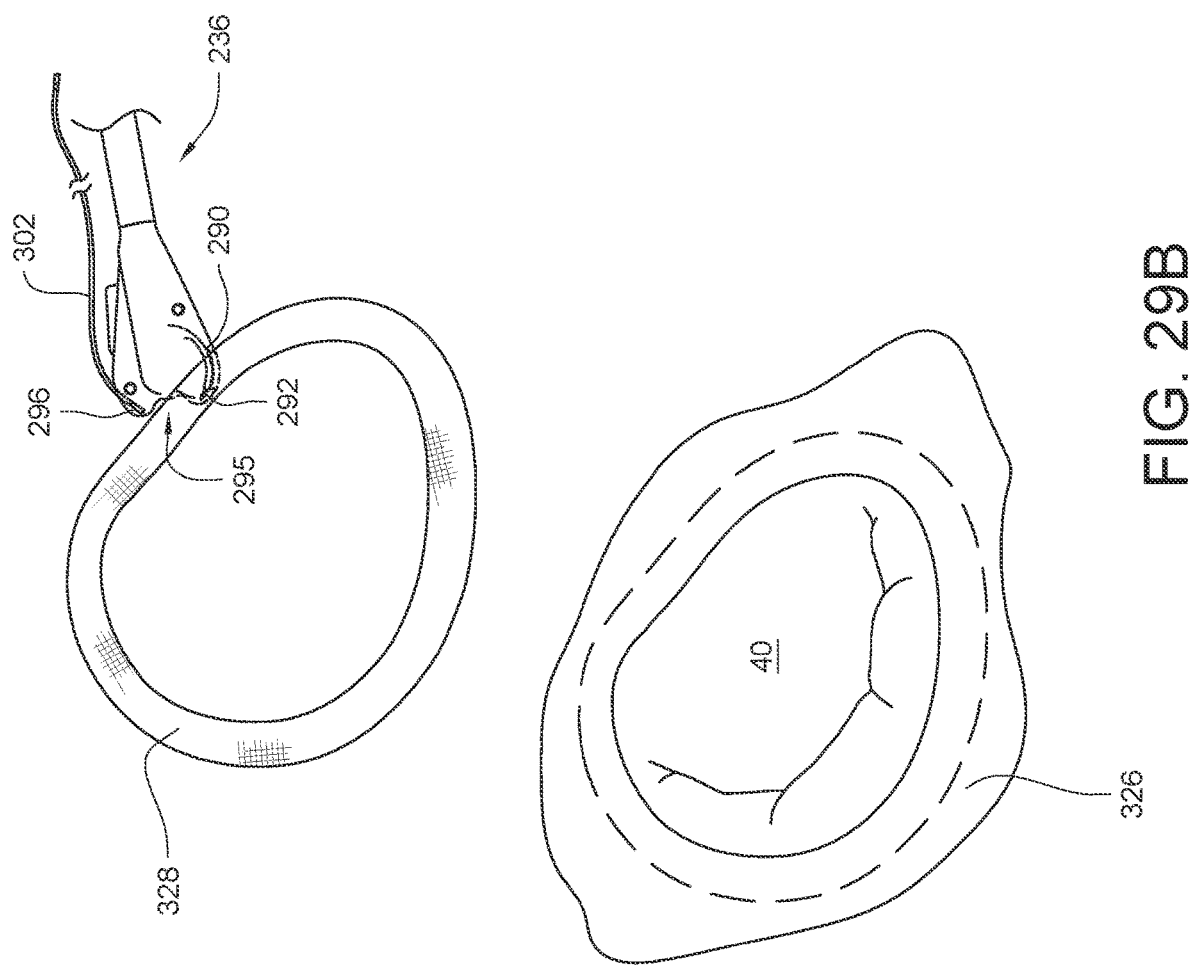
Figure 29C:
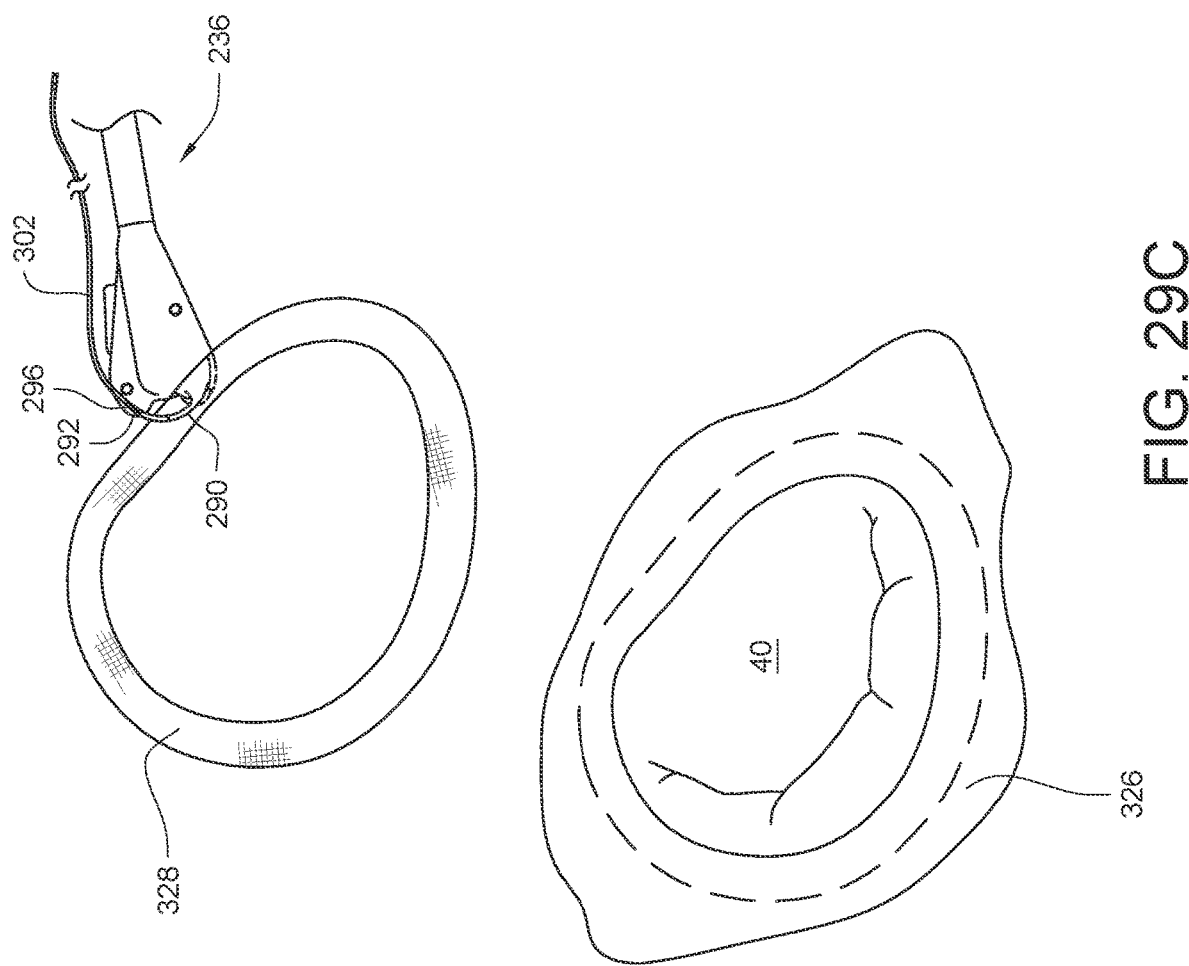
Figure 29E:
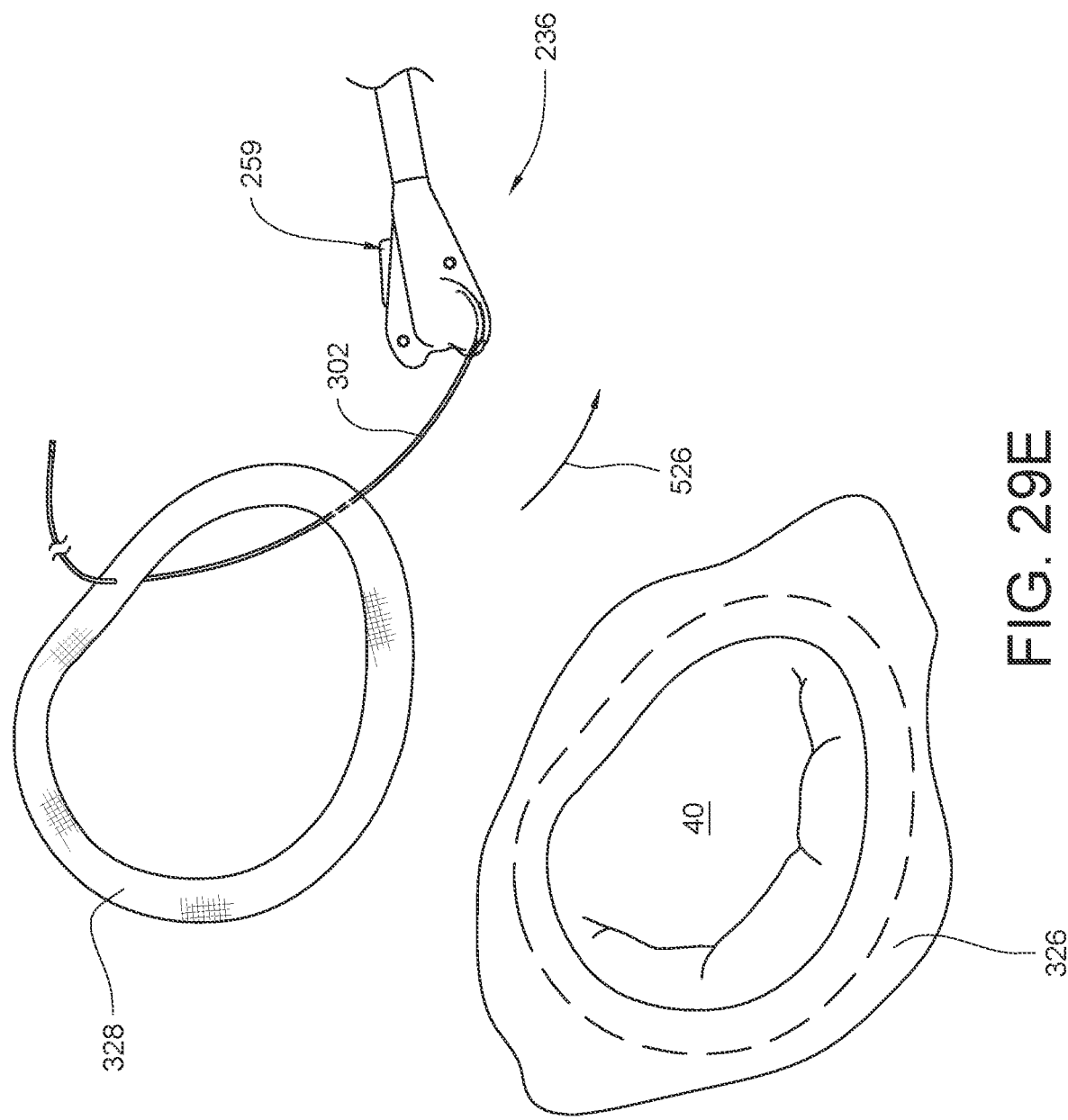
Figure 29F:
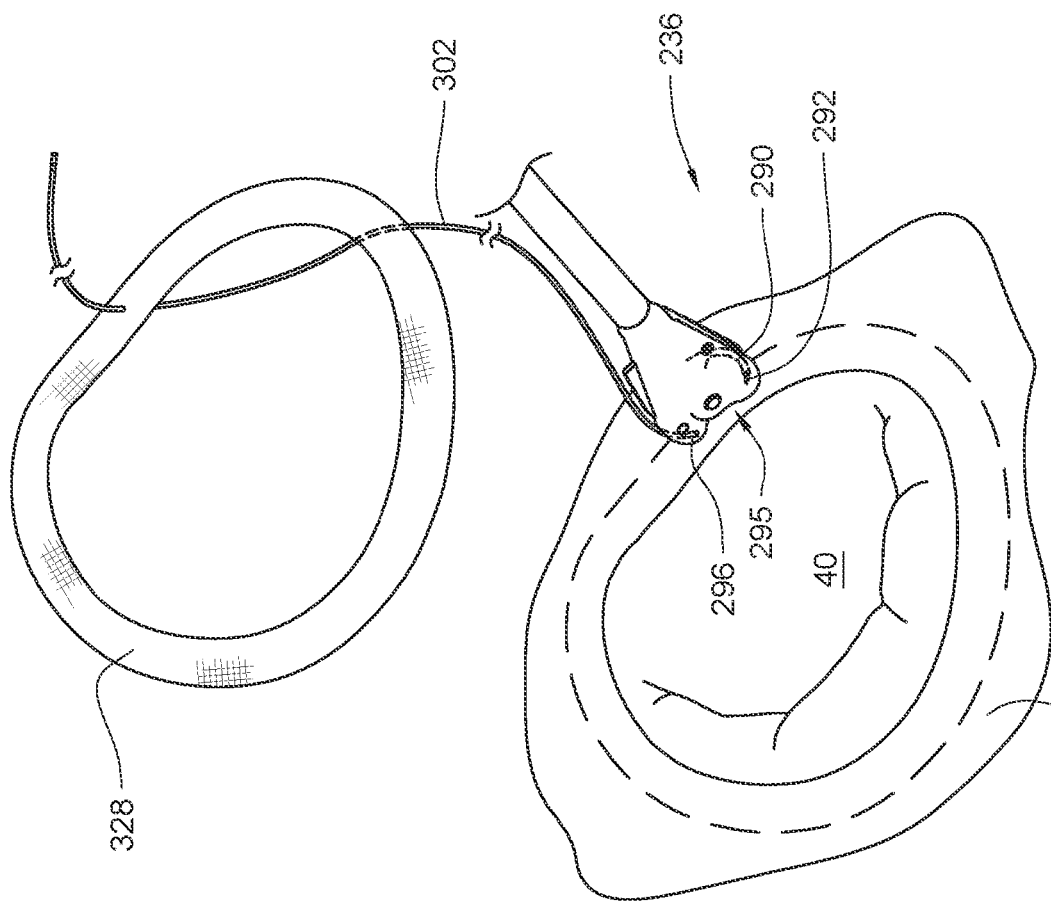
Figure 29G:
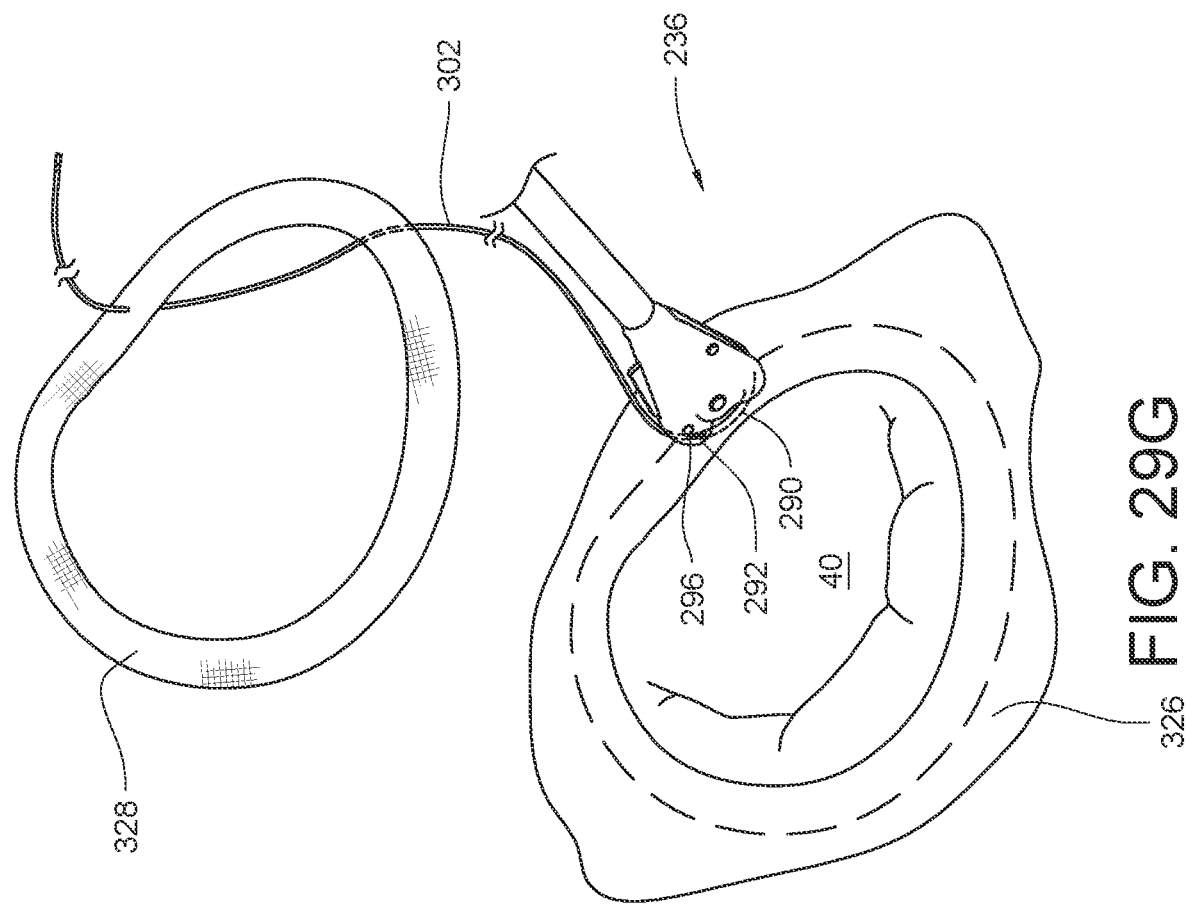
Figure 29H:
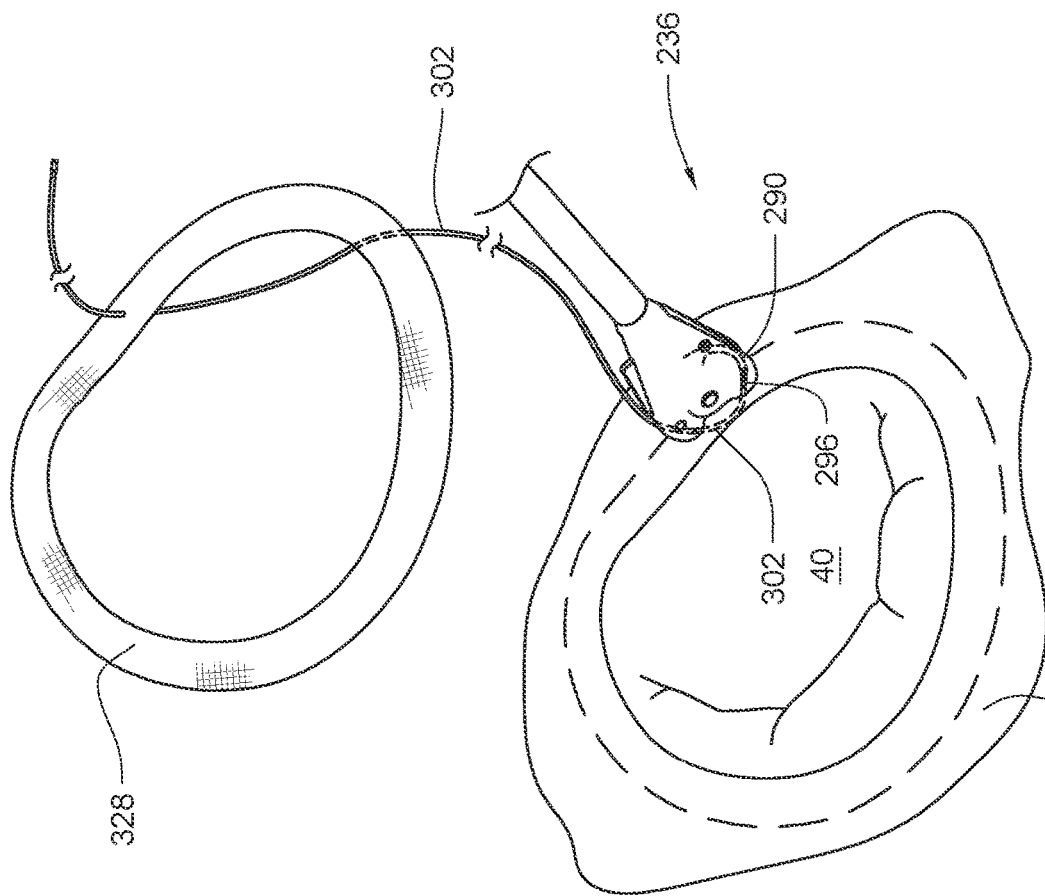
Figure 29I:
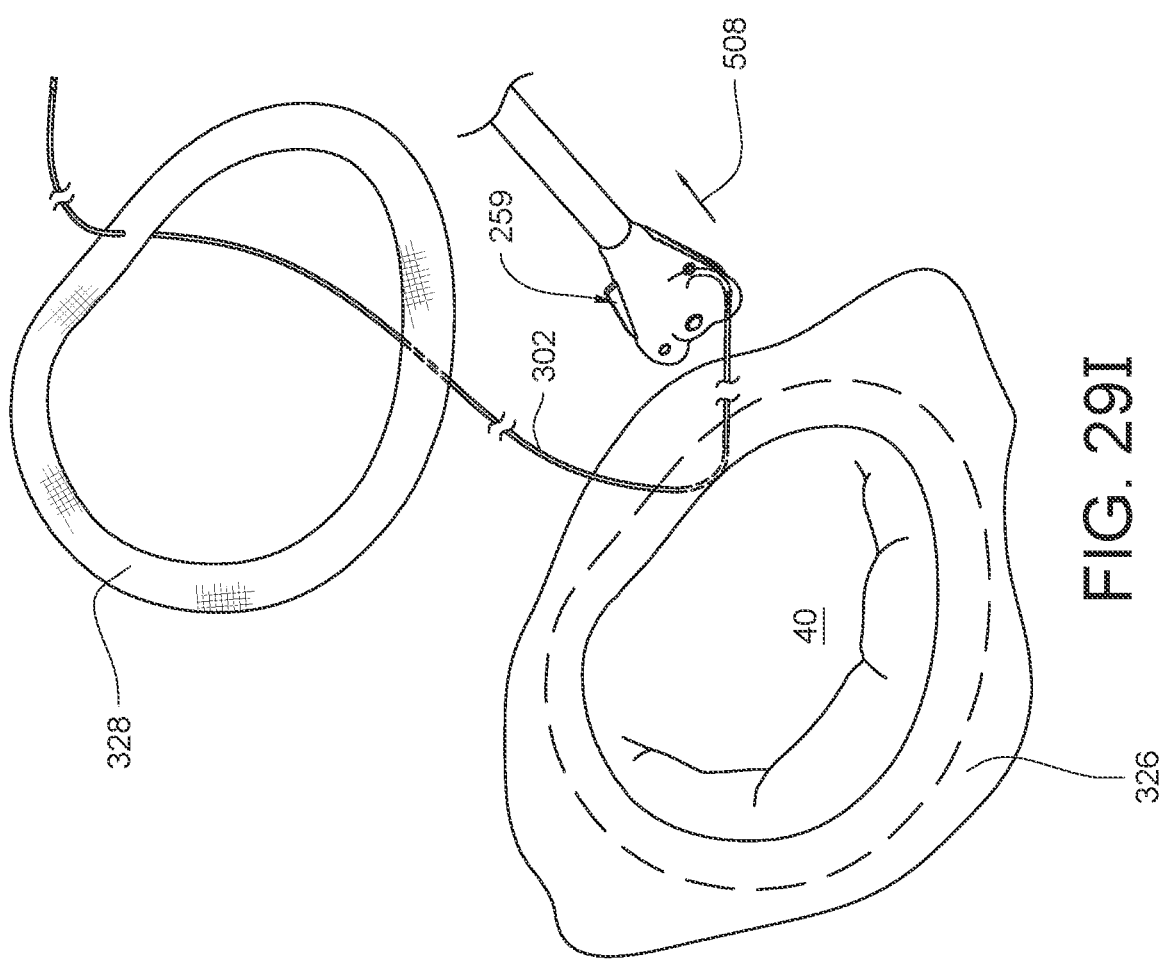
Figure 29J:
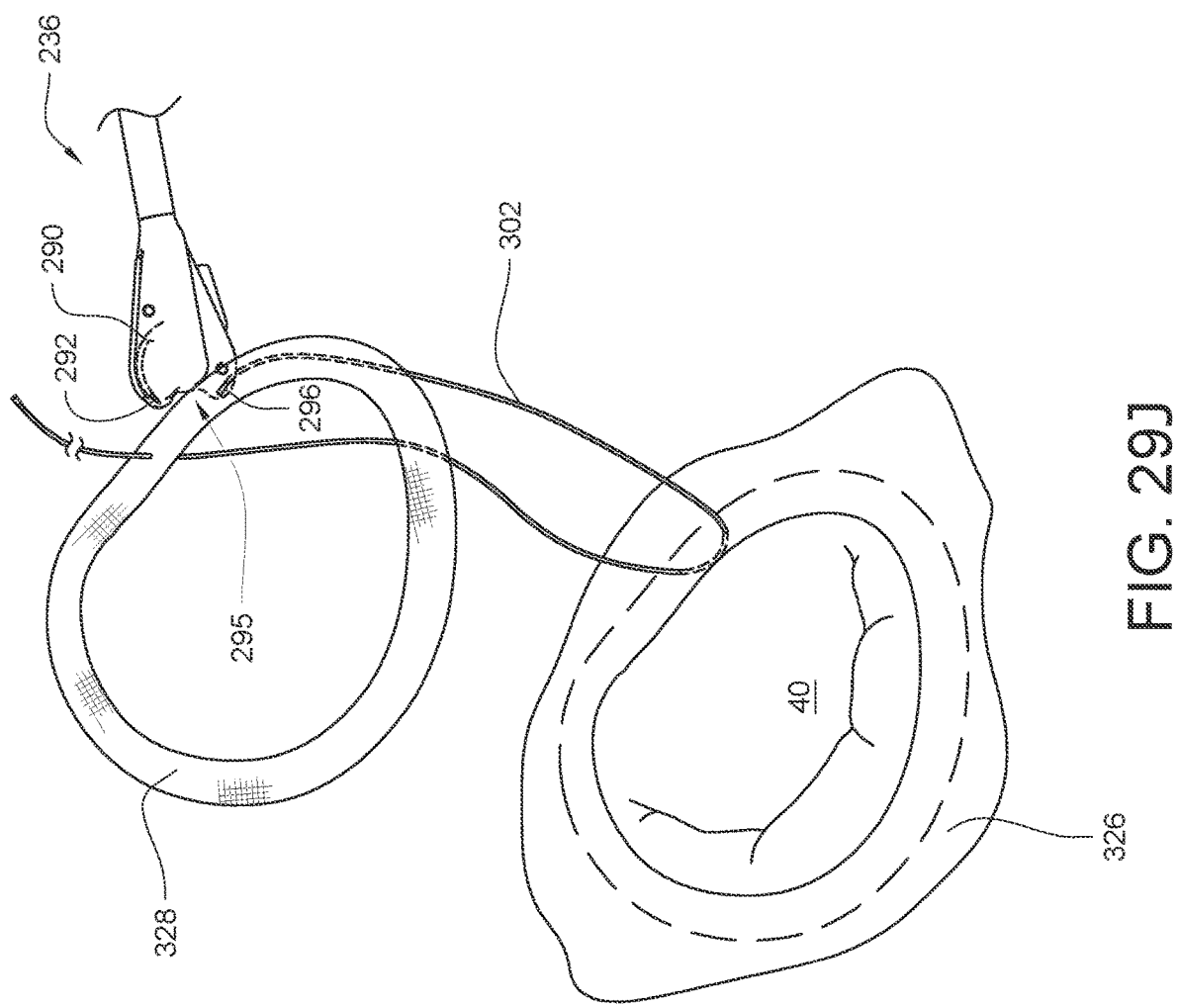
Figure 29K:
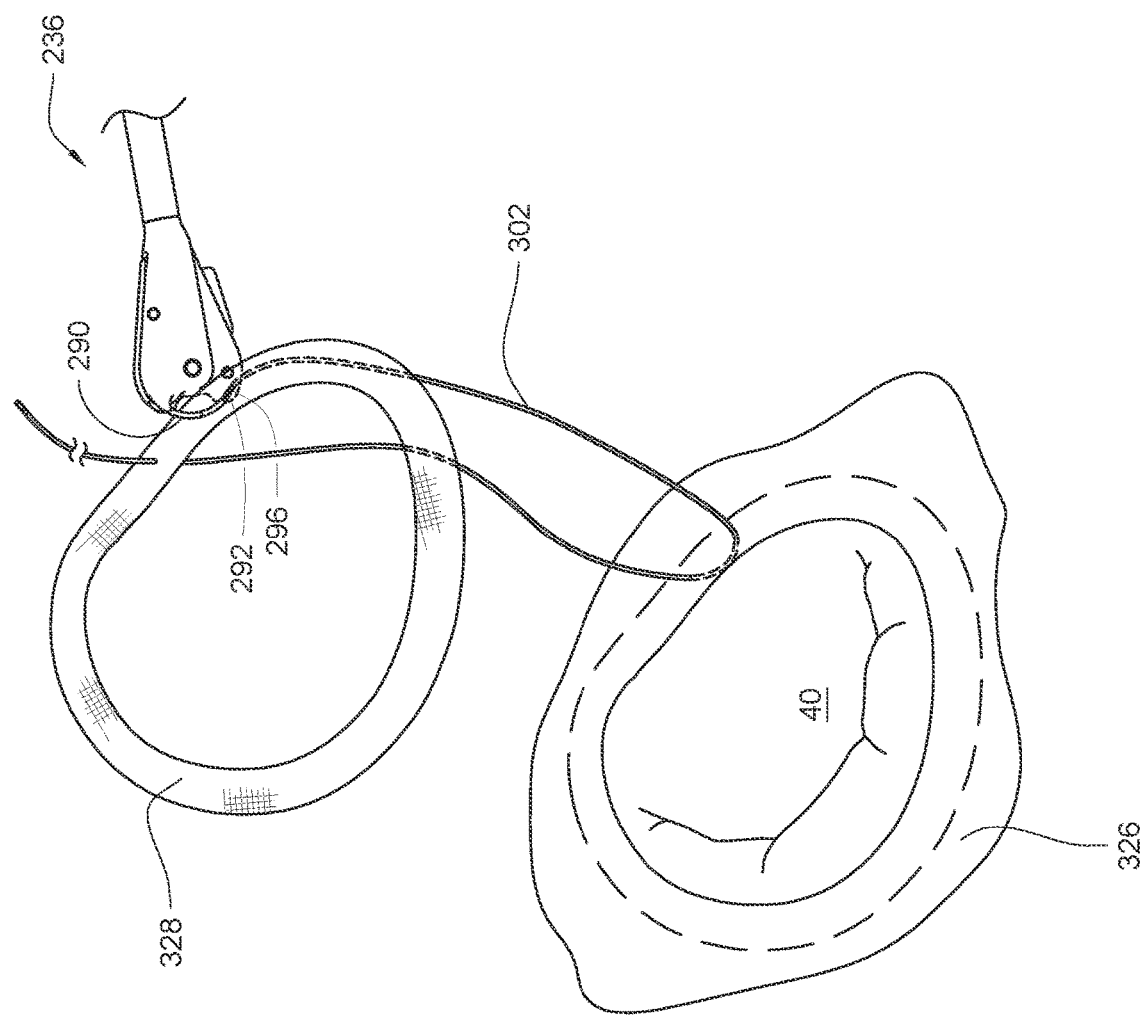
Figure 29L:
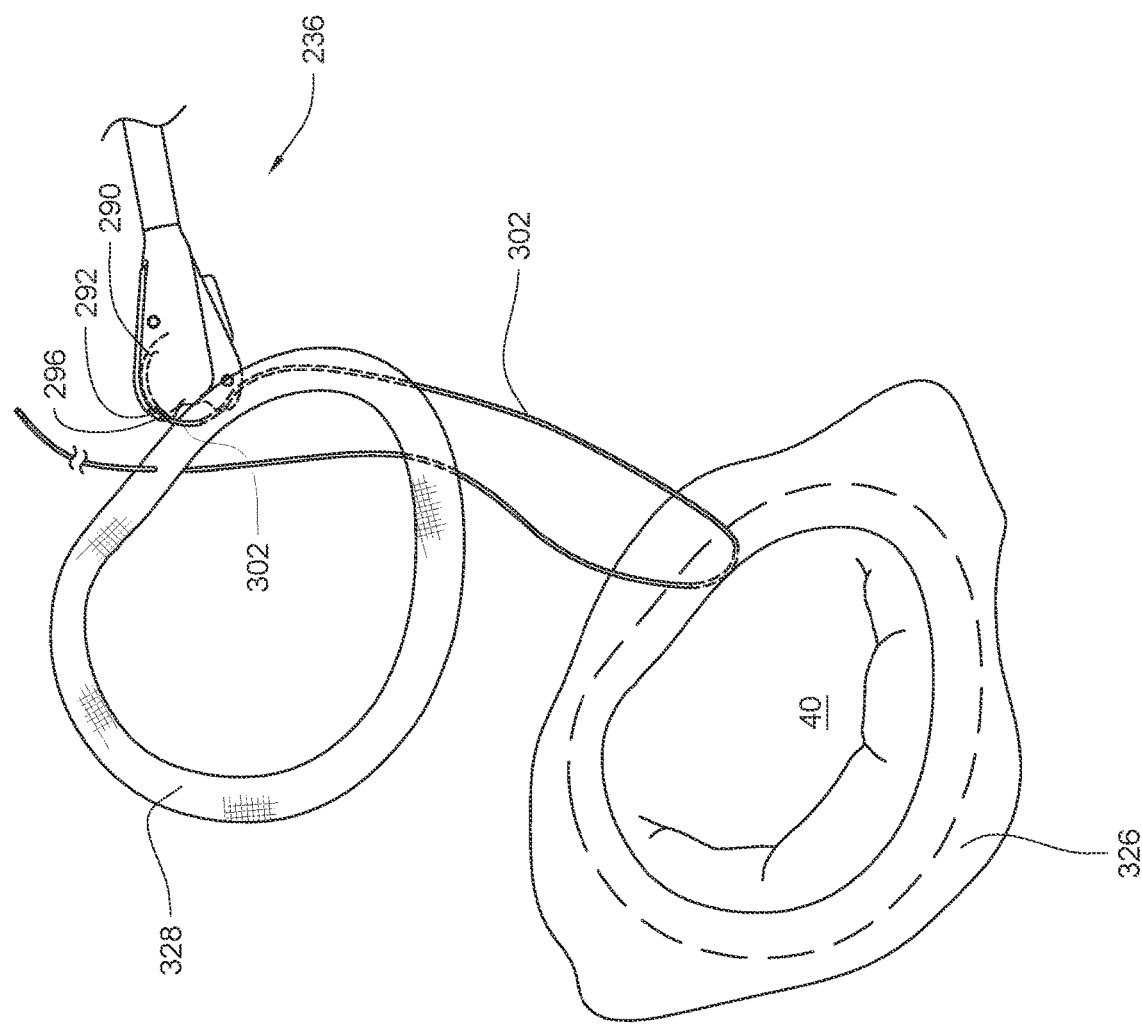
Figure 29M:
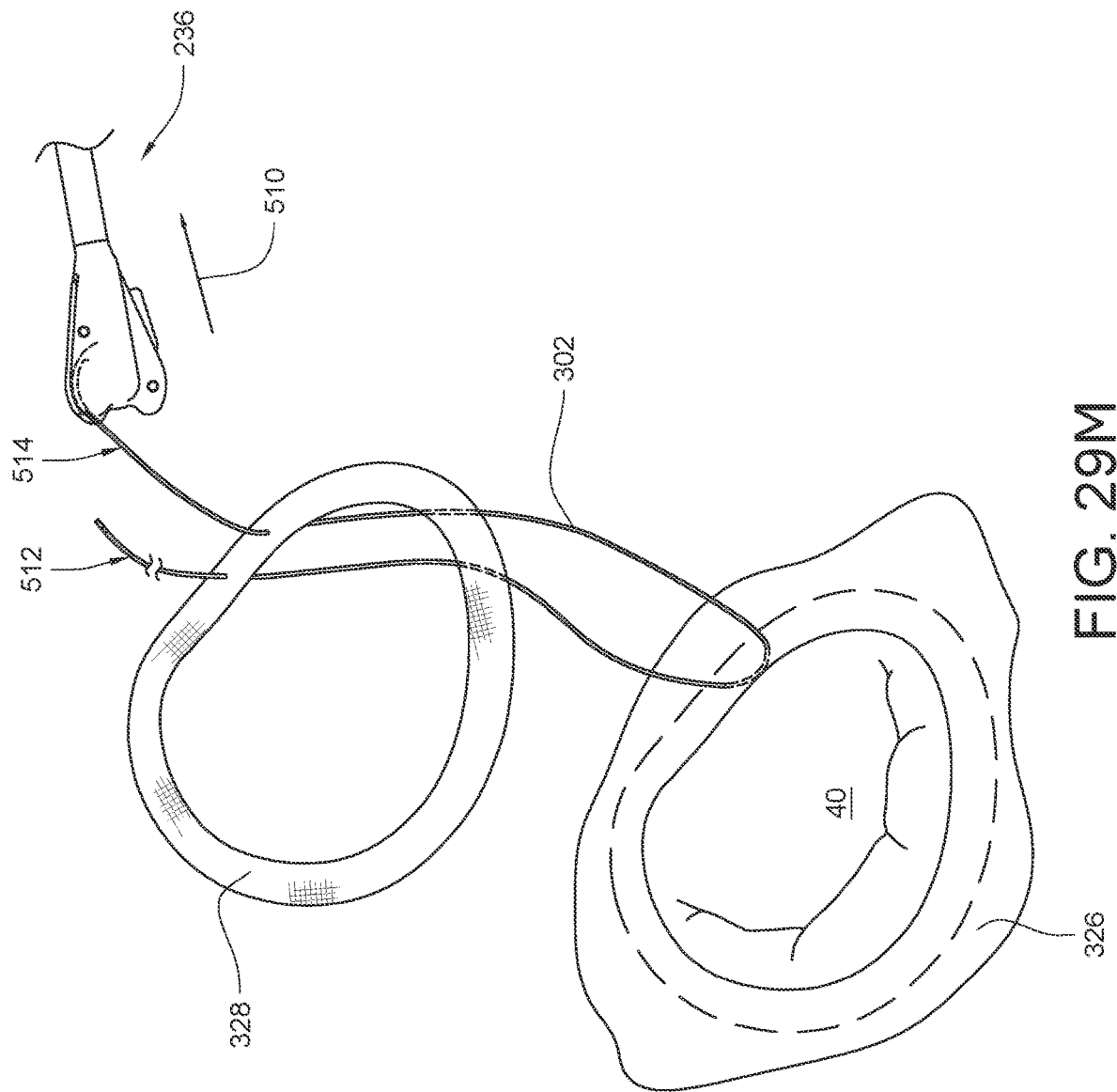
Figure 29N:
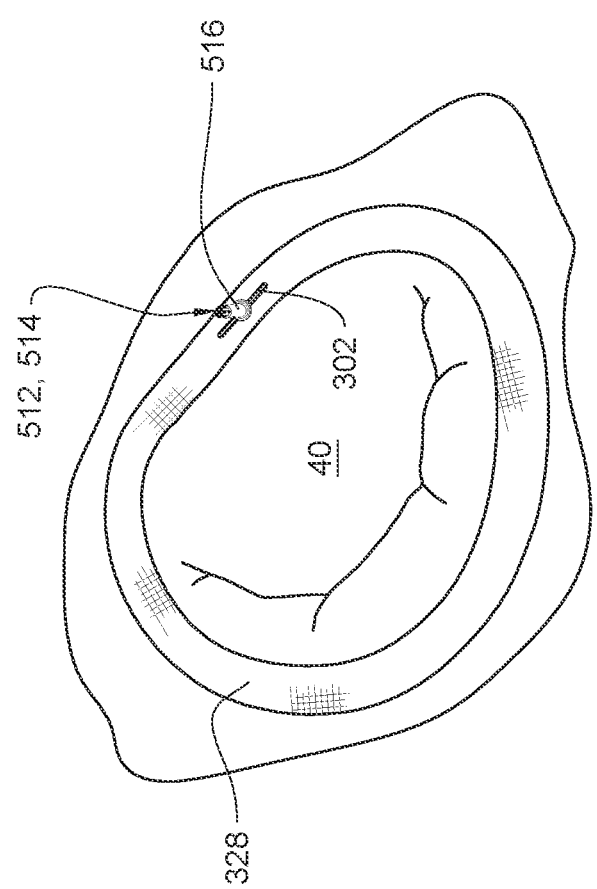

FIGS. 29A-29N illustrate another method of suturing an annuloplasty ring to underlying tissue using the surgical suturing device of FIG. 14. FIG. 29A schematically illustrates a surgical situation. Minimally invasive access has been gained to a chamber of the heart. Annular tissue 326 surrounding a mitral valve 40 has become enlarged and, as a result, the valve's leaflets are no longer able to maintain proper mitral valve closure. An annuloplasty ring, of a desired annulus size, may be installed over the annular tissue such that the annular tissue is snugged inward towards the prosthetic to reestablish a preferred, smaller mitral annulus. The annuloplasty ring 328 is initially positioned away from the annular tissue, for example, outside of the patient's body. The suturing device 236 is ready to be used. For convenience, the handle, actuator, and entire shaft are not shown in these views. As before, the device 236 has a bite area 295 defined at least in part by the head 254 at the end of the shaft 242. The ferrule 296, coupled to the end of suture 302 is held in the ferrule holder on one side of the bite area 295 in the device head 254. The curved arm 290 and its ferrule engaging tip 292 are in a retracted position on the other side of the bite area 295.

As shown in FIG. 29B, the tissue bite area 295 is placed against the annuloplasty ring 328 from the side, such that the curved arm 290, if it were to be engaged, would only pass once through the annuloplasty ring 328 on its way to the ferrule 296. As illustrated in FIG. 29C, the needle is actuated so the curved arm 290 and its ferrule engaging tip 292 pass up through the annuloplasty ring 328 and into contact with ferrule 296. As shown in FIG. 29D, the needle is de-actuated so that the curved arm 290 and its ferrule engaging tip 292 (along with the attached ferrule) are pulled back down through the annuloplasty ring 328 and into a retracted position again. As illustrated in FIG. 29E, the suturing device 236 may be pulled away 506 from the annuloplasty ring 328, thereby drawing more of the suture 302 down from the stitch in the annuloplasty ring 328. The ferrule 296 may be returned to the ferrule holder (not visible in this view) using the ferrule removal feature 259, as described above with regard to FIGS. 18D-18F, and the device 236 will be ready to place a second stitch.

As shown in FIG. 29F, the tissue bite area 295 is placed onto the annular tissue 326 at a position which is intended to correspond to the first stitch that was already placed in the annuloplasty ring. As shown in FIG. 29G, the needle is actuated so that the curved arm 290 and its ferrule engaging tip 292 pass down through annular tissue 326 and back up into contact with the ferrule 296. As shown in FIG. 29H, the needle is de-actuated so that the curved arm 290 and its ferrule engaging tip 292 (along with the attached ferrules 296) are pulled back through the annular tissue 236 and into a retracted position again. Since the end of suture 302 is coupled to the ferrule 296, part of the suture 302 is also pulled through the annular tissue 236. As illustrated in FIG. 29I, the suturing device 236 may be pulled away 508 from the annular tissue 326, thereby drawing more of the suture 302 up from the stitch in the annular tissue 326. The ferrule 296 may be returned to the ferrule holder (not visible in this view) using the ferrule removal feature 259 as described above with regard to FIGS. 18D-18F, and the device 236 will be ready to place a third stitch.

As shown in FIG. 29J, the tissue bite area 295 is once again placed against the annuloplasty ring 328 from the side, such that the curved arm 290, if it were to be engaged, would only pass once through the annuloplasty ring 328 on its way to the ferrule 296. As illustrated in FIG. 29K, the needle is actuated so the curved arm 290 and its ferrule engaging tip 292 pass down through the annuloplasty ring 328 and into contact with ferrule 296. As shown in FIG. 29L, the needle is de-actuated so that the curved arm 290 and its ferrule engaging tip 292 (along with the attached ferrule) are pulled back up through the annuloplasty ring 328 and into a retracted position again. As illustrated in FIG. 29M, the suturing device 236 may be pulled away 510 from the annuloplasty ring 328, thereby drawing more of the suture 302 up from this second stitch in the annuloplasty ring 328. The ferrule 296 may be removed from the suture 302, leaving first and second ends 512, 514 of the suture 302 protruding up from the annuloplasty ring 328. If desired, the above method may be repeated at one or more additional locations with one or more additional sutures. For simplicity, however, just a single suture 302 with its two suture ends 512, 514 are discussed in this example. As illustrated in FIG. 29N, the loose suture ends 512, 514 may be secured with a mechanical fastener 516 to help hold the annuloplasty ring 328 in place. The suture ends 512, 514 are shown trimmed in FIG. 29N.

Figure 30:
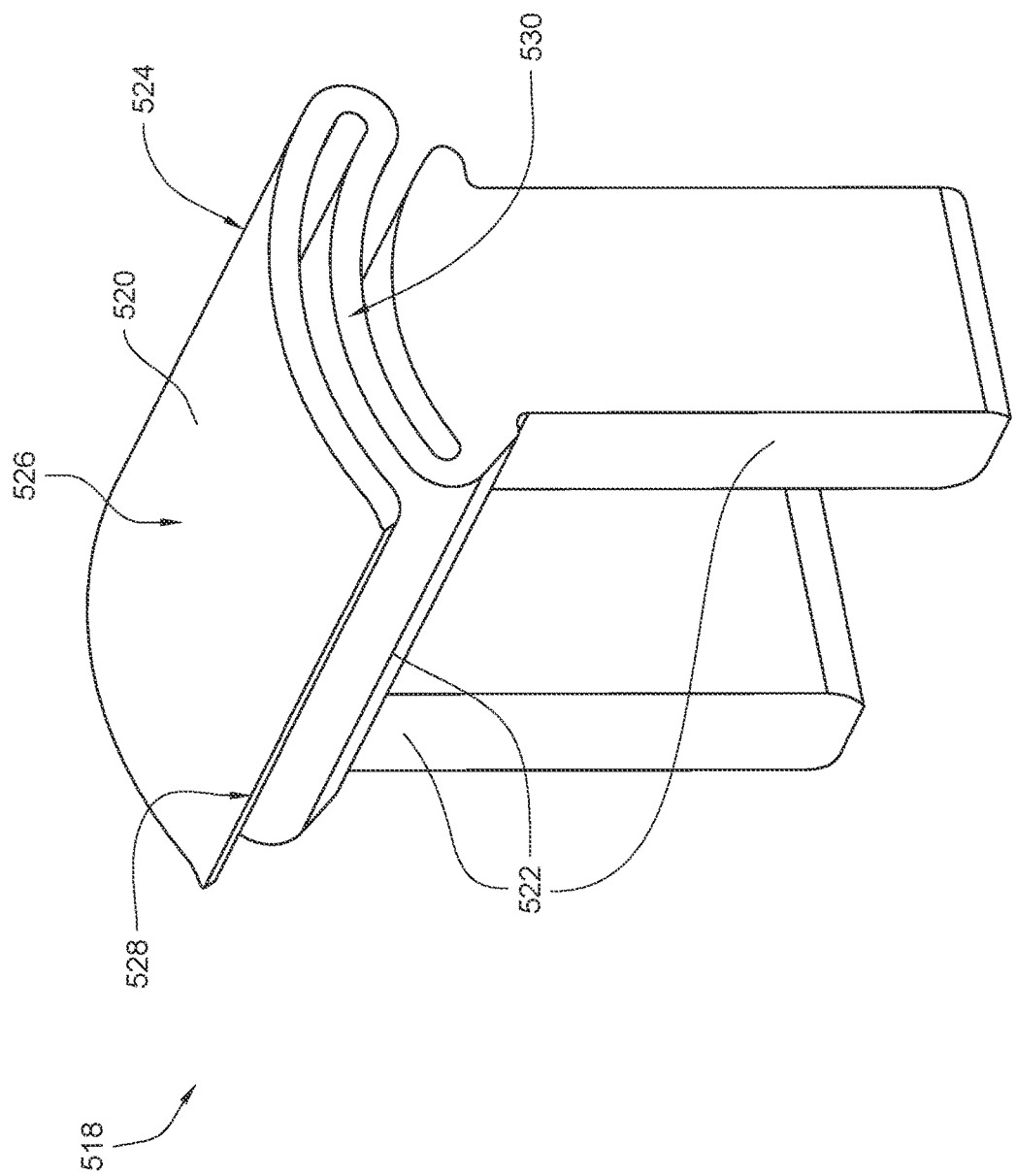
FIG. 30 is a perspective view of one embodiment of a re-arming tool for a surgical suturing device.

Some of the embodiments discussed above, such as the surgical suturing device of FIGS. 14-15, have a ferrule release feature 259 which is positioned to enable a ferrule to be returned to a ferrule holder after it had previously been captured by a ferrule engaging tip of a needle. This resetting (or re-arming) of the ferrule enables a running stitch to be performed with a single suture using the surgical suturing device. However, for other embodiments of surgical suturing devices, which do not have an integral ferrule release feature for re-arming the device, it may be desirable to have an apparatus and method for being able to re-arm the surgical suturing device. FIG. 30 is a perspective view of one embodiment of a re-arming tool 518 for a surgical suturing device. The re-arming tool 518 has a needle ramp 520 and a positioning frame 522 coupled to the needle ramp 520. As will be demonstrated in an example below, in this embodiment, the positioning frame 522 is configured to engage a tissue bite area of a surgical suturing device. In other embodiments, the positioning frame may be configured to engage any part of the surgical suturing device for the purpose of positioning the needle ramp 520 relative to a travel path of one or more ferrule engaging tips of one or more needles.

The needle ramp 520 has a leading edge 524, a needle facing surface 526, and a trailing edge 528. In this embodiment, the leading edge 524 is rounded, but in other embodiments, the leading edge could have a sharper or differently shaped edge. In this embodiment, the needle ramp 520 has an arcuate surface which is shaped to correspond with the arcuate path of one or more curved arms of a needle, as will be discussed in more detail below. The needle facing surface 526 is on a convex side of the arcuate needle ramp 520 in this embodiment.

The trailing edge 528 is biased away from the needle facing surface 520 in this embodiment by a spring element 530 which couples the positioning frame 522 to the needle ramp 520. Suitable examples of a spring element could include, but are not limited to, a compression spring, a tension spring, a torsion spring, a constant force spring, a variable force spring, a leaf spring, a helical spring, and a machined spring. Although the trailing edge 528 is integral with the needle ramp 520 in this embodiment, in other embodiments, the trailing edge could be separately movable relative to the needle ramp 520. (For example, if the needle ramp was coupled to the positioning frame without a spring element, while a separate trailing edge was biased by a spring element that was also coupled to the positioning frame).

Figure 31A:
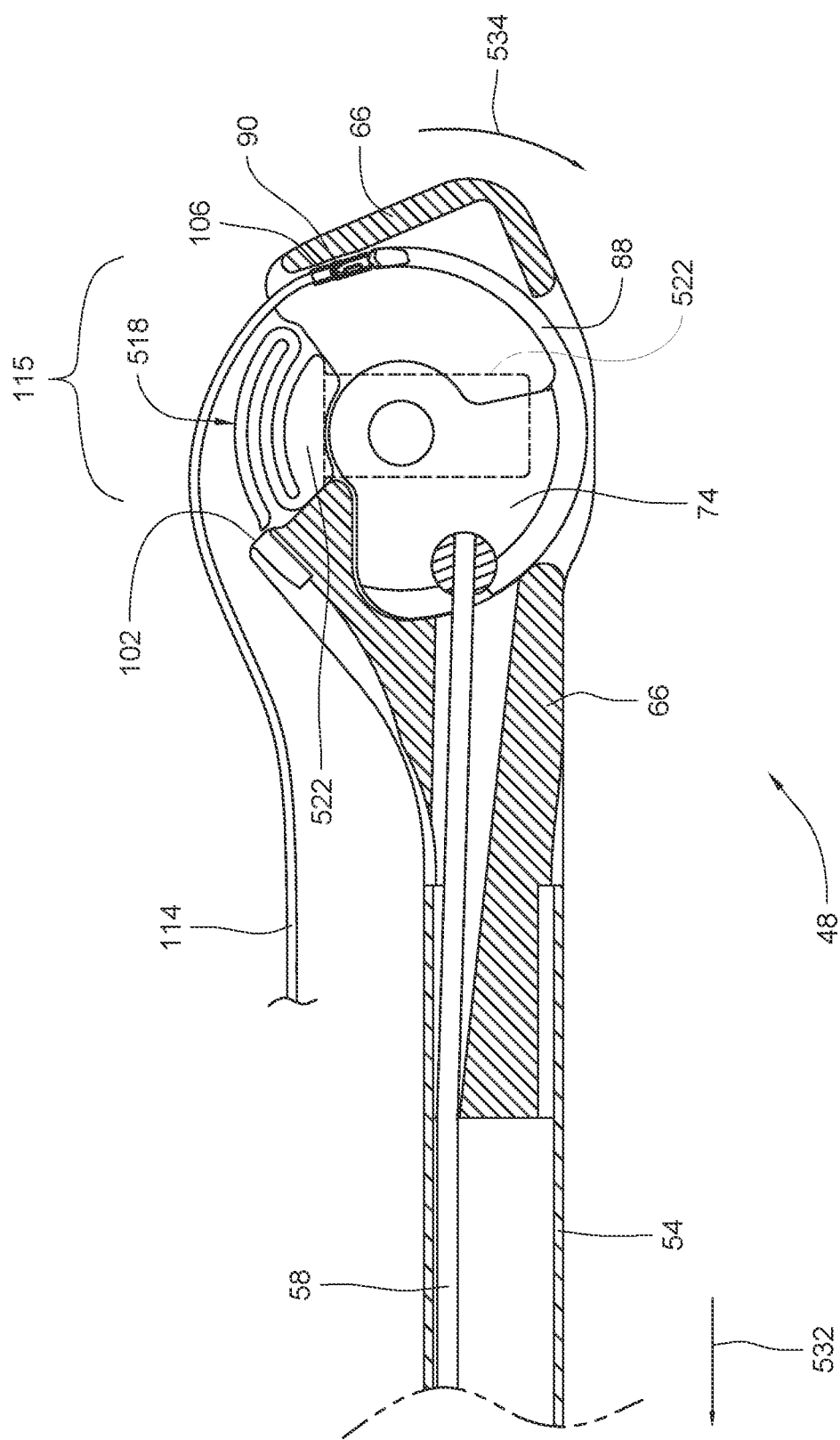
FIGS. 31A-31C are partial cross-sectional side views of a surgical suturing device being re-armed with the re-arming tool of FIG. 30.
Figure 31B:
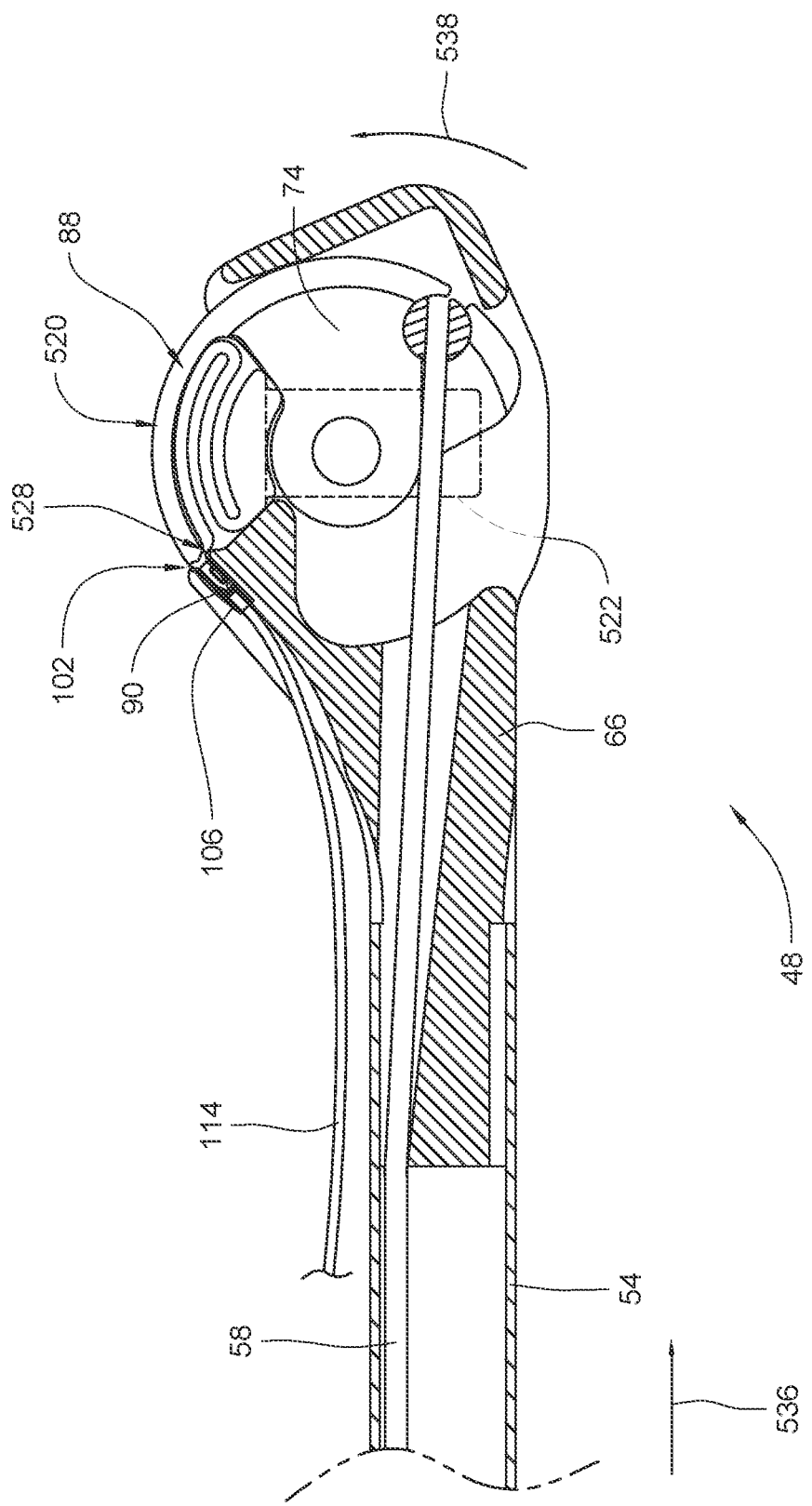
Figure 31C:
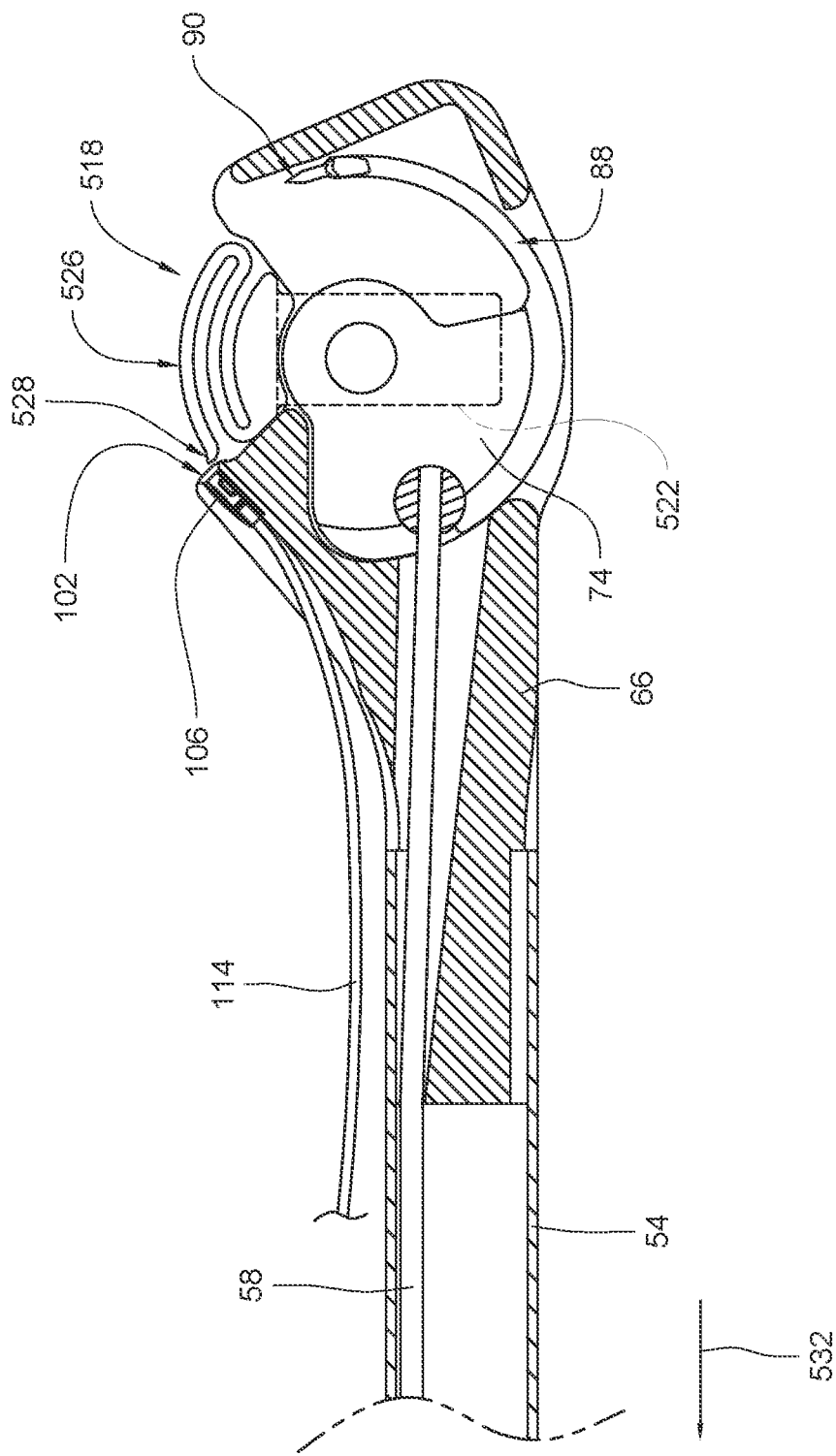

FIGS. 31A-31C are partial cross-sectional side views of a surgical suturing device being re-armed with the re-arming tool of FIG. 30. The suturing device in FIGS. 31A-31C is the same as the suturing device 48 from FIG. 2, discussed previously. The situation illustrated in FIG. 31A is similar to the situation of FIG. 6C, also discussed previously. In FIG. 31A, the actuator rod 58 has been moved in a proximal direction 532, which caused the needle 74 to rotate in an arcuate direction 534 about its needle pivot axis. Although the needle 74 has more than one curved arm and corresponding ferrule engaging tip in this embodiment, the side view only allows us to see what is happening with a single curved arm 88, its ferrule engaging tip 90, and its corresponding ferrule 106 attached to the suture 114. It should be understood, however, that the described re-arming process can be occurring similarly for multiple curved arms at the same time. The ferrule engaging tip 90 of the curved arm 88 (and the ferrule 106 which is coupled to them) are in a retracted position, which might occur, for example, after having already used the device 48 to create a first stitch in tissue or some other object.

As can also be seen in FIG. 31A, the re-arming tool 518 of FIG. 30 has been positioned within the bite area 115 of the device 48. In this embodiment, the positioning frame 522 engages the outside of the device head 66 and also passes through the tissue bite area 115. Since the view of FIG. 31A is a partially exposed view, the back leg of the positioning frame 522 is visible as a broken line hidden object; the nearest leg is not visible in this view.

As illustrated in FIG. 31B, the re-arming tool 518 is positioned so that the ferrule 106, while held by the ferrule engaging tip 90 of the curved arm 88, will ride in proximity to and/or across the needle ramp 520 when the actuator rod 58 is moved in a distal direction 536, thereby causing the needle 74 to rotate in another arcuate direction 538 about its needle pivot axis. While rotating in arcuate direction 538, the ferrule engaging tip 90 of the curved arm 88 passes from its retracted position (shown in FIG. 31A), past the needle ramp 520, over the trailing edge 528, and returns the ferrule 106 to the ferrule holder 102. At this point, however, the ferrule 106 is still coupled to the ferrule engaging tip 90 of the curved arm 88.

Since the trailing edge 528 is biased away from the needle facing surface (towards the curved arm 88 of the needle 74 in this embodiment), the trailing edge 528 of the re-arming tool 518 contacts the curved arm 88 just before it meets the ferrule 106 at the ferrule engaging tip 90. In this position, illustrated in FIG. 31B, the trailing edge 528 will prevent the ferrule 106 from returning with the ferrule engaging tip 90 if the needle 74 is rotated back to its retracted position. In FIG. 31C, the needle 74 has been rotated back to its retracted position with another proximal movement 532 of the actuator rod 58. The trailing edge 528 of the re-arming tool 518 has kept the ferrule 106 in the ferrule holder 102, while the ferrule engaging tip 90 of the curved arm 88 is correspondingly ferrule-free. At this stage, the re-arming tool 518 may be removed and the device is ready to place another stitch in a desired tissue or object location. Re-arming tool 518 and its equivalents are useful for enabling multiple stitches to be placed with the same suture without having to handle the ferrule coupled to the suture in-between the multiple stitches.

Figure 32A:
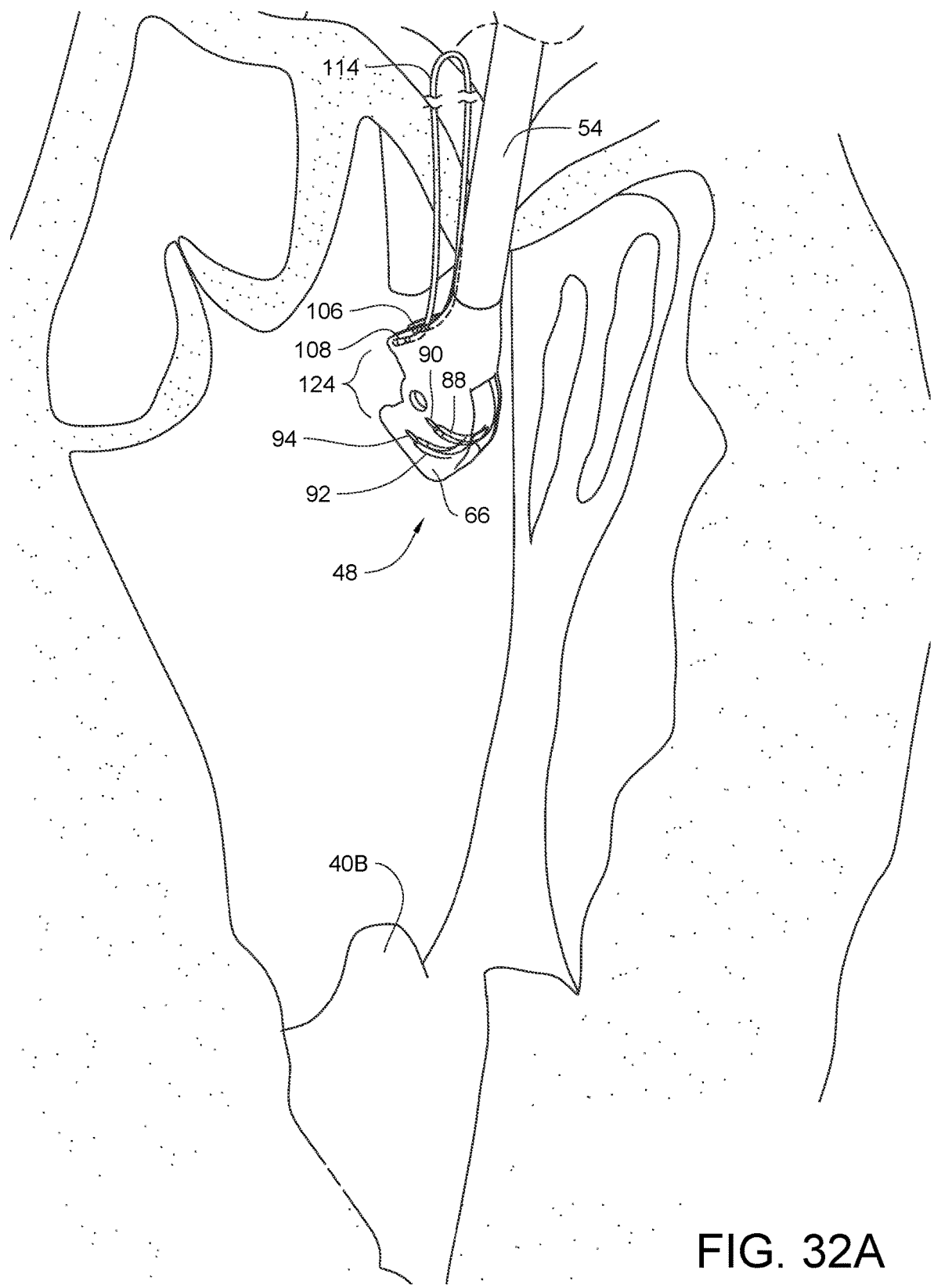
FIGS. 32A-32J illustrate another method of replacing a chordae tendinae of the heart using the surgical suturing device of FIG. 2.

FIGS. 32A-32J illustrate another method of replacing a chordae tendinae of the heart using the surgical suturing device of FIG. 2. FIG. 32A illustrates a surgical situation. Minimally invasive access has been gained to the left ventricle of the heart. A pathologic chord has been removed from the illustrated papillary muscle 40B, and the suturing device 48 is ready to be used. For convenience, the handle, actuator, and entire shaft are not shown in these views. As before, the device 48 has a tissue bite area 124 defined at least in part by the head 66 at the end of the shaft 54. First and second ferrules 106, 108, coupled to the ends of suture 114 are held in ferrule holders (not visible in this view) on the proximal side of the tissue bite area 124 in the device head 66. The first and second curved arms 88, 92 and their respective first and second ferrule engaging tips 90, 94 are in a retracted position on the distal side of the tissue bite area 124.

Figure 32B:
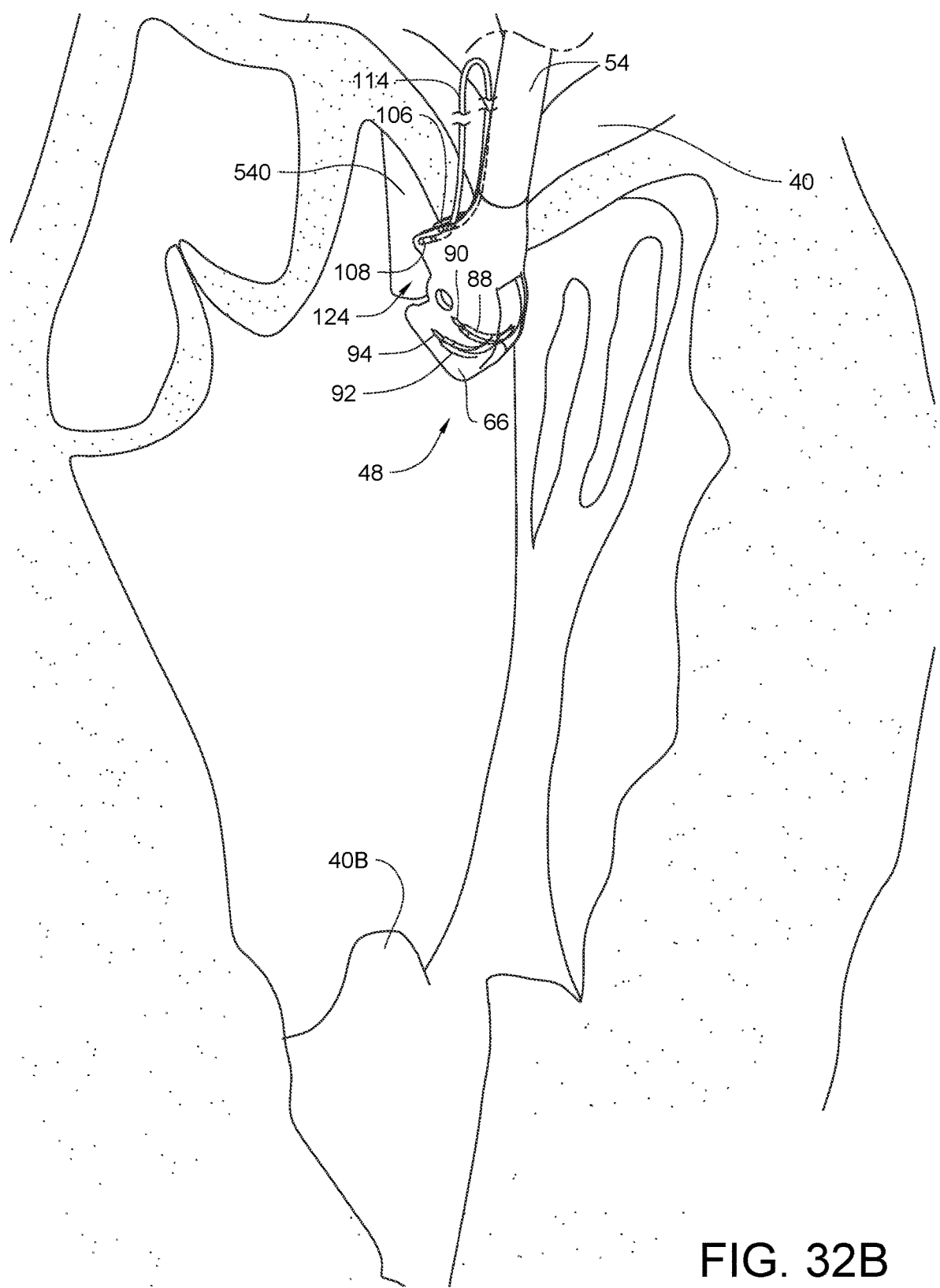
Figure 32C:
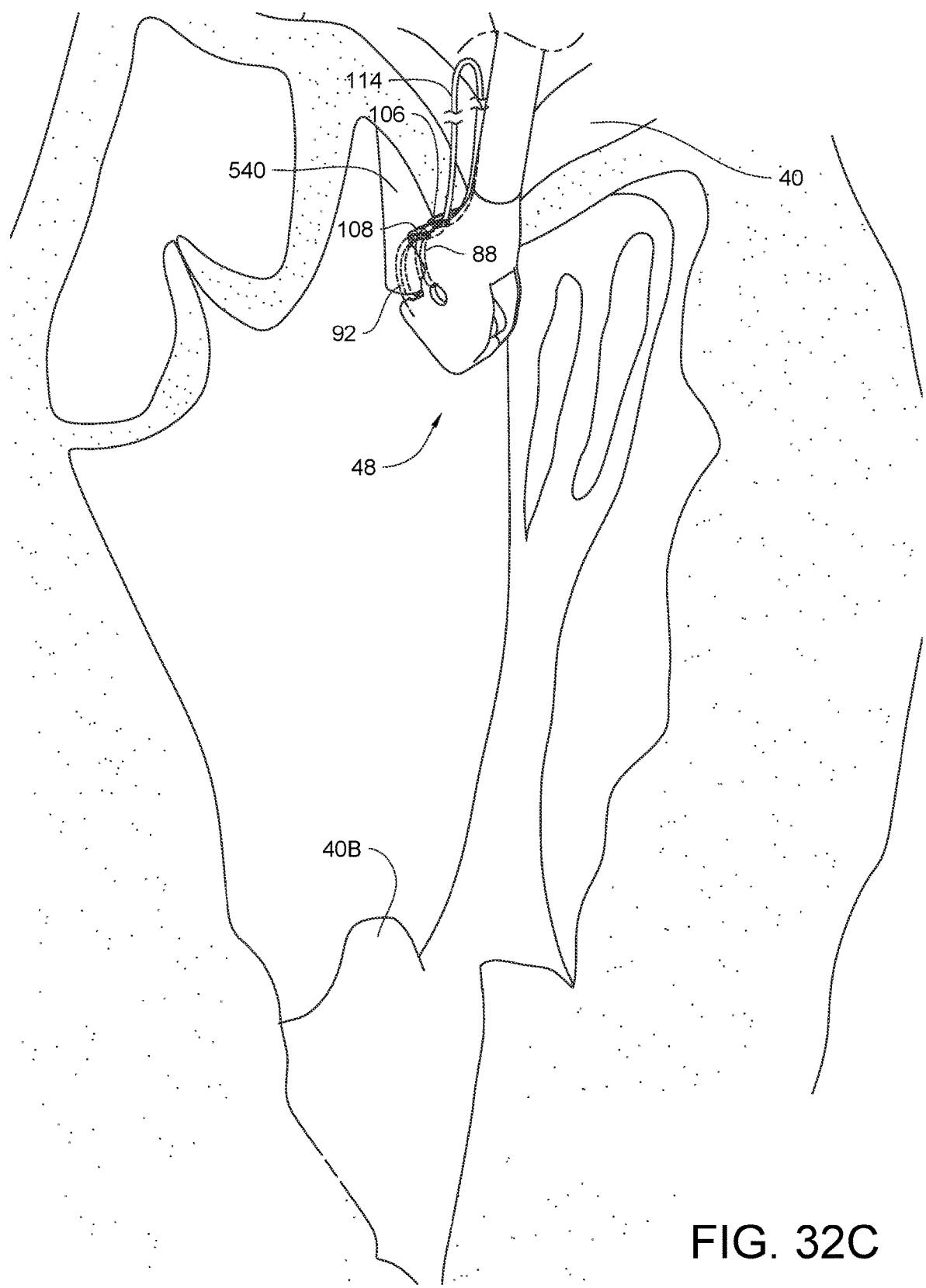
Figure 32D:
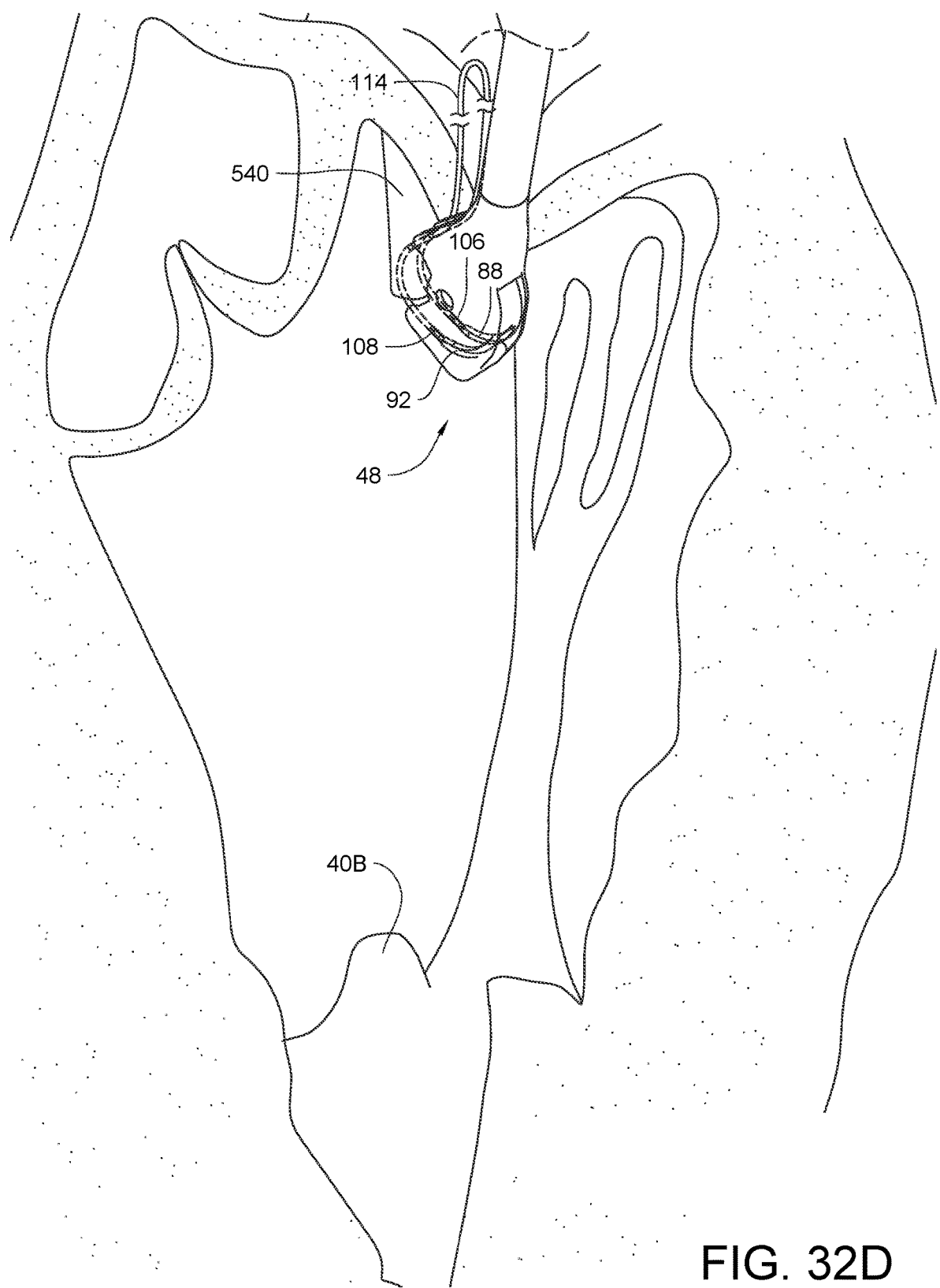
Figure 32E:
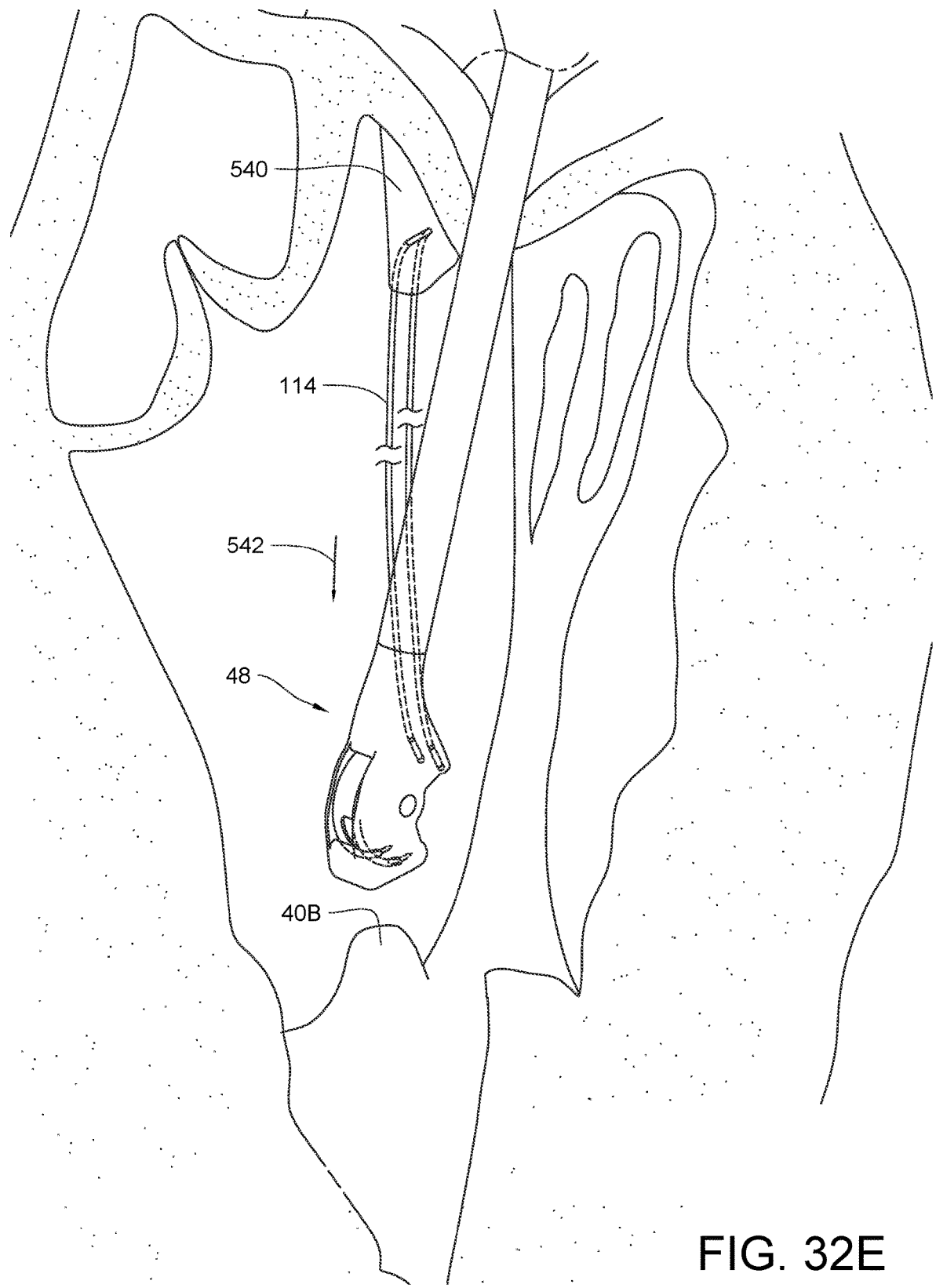

As shown in FIG. 32B, the tissue bite area 124 is placed over a leaflet 540 of the mitral valve 40. As shown in FIG. 32C, the needle is actuated so that the first and second curved arms 88, 92, and their respective ferrule engaging tips, pass through the leaflet 540 in the tissue bite area and engage the corresponding first and second ferrules 106, 108. As shown in FIG. 32D, the needle is actuated so that the first and second curved arms 88, 92 and their respective ferrule engaging tips (as well as the respective ferrules 106, 108 held by those ferrule engaging tips) are pulled back through the leaflet 540 in the tissue bite area and into a retracted position again. Since the ends of suture 114 are coupled to the ferrules 106, 108, the suture 114 is also pulled through the leaflet 540. As illustrated in FIG. 32E, the suturing device 48 may be pulled away 542 from the leaflet 540 in order to take up the slack in the suture 114.

Figure 32F:
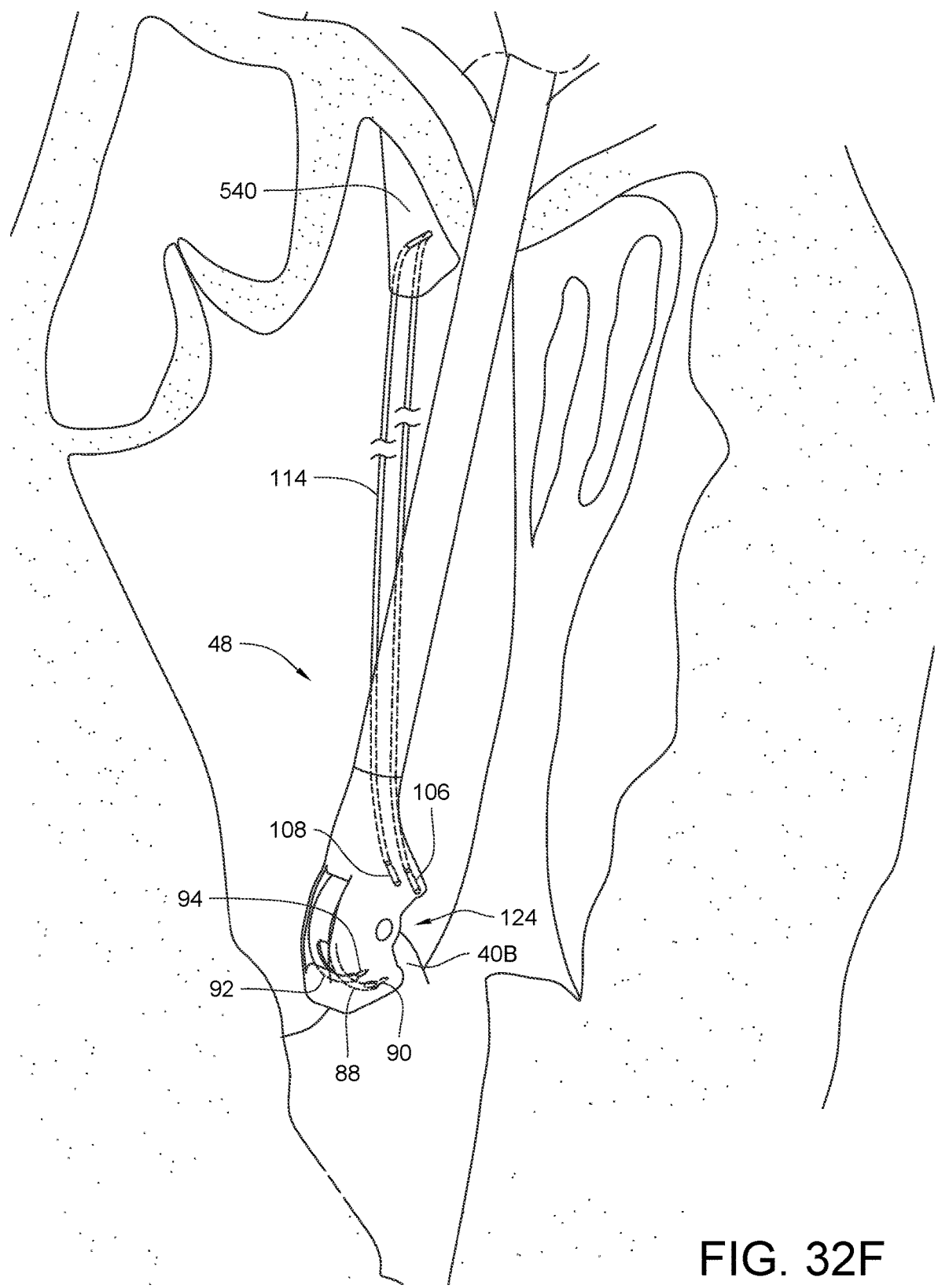
Figure 32G:
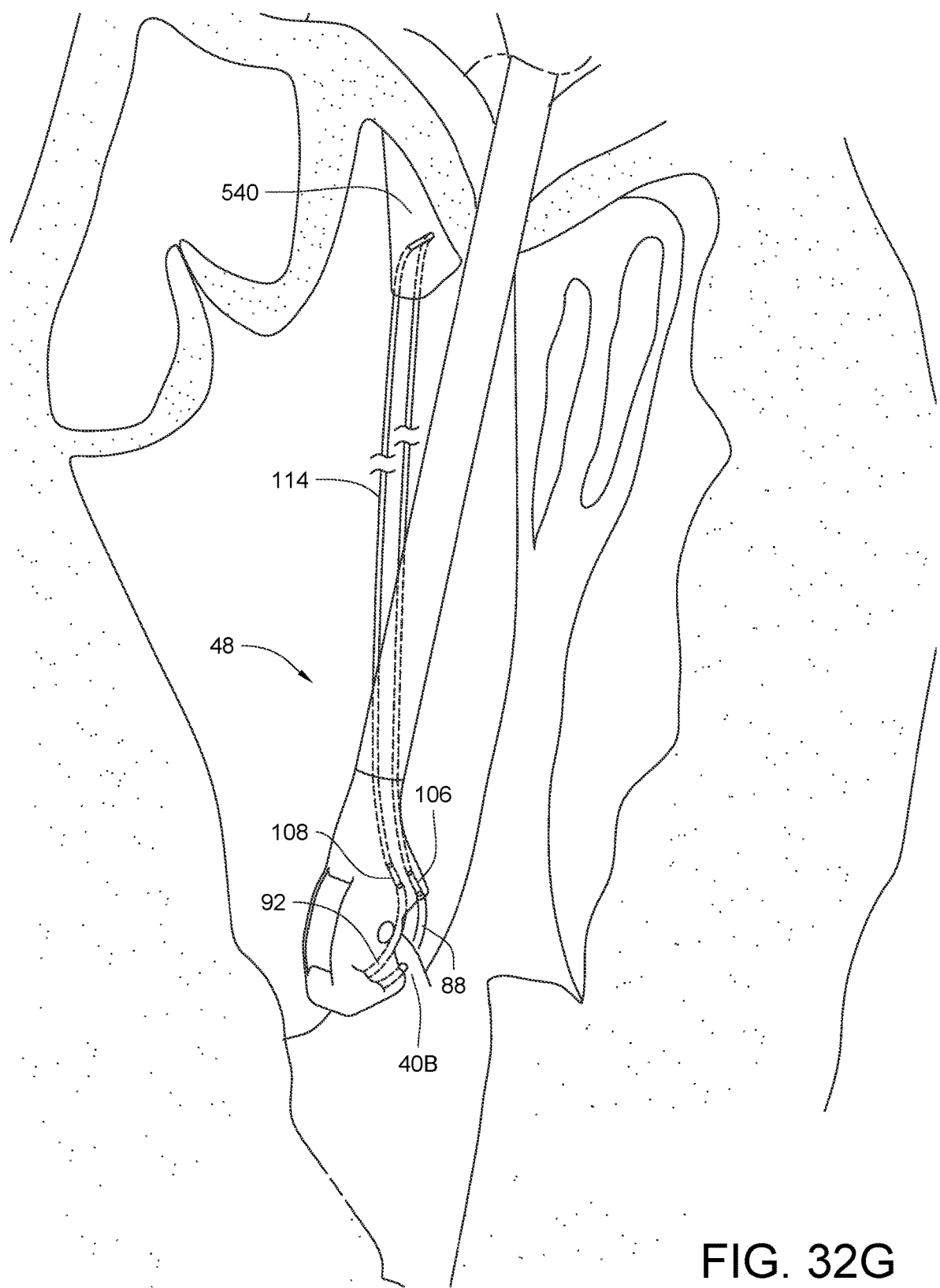
Figure 32H:
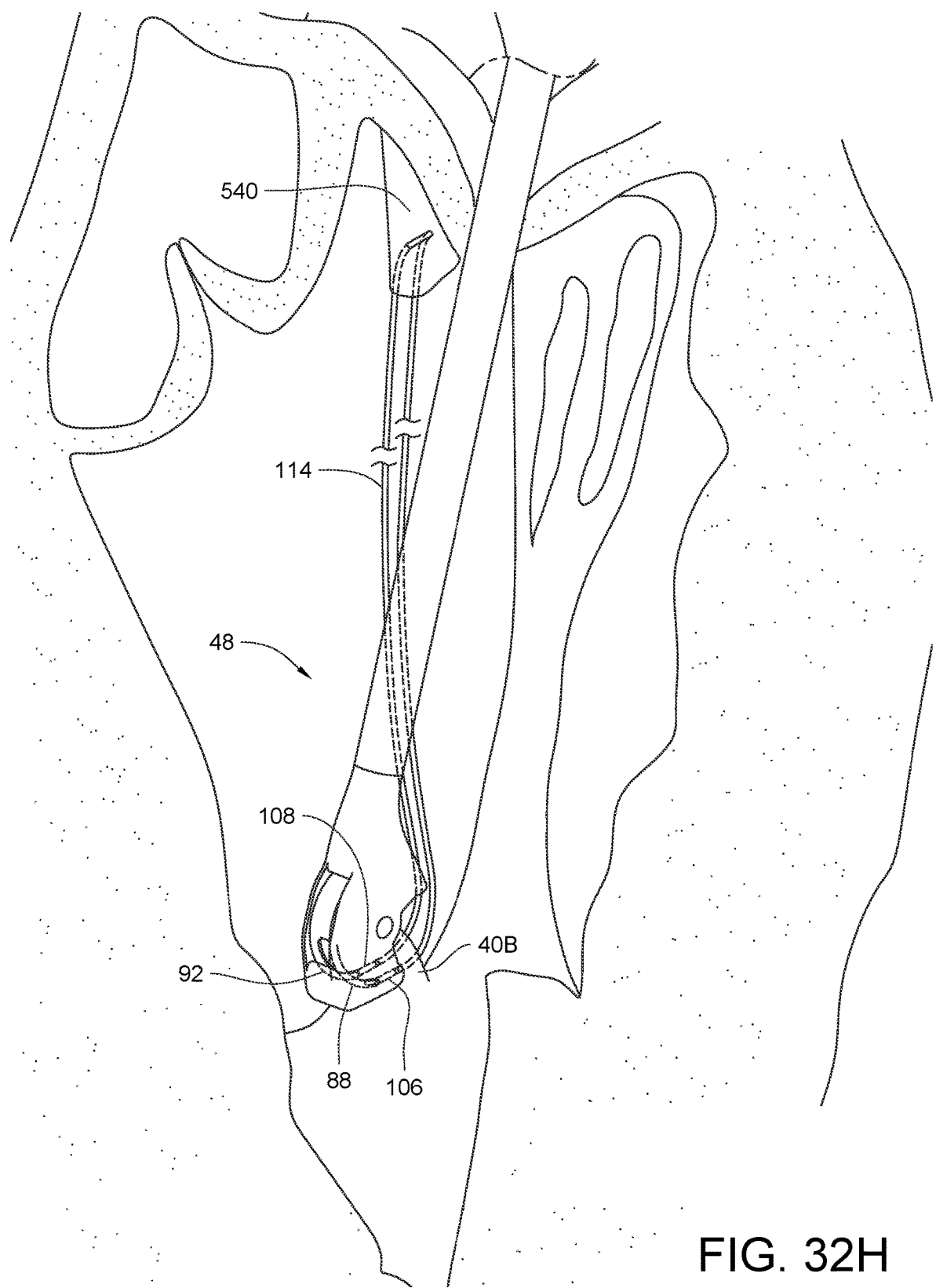
Figure 32I:
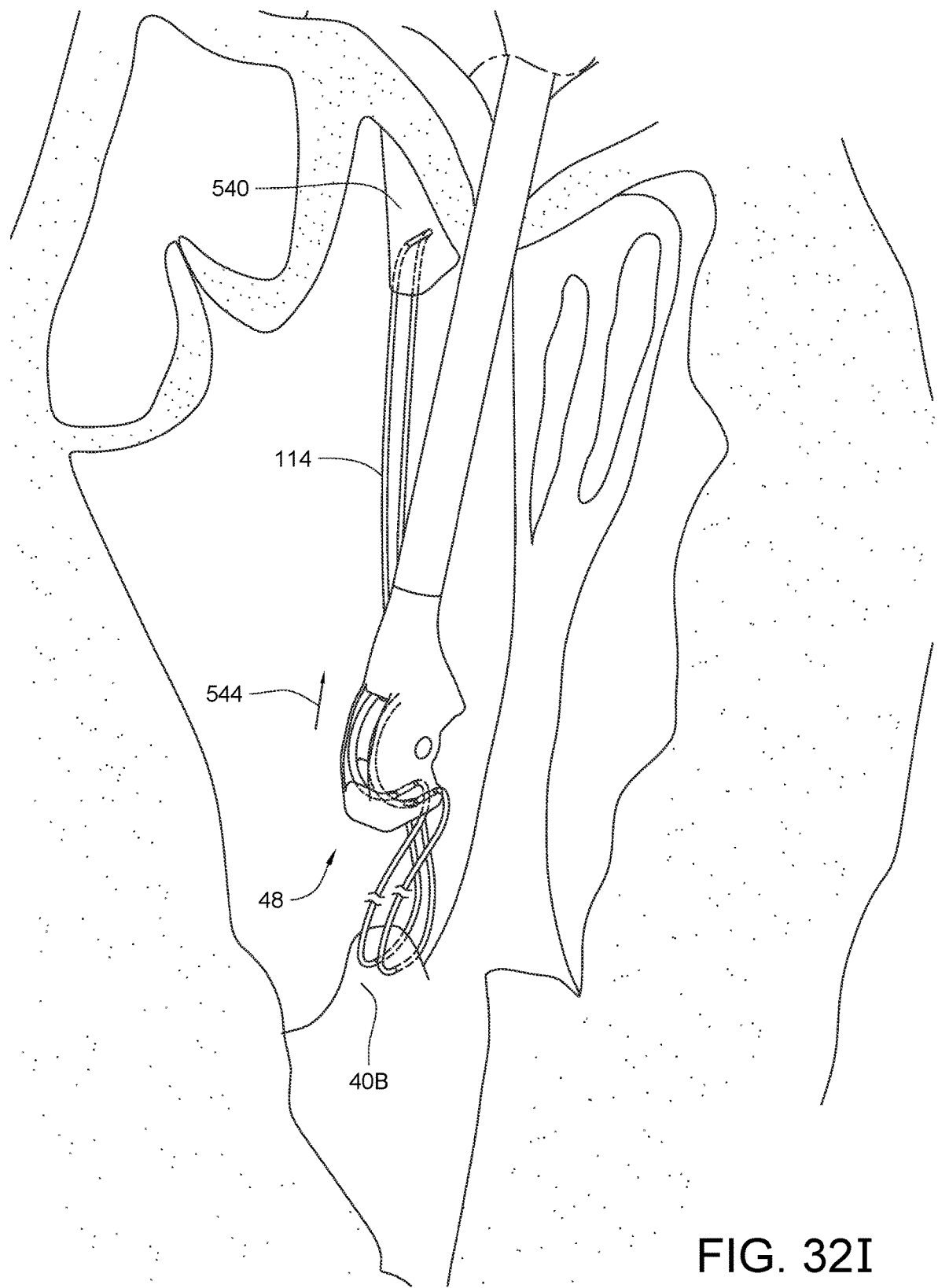
Figure 32J:
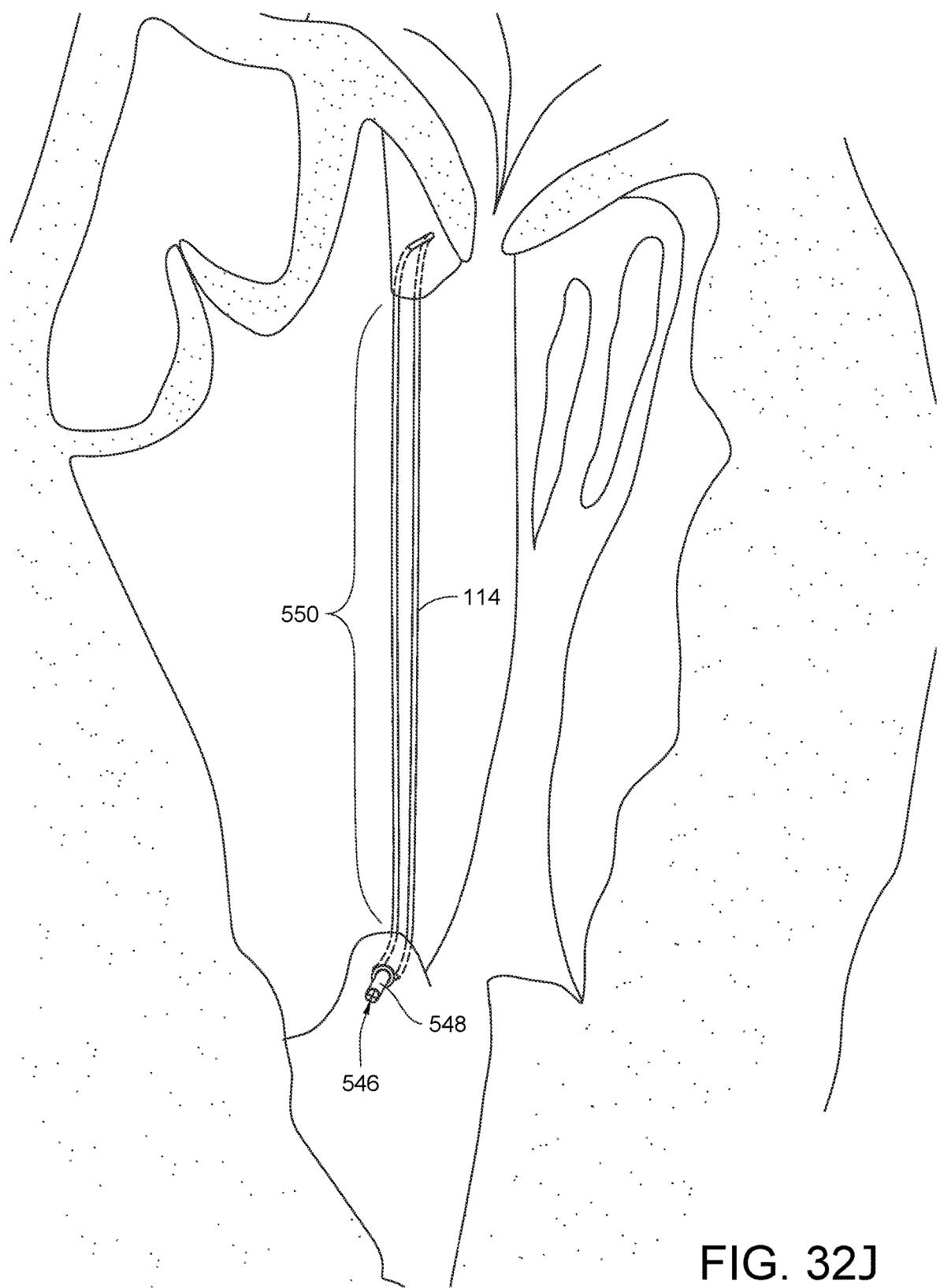

Next, as illustrated in FIG. 32F, the tissue bite area 124 is placed over the papillary muscle 40B. As shown in FIG. 32G, the needle is actuated so that the first and second curved arms 88, 92, and their respective ferrule engaging tips, pass through the papillary muscle 40B in the tissue bite area and engage the corresponding first and second ferrules 106, 108. As shown in FIG. 32H, the needle is actuated so that the first and second curved arms 88, 92 and their respective ferrule engaging tips (as well as the respective ferrules 106, 108 held by those ferrule engaging tips) are pulled back through the tissue 40B in the tissue bite area and into a retracted position again. Since the ends of suture 114 are coupled to the ferrules 106, 108, the suture 114 is also pulled through the papillary muscle 40B. As illustrated in FIG. 32I, the suturing device 48 may be pulled away 544 from the papillary muscle 40B in order to take up the slack in the suture 114. The ferrules 106, 108 may be removed from the suture 114, and the suture ends 546 may be secured with a mechanical fastener 548 once the desired replacement chord length 550 has been selected by adjusting the suture 114.

Figure 33A:
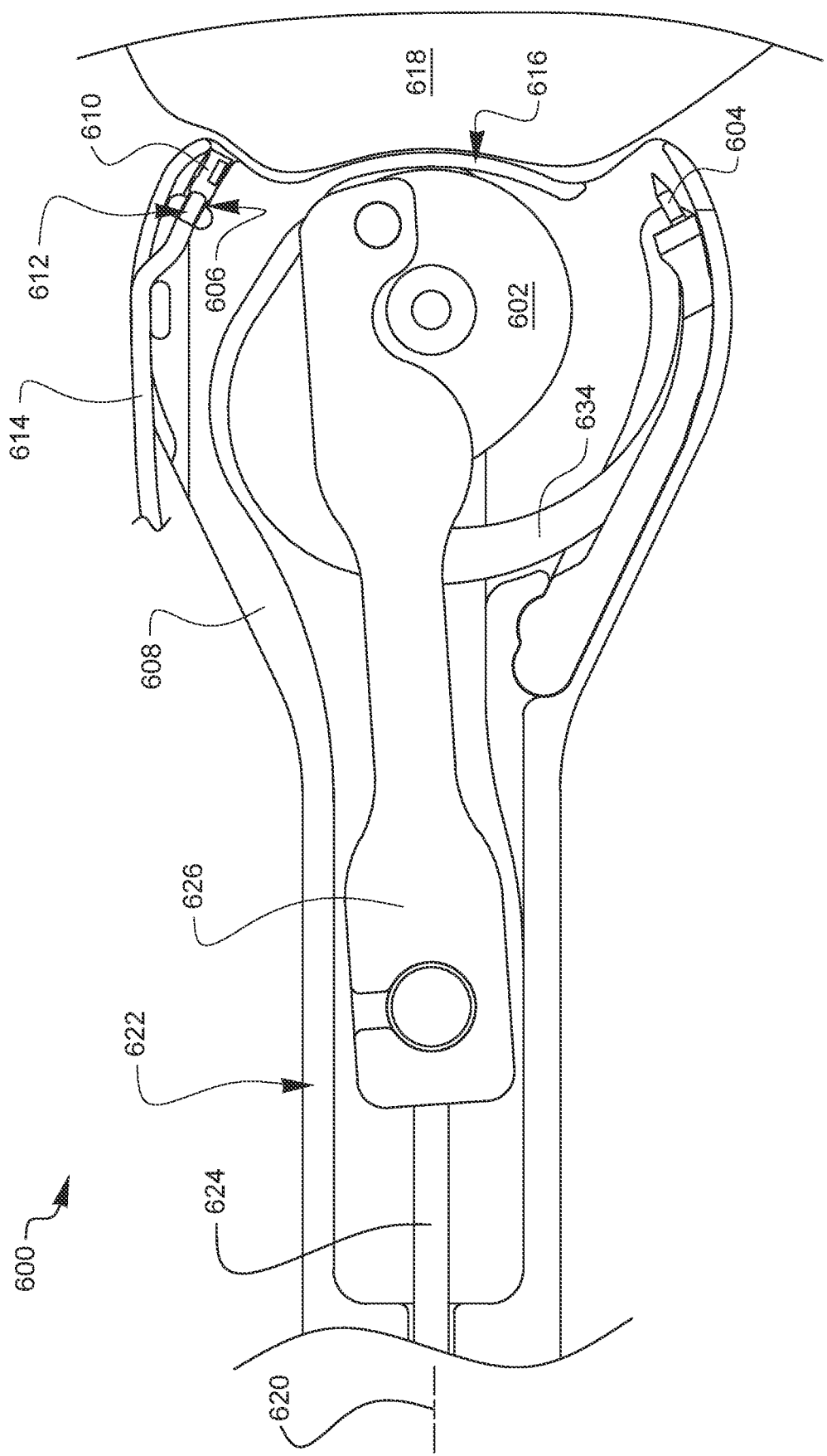
FIGS. 33A-33C illustrate the distal end of another embodiment of a surgical suturing device in an exposed side view, loaded with a suture, and illustrating the movement of the needle from a retracted position to an engaged position and back to the retracted position in order place suture in tissue.
Figure 33B:
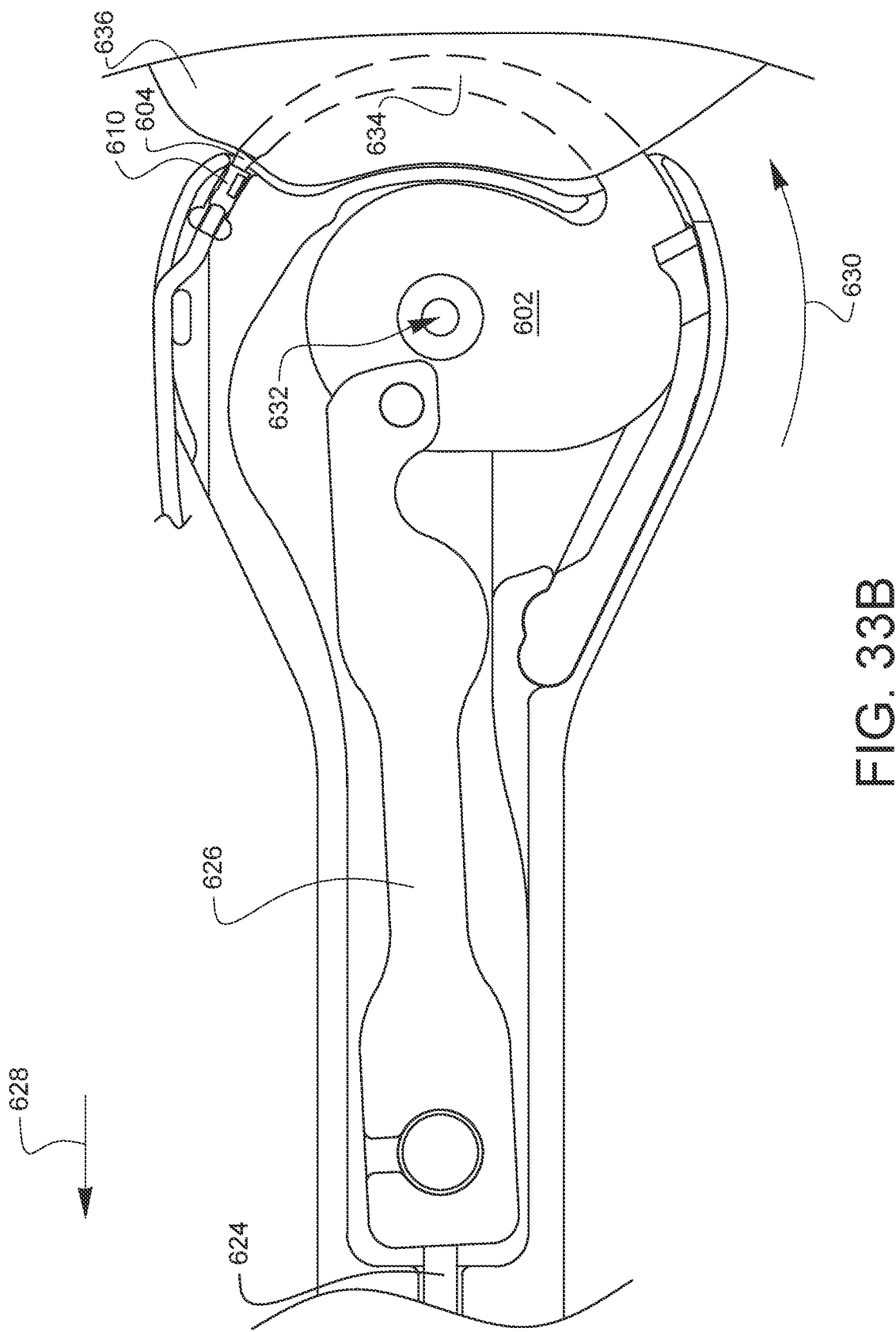
Figure 33C:
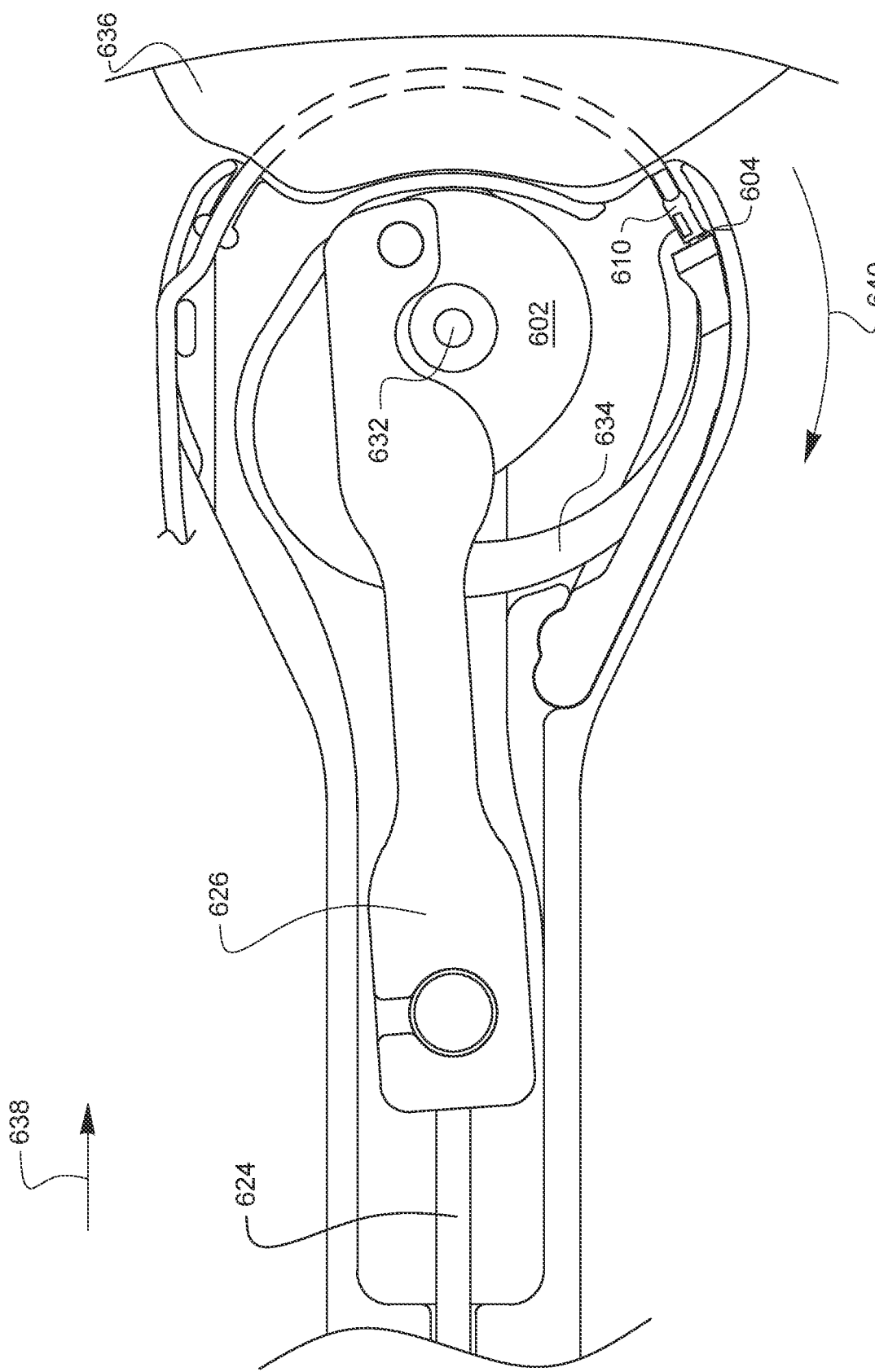

FIGS. 33A-33C show the distal end of another embodiment of a surgical suturing device 600, similar to the embodiment of FIG. 18A, but with a different needle, a wider tissue bite, and a linkage which helps to facilitate and enable release of the ferrule from the tip of the curved arm. FIG. 33A is an exposed side view, illustrating the movement of the needle 602. In FIG. 33A, the needle 602 is shown in a retracted position, where the ferrule engaging tip 604 starts away from its ferrule holder 606. The ferrule holder 606 is either formed from or coupled to the device head 608. A ferrule 610 is installed in and held by the ferrule holder 606. The ferrule 610 is coupled to a first end 612 of a suture 614. As before, it should be understood that the term "suture", as used herein, is intended to cover any thread, cable, wire, filament, strand, line, yarn, gut, or similar structure, whether natural and/or synthetic, in monofilament, composite filament, or multifilament form (whether braided, woven, twisted, or otherwise held together), as well as equivalents, substitutions, combinations, and pluralities thereof for such materials and structures.

The head 608, along with a tissue engaging surface 616 of the flywheel portion of the needle 602, defines a tissue bite area 618. In this embodiment, the tissue bite area 618 faces a direction which is substantially parallel to a longitudinal axis 620 of the shaft 622. In this embodiment, the actuator rod 624 is not coupled directly to the needle 602. Instead, the actuator rod 624 is coupled to the needle 602 by a drive link 626.

As shown in FIG. 33B, the actuator rod 624 may be moved in a proximal direction 304 by an actuator (not shown, but typically accomplished by squeezing a lever towards a handle), which will cause the drive link 626 rotate needle 602 in a first direction 630 about its needle pivot axis 632. While rotating in this first direction 630, the ferrule engaging tip 604 of the curved arm 634 passes from its retracted position (shown in FIG. 33A), through tissue 636 in the tissue bite area 618, and to an engaged position (shown in FIG. 33B). In this embodiment, the ferrule engaging tip 604 moves along an arcuate path substantially transverse to the longitudinal axis 620 of the shaft 622. In the engaged position of FIG. 33B, the ferrule engaging tip 604 is coupled to the ferrule 610 by an interference fit or alternate attachment mechanism, the choice of which is known to those skilled in the art. This coupling of the ferrule engaging tip with the corresponding ferrule may be referred to as operational alignment. While a straight shaft has been discussed herein, other configurations of shafts may be utilized in the embodiments herein, including a bent shaft, a curved shaft, a flexible shaft, a straight shaft, or combinations thereof.

As shown in FIG. 33C, the actuator rod 624 may be moved in a distal direction 638 (typically accomplished by releasing a lever which is biased away from a handle to return to a starting position), which will push distally on the drive link 626, causing the needle 602 to rotate in a second direction 640 (opposite the first direction 630) about its needle pivot axis 632. While rotating in this second direction 640, the ferrule engaging tip 604 of the curved arm 634 (and the ferrule 610 which is coupled to it) passes from its engaged position (shown in FIG. 33B), back through the tissue 636 in the tissue bite area 618, and to the retracted position as shown in FIG. 33C.

Figure 33D:
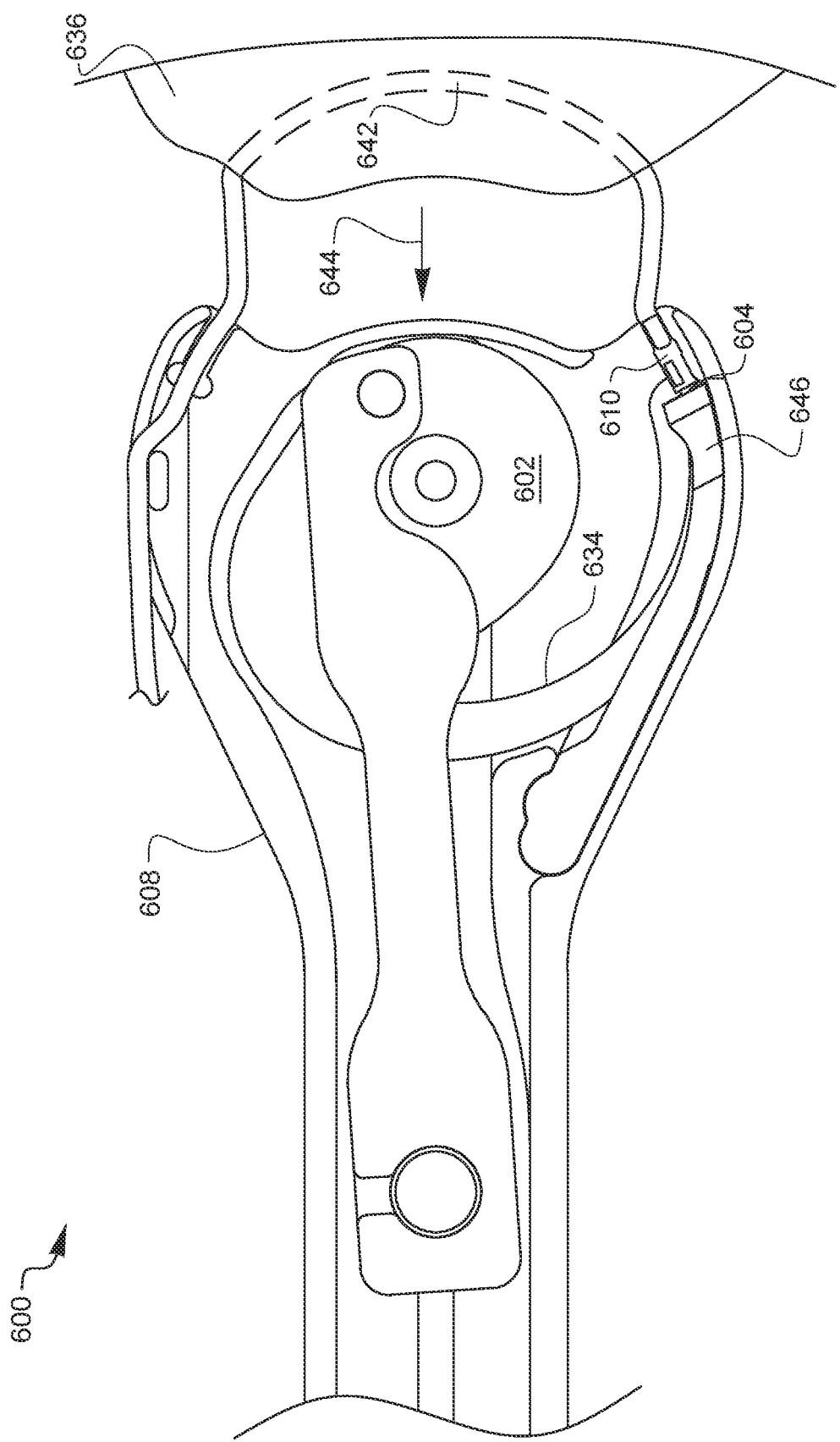
FIGS. 33D-33E illustrate the distal end of the surgical suturing device of FIGS. 33A-33C in an exposed side view, where the ferrule-engaging tip of the curved arm is initially coupled to a suture ferrule, and illustrating the movement of the needle from a retracted position to an extended retracted position in order to remove the suture ferrule from the ferrule-engaging tip of the curved arm.
Figure 33E:
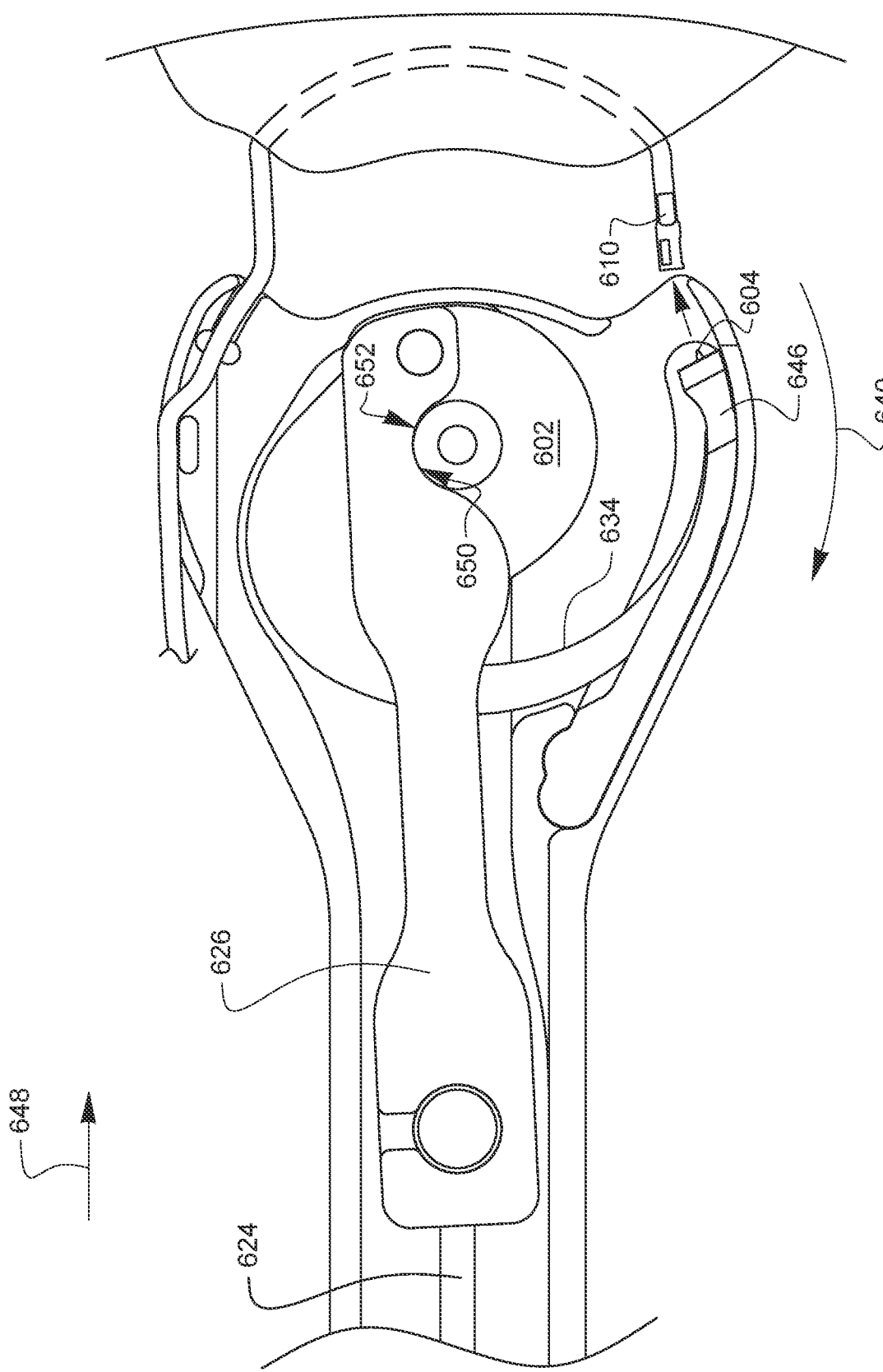

As illustrated in FIG. 33D, now that a stitch 642 has been formed in the tissue 636, the device head 608 may be pulled 644 away from the tissue 636. In this embodiment, the device 600 has a ferrule removal feature 646 which is biased against the curved arm 634 just short of where the ferrule engaging tip 604 is coupled to the ferrule 610 while the needle 602 is in the retracted position of FIG. 33D. As illustrated in FIG. 33E, the actuator rod 624 may be moved further in a distal direction 648 (typically by hyper-extending a lever away from a handle towards which it is normally squeezed when advancing the curved arm of the needle through tissue). As the actuator rod 624 moves further in the distal direction 648, the drive link 626 rotates the needle 602 further in the direction 640 such that the ferrule 610 contacts the ferrule removal feature 646 and is removed from the ferrule engaging tip 604. The drive link 626 has a motion limiting notch 650 which contacts a cam surface 652 of the needle 602 to limit how far the curved arm 634 can rotate the ferrule engaging tip 604 past the ferrule removal feature 646. This may help avoid damage to the ferrule engaging tip 604, thereby enabling subsequent sutures to be loaded into the device for further stitching.

Various advantages of a suturing device for minimally invasive surgery and needles and methods thereof have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A suturing device for minimally invasive surgery, comprising:
   a housing;
   an actuator coupled to a first portion of the housing such that the actuator is displaceable between a first actuator position and a second actuator position;
   a shaft extending from a proximal end to a distal end along a shaft axis, wherein the proximal end of the shaft is coupled to a second portion of the housing;
   a head portion extending along the shaft axis from a proximal end to a distal end, the proximal end of the head portion is coupled to the distal end of the shaft, wherein a notch is disposed along the head portion between the proximal end of the head portion and the distal end of the head portion, the notch extending from a distal end to a proximal end and defining a tissue bite area that is configured to receive a portion of tissue that is to be sutured, the head portion comprising a first ferrule holder defined by a first channel formed along a first portion of the head portion, the first channel extending along a first channel axis from a first end to a second end, wherein the first channel axis is not parallel to the shaft axis, wherein the first end of the first channel is disposed at or adjacent to the distal end of the notch, and wherein the first channel is configured to receive a first ferrule secured to a first portion of suture;
   an actuator rod coupled to a portion of the actuator, wherein as the actuator is displaced from the first actuator position to the second actuator position, a distal end of the actuator rod is displaced from a first rod position to a second rod position, and wherein as the actuator is displaced from the second actuator position to the first actuator position, the distal end of the actuator rod is displaced from the second rod position to the first rod position; and
   a needle coupled to the distal end of the actuator rod, the needle comprising a first arm extending from a first end to a second end along a first arcuate path, the second end of the first arm having a first ferrule-engaging tip, the needle being pivotable about a pivot axis such that when the actuator rod displaces from the first rod position to the second rod position, the needle rotates from a retracted position to an engaged position such that the first ferrule-engaging tip displaces through at least a portion of the tissue bite area,
   wherein in the retracted position, the first ferrule-engaging tip is disposed remote from the first ferrule holder, and in the engaged position, the first ferrule-engaging tip is disposed adjacent to or in contact with the first ferrule holder such that the first ferrule-engaging tip is configured to operatively engage the first ferrule configured to be held in the first ferrule holder.

2. The suturing device of claim 1, further comprising:
   the first ferrule secured to the first portion of suture, the first ferrule releasably secured within the first channel of the first ferrule holder.

3. The suturing device of claim 1, wherein the shaft defines an interior portion that extends from the proximal end of the shaft to the distal end of the shaft, wherein at least a portion of the actuator rod extends through the interior portion of the shaft.

4. The suturing device of claim 1, wherein the second end of the first channel is disposed (a) at the distal end of the head portion or (b) between the distal end of the notch and the distal end of the head portion.

5. The suturing device of claim 1, wherein the actuator is pivotably coupled to the first portion of the housing such that the actuator is pivotably displaceable between the first actuator position and the second actuator position.

6. The suturing device of claim 5, wherein as the actuator is pivoted from the first actuator position to the second actuator position, the distal end of the actuator rod is displaced distally from the first rod position to the second rod position, and wherein as the actuator is pivoted from the second actuator position to the first actuator position, the distal end of the actuator rod is displaced proximally from the second rod position to the first rod position.

7. The suturing device of claim 1, wherein the distal end of the actuator rod is displaced linearly from the first rod position to the second rod position.

8. The suturing device of claim 1, wherein the actuator rod is elongated, and a proximal end of the actuator rod is coupled to the portion of the actuator.

9. The suturing device of claim 1, the needle further comprising a flywheel portion, wherein the pivot axis extends through the flywheel portion, and wherein the first end of the first arm is coupled to a first portion of the flywheel portion.

10. The suturing device of claim 9, wherein the first end of the first arm is integrally formed with the flywheel portion such that the flywheel portion and the first arm form a single, unitary part.

11. The suturing device of claim 9, the needle further comprising a second arm extending from a first end to a second end, the second end of the second arm having a second ferrule-engaging tip, and wherein the first end of the second arm is coupled to a second portion of the flywheel portion.

12. The suturing device of claim 11, wherein the first arm extends from the first end of the first arm to the second end of the first arm along the first arcuate path when viewed along the pivot axis and the second arm extends from the first end of the second arm to the second end of the second arm along a second arcuate path when viewed along the pivot axis.

13. The suturing device of claim 9, wherein the distal end of the actuator rod is coupled to a second portion of the flywheel portion adjacent to a peripheral edge of the flywheel portion.

14. The suturing device of claim 13, wherein a portion of the actuator rod extends through a passage of the head portion, the passage extending from a proximal end to a distal end, wherein when the distal end of the actuator rod is in the first rod position, the second portion of the flywheel portion is adjacent to the distal end of the passage of the head portion.

15. The suturing device of claim 14, wherein when the distal end of the actuator rod is in the second rod position, the second portion of the flywheel portion is adjacent to the distal end of the head portion.

16. The suturing device of claim 1, wherein the second end of the first arm is pointed and configured to penetrate the portion of tissue that is received in the tissue bite area as the needle rotates from the retracted position to the engaged position.

17. The suturing device of claim 1, wherein a portion of the housing defines a grip portion, and wherein in the first actuator position, a lever portion of the actuator is in a first position relative to the grip portion of the housing and in the second actuator position, the lever portion of the actuator is in a second position relative to the grip portion of the housing.

18. The suturing device of claim 1, wherein the notch is formed along a lateral edge of the head portion and the notch extends parallel to the shaft axis from the distal end of the notch to the proximal end of the notch.

19. The suturing device of claim 18, wherein when the needle is in the retracted position, the first ferrule-engaging tip is disposed adjacent to the distal end of the notch, and when the needle is in the engaged position, the first ferrule-engaging tip is disposed adjacent to the proximal end of the notch.

* * * * *